United States Patent
Becherer et al.

(10) Patent No.: US 9,840,496 B2
(45) Date of Patent: Dec. 12, 2017

(54) CD38 INHIBITORS AND METHODS OF TREATMENT

(71) Applicant: GlaxoSmithKline Intellectual Property (No.2) Limited, Brentford, Middlesex (GB)

(72) Inventors: J. David Becherer, Research Triangle Park, NC (US); Rodolfo Cadilla, King of Prussia, PA (US); David Norman Deaton, King of Prussia, PA (US); Curt Haffner, King of Prussia, PA (US); Brad Richard Henke, Research Triangle Park, NC (US); Frank Preugschat, Research Triangle Park, NC (US); Christie Schulte, King of Prussia, PA (US)

(73) Assignee: GLAXOSMITHKLINE INTELLECTUAL PROPERTY (NO.2) LIMITED, Brentford, Middlesex (GB)

( * ) Notice: Subject to any disclaimer, the term of this patent is extended or adjusted under 35 U.S.C. 154(b) by 0 days.

(21) Appl. No.: 15/529,120

(22) PCT Filed: Nov. 19, 2015

(86) PCT No.: PCT/IB2015/058965
§ 371 (c)(1),
(2) Date: May 24, 2017

(87) PCT Pub. No.: WO2016/087975
PCT Pub. Date: Jun. 9, 2016

(65) Prior Publication Data
US 2017/0260164 A1    Sep. 14, 2017

Related U.S. Application Data

(60) Provisional application No. 62/086,844, filed on Dec. 3, 2014.

(51) Int. Cl.
*C07D 403/04* (2006.01)

(52) U.S. Cl.
CPC .................................. *C07D 403/04* (2013.01)

(58) Field of Classification Search
CPC ...................................................... C07D 403/04
See application file for complete search history.

(56) References Cited

FOREIGN PATENT DOCUMENTS

WO      WO 03/101198 A1    12/2003

OTHER PUBLICATIONS

Chemical Abstracts Registry No. 1528515-70-9 , indexed in the Registry file on STN CAS ONLINE Jan. 23, 2014.*

* cited by examiner

*Primary Examiner* — Laura L. Stockton
(74) *Attorney, Agent, or Firm* — Robert H. Brink; Edward R. Gimmi; William R. Majarian

(57) ABSTRACT

Compounds of Formula I and methods of treating diseases of metabolism by modulating cellular NAD+ levels through the inhibition of the CD38 enzyme, are disclosed.

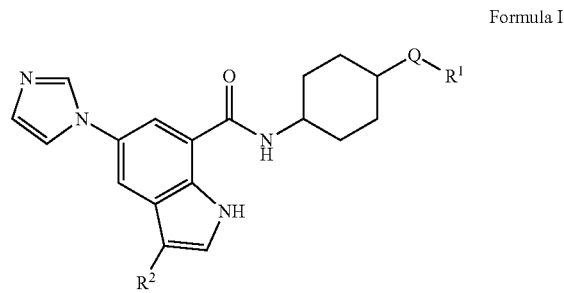

Formula I

6 Claims, 1 Drawing Sheet

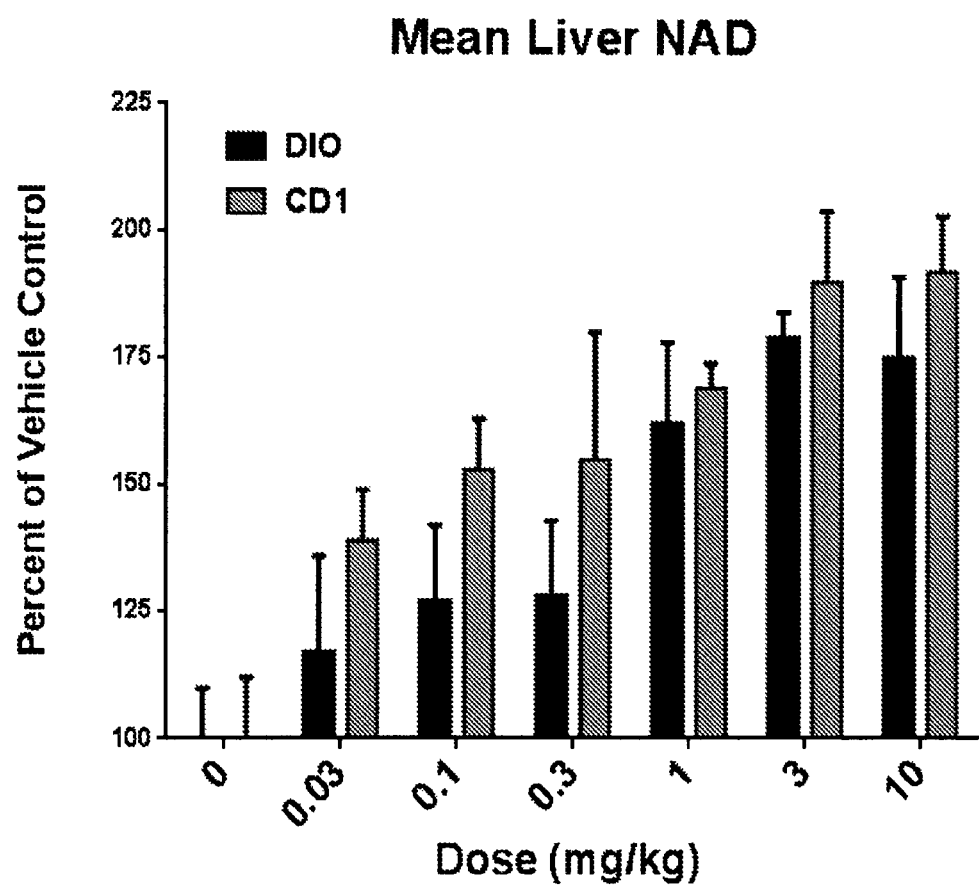

CD38 INHIBITORS AND METHODS OF TREATMENT

This application is a §371 of International Application No. PCT/IB2015/058965, filed 19 Nov. 2015, which claims the benefit of U.S. Provisional Application No. 62/086,844, filed 3 Dec. 2014.

FIELD OF THE INVENTION

The present invention relates to compounds, and to methods of treating diseases of metabolism by modulating cellular NAD+ levels through the inhibition of the CD38 enzyme.

BACKGROUND OF THE INVENTION

Nicotinamide Adenine Dinucleotide (NAD+) is a biochemical found in all cells that was first characterized over 100 years ago due to its role in oxidoreductase reactions. Since then NAD+ and its related pyridine nucleotides NADH, NADP+, and NADPH are recognized as the major redox carriers in all organisms. These pyridine dinucleotides regulate the cytosolic and mitochondrial redox state and are key participants monitoring the metabolic status of the cell. This is because NAD+ and NADH act as hydride accepting and donating cofactors for metabolic enzymes involved in glycolysis, the TCA cycle, and the respiratory chain and thereby redistribute reducing equivalents generated from these catabolic processes into the de novo synthesis of new biomolecules. (Houtkooper et al Endo Reviews (2010) 31:194-223; Koch-Nolte et al (2009) Science Signaling 2:mr1; Houtkooper and Auwerx (2012) J. Cell Biol 199: 205-209; Berger et al Trends in Bioch Sci 29:11-118)

In addition to its long recognized role as a cofactor for oxidoreductases, more recent research demonstrates that NAD+ is also a substrate for various enzymes, where it is consumed in the process of donating its ADP ribose to acceptor molecules. The enzymes that are the major consumers of NAD+ are the ADP ribosyl transferases (i.e. PARP and ART family of enzymes), the sirtuins (Sirt1-7), and the ADP ribosyl cyclases/hydrolases (CD38/CD157). These enzymes are involved in pathways that regulate Ca++ signaling, gene transcription, DNA repair, cell survival, energy metabolism, and oxidative stress. Thus, NAD+ and its phosphorylated relatives NADP and NAADP, both of which are derived from NAD+, also act as signaling molecules. NAD+ is also a key component of the circadian cycle with daily oscillations that tie cellular metabolism to chromatin remodeling and gene transcription. It is known that exercise and caloric restriction elevate NAD+ levels while aging and obesity decrease cellular NAD+ levels. Restoring NAD++ levels in disease states that consume significant amounts of NAD++ will likely have medical benefits as the cell strives to maintain its energy status during stress. (Tevy et al (2103) Trends in Endo and Metab 24:229-237; Pugh et al (2013) Aging Cell 12:672-681; Massudi et al PLoS ONE 7:e42357; Xu and Sauve (2010) Mech of Ageing and Development 131:287-298; Sassone-Corsi (2012) 153:1-5).

Cellular NAD+ is produced by either the de novo synthesis pathway from tryptophan or by a salvage synthesis pathway from precursors such as nicotinic acid (niacin) and nicotinamide, both of which are obtained from dietary sources. A third way to modulate cellular NAD+ levels is to block consumption of NAD+ by inhibiting enzymes that consume NAD+. CD38 is one such consumer of NAD+. Also known as ADP ribosyl cyclase, CD38 is a type II membrane-anchored enzyme. It efficiently catalyzes the breakdown of NAD+ to nicotinamide and ADPR and hydrolyzes NAADP to ADPRP. CD38 can also act as a cyclase converting NAD+ to cADPR, although it is 100-fold less efficient as a cyclase than as a hydrolase. CD38 was first characterized as a surface antigen on immune cells and is broadly distributed throughout most tissues in the body. It exists on the plasma membrane and on the membranes of intracellular organelles such as the nucleus and mitochondria. As predicted from its function as a NAD+ glycohydrolase, CD38 KO mice have elevated NAD+ levels relative to wild-type controls. Likewise, inhibitors of CD38 enzyme activity also modulate NAD+ tissue levels and would be useful in treating various diseases where CD38 is over expressed or where cellular NAD+ levels are depressed or desynchronized. (Malavasi et al (2008) 88:841-886)

There are many references suggesting the benefits of modulating NAD+ levels. Compounds which inhibit CD38, and thereby raise NAD+ levels may be useful in treating diseases or conditions indicated to benefit from NAD+. The following are examples, with references:

acute lung injury/ARDS, see, for example, Nicotinamide abrogates acute lung injury caused by ischaemia/reperfusion, Su, $C_{1-5}$. F.; Liu, D. D.; Kao, S. J.; Chen, H. I. European Respiratory Journal (2007), 30(2), 199-204;

hyperphosphatemia, see for example, Nicotinamide suppresses hyperphosphatemia in hemodialysis patients, Takahashi, Yutaka; Tanaka, Araki; Nakamura, Tsukasa; Fukuwatari, Tsutomu; Shibata, Katsumi; Shimada, Noriaki; Ebihara, Isao; Koide, Hikaru, Kidney International (2004), 65(3), 1099-1104;

alcohol intolerance, see for example, Disruption of the coenzyme binding site and dimer interface revealed in the crystal structure of mitochondrial aldehyde dehydrogenase "Asian" variant, Larson, Heather N.; Weiner, Henry; Hurley, Thomas D. Journal of Biological Chemistry (2005), 280(34), 30550-30556;

lupus, see for example, CD38 polymorphisms in Spanish patients with systemic lupus erythematosus, Gonzalez-Escribano Maria Francisca; Aguilar Francisco; Torres Belen; Sanchez-Roman Julio; Nunez-Roldan Antonio Human immunology (2004), 65(6), 660-4, and Increased CD38 expression in T cells and circulating anti-CD38 IgG autoantibodies differentially correlate with distinct cytokine profiles and disease activity in systemic lupus erythematosus patients Pavon, Esther J.; Zumaquero, Esther; Rosal-Vela, Antonio; Khoo, Keng-Meng; Cerezo-Wallis, Daniela; Garcia-Rodriguez, Sonia; Carrascal, Montserrat; Abian, Joaquin; Graeff, Richard; Callejas-Rubio, Jose-Luis; et al Cytokine+ (2013), 62(2), 232-243;

rheumatoid arthritis, see, for example, Mice deficient in CD38 develop an attenuated form of collagen type Il-induced arthritis Postigo, Jorge; Iglesias, Marcos; Cerezo-Wallis, Daniela; Rosal-Vela, Antonio; Garcia-Rodriguez, Sonia; Zubiaur, Mercedes; Sancho, Jaime; Merino, Ramon; Merino, Jesus PLoS One (2012), 7(3), e33534;

ataxia-telangiectasia, see, for example, Accumulation of DNA damage and reduced levels of nicotine adenine dinucleotide in the brains of Atm-deficient mice Stern, Nora; Hochman, Ayala; Zemach, Naty; Weizman, Nir; Hammel, Ilan; Shiloh, Yosef; Rotman, Galit; Barzilai, An, Journal of Biological Chemistry (2002), 277(1), 602-608;

sleep disorders, see, for example, The effects of nicotinamide upon sleep in humans Robinson C R; Pegram G V; Hyde P R; Beaton J M; Smythies J R Biological psychiatry (1977)), 12(1), 139-43;

epilepsy, see, for example, Partial epilepsy with pericentral spikes: a new familial epilepsy syndrome with evidence for linkage to chromosome 4p15 Kinton Lucy; Johnson Michael R; Smith Shelagh J M; Farrell Fiona; Stevens John; Rance James B; Claudino Angelica M; Duncan John S; Davis Mary B; Wood Nicholas W; et al Annals of neurology (2002), 51(6), 740-9;

exercise intolerance, see, for example, Effects of exercise on oxidative activities in rat liver mitochondria, Glick, J. Leslie American Journal of Physiology (1966), 210 (6), 1215-21;

small lung cell carcinoma, see, for example, β-Lapachone Micellar Nanotherapeutics for Non-Small Cell Lung Cancer Therapy, Blanco, Elvin; Bey, Erik A.; Khemtong, Chalermchai; Yang, Su-Geun; Setti-Guthi, Jagadeesh; Chen, Huabing; Kessinger, Chase W.; Carnevale, Kevin A.; Bornmann, William G.; Boothman, David A.; et al Cancer Research (2010), 70(10), 3896-3904;

renal clear cell carcinoma, see, for example, Identification of nicotinamide N-methyltransferase as a novel tumor marker for renal clear cell carcinoma Sartini, Davide; Muzzonigro, Giovanni; Milanese, Giulio; Pierella, Francesca; Rossi, Valentina; Emanuelli, Monica Journal of Urology (New York, N.Y., United States) (2006), 176(5), 2248-2254;

hypertension, see, for example, Mice lacking the ADP ribosyl cyclase CD38 exhibit attenuated renal vasoconstriction to angiotensin II, endothelin-1, and norepinephrine Thai Tiffany L; Arendshorst William J American journal of physiology. Renal physiology (2009), 297(1), F169-76;

hypoxic pulmonary vasoconstriction, see, for example, Adp-ribosyl cyclase and cyclic ADP-ribose hydrolase act as a redox sensor. a primary role for cyclic ADP-ribose in hypoxic pulmonary vasoconstriction, Wilson H L; Dipp M; Thomas J M; Lad C; Galione A; Evans A M The Journal of biological chemistry (2001), 276 (14), 11180-8;

hansen's disease, see, for example, Nicotinamide adenine dinucleotide glycohydrolase in normal and leprous armadillos Dhople, Arvind M.; Johnson, Kara J.; Williams, Sharon L.; Zeigler, Joseph A.; Cook, Camille A.; Storrs, Eleanor E. Microbios Letters (1985), 28(109), 17-20;

tuberculosis, see, for example, NAD+ auxotrophy is bactericidal for the tubercle bacilli, Vilcheze, Catherine; Weinrick, Brian; Wong, Ka-Wing; Chen, Bing; Jacobs, William R., Jr. Molecular Microbiology (2010), 76(2), 365-377;

leishmaniasis, see, for example, The NAD+ metabolism of Leishmania, notably the enzyme nicotinamidase involved in NAD+ salvage, offers prospects for development of anti-parasite chemotherapy Michels Paul A M; Avilan Luisana Molecular microbiology (2011), 82(1), 4-8;

cardiac hypertrophy/CHF, see, for example, Exogenous NAD+ Blocks Cardiac Hypertrophic Response via Activation of the SIRT3-LKB1-AMP-activated Kinase Pathway Pillai, Vinodkumar B.; Sundaresan, Nagalingam R.; Kim, Gene; Gupta, Madhu; Rajamohan, Senthilkumar B.; Pillai, Jyothish B.; Samant, Sadhana; Ravindra, P. V.; Isbatan, Ayman; Gupta, Mahesh P., Journal of Biological Chemistry (2010), 285(5), 3133-3144;

muscular dystrophy, see, for example, NAD+ biosynthesis ameliorates a zebrafish model of muscular dystrophy, Goody, Michelle F.; Kelly, Meghan W.; Reynolds, Christine J.; Khalil, Andre; Crawford, Bryan D.; Henry, Clarissa A. PLoS Biology (2012), 10(10), e1001409;

stroke, see, for example, CD38 exacerbates focal cytokine production, postischemic inflammation and brain injury after focal cerebral ischemia, Choe, Chi-un; Lardong, Kerstin; Gelderblom, Mathias; Ludewig, Peter; Leypoldt, Frank; Koch-Nolte, Friedrich; Gerloff, Christian; Magnus, Tim PLoS One (2011), 6(5), e19046;

organ reperfusion injury, see, for example, Mouse embryonic fibroblasts from CD38 knockout mice are resistant to oxidative stresses through inhibition of reactive oxygen species production and Ca2+ overload Ge, Yan; Jiang, Wei; Gan, Lu; Wang, Li-Jun; Sun, Chang-Yan; Ni, Pei-Yan; Liu, Yin; Wu, Si-Si; Gu, Lun-Da; Zheng, Wei; et al Biochemical and Biophysical Research Communications (2010), 399(2), 167-172;

idiopathic pulmonary fibrosis, see, for example, Biochemical mechanisms for the attenuation of bleomycin-induced lung fibrosis by treatment with niacin in hamsters: the role of NAD+ and ATP O'Neill, Charles A.; Giri, Shri N. Experimental Lung Research (1994), 20(1), 41-56;

pancreatitis, see, for example, The Renin-Angiotensin System and Reactive Oxygen Species: Implications in Pancreatitis Chan, Yuk Cheung; Leung, Po Sing Antioxidants & Redox Signaling (2011), 15(10), 2743-2755;

cystic fibrosis, see, for example, Metabolomic Profiling Reveals Biochemical Pathways and Biomarkers Associated with Pathogenesis in Cystic Fibrosis Cells Wetmore, Diana R.; Joseloff, Elizabeth; Pilewski, Joseph; Lee, Douglas P.; Lawton, Kay A.; Mitchell, Matthew W.; Milburn, Michael V.; Ryals, John A.; Guo, Lining, Journal of Biological Chemistry (2010), 285(40), 30516-30522;

asthma, see, for example, Role of CD38 in airway function, Kang, Bit Na; Guedes, Alonso G. P.; Tirumurugaan, K. G.; Jude, Joseph A.; Deshpande, Deepak A.; Panettieri, Reynold A.; Amrani, Yassine; Lund, Frances E.; Walseth, Timothy F.; Kannan, Mathur S. Current Respiratory Medicine Reviews (2006), 2(2), 143-156;

COPD, see, for example, Systemic poly(ADP-ribose) polymerase-1 activation, chronic inflammation, and oxidative stress in COPD patients, Hageman, Geja J.; Lark, Ingrid; Pennings, Herman-Jan; Haenen, Guido R. M. M.; Wouters, Emiel F. M.; Bast, Aalt Free Radical Biology & Medicine (2003), 35(2), 140-148;

Irritable Bowel Syndrome/Colitis, see, for example, Adenosine 5'-diphosphate-ribose is a neural regulator in primate and murine large intestine along with β-NAD+ Durnin, Leonie; Hwang, Sung Jin; Ward, Sean M.; Sanders, Kenton M.; Mutafova-Yambolieva, Violeta N. Journal of Physiology (Oxford, United Kingdom) (2012), 590(8), 1921-1941;

gout, see, for example, Genome-wide scan identifies a quantitative trait locus at 4p15.3 for serum urate, Cummings Nik; Dyer Thomas D; Kotea Navaratnam; Kowlessur Sudhir; Chitson Pierrot; Zimmet Paul; Blangero John; Jowett Jeremy B M European journal of human genetics: EJHG (2010), 18(11), 1243-7;

obesity/sarcopenic obesity, see, for example, The enzyme CD38 (a NAD+ glycohydrolase, EC 3.2.2.5) is necessary for the development of diet-induced obesity Barbosa Maria Thereza P; Soares Sandra M; Novak Colleen M; Sinclair David; Levine James A; Aksoy Pinar; Chini Eduardo Nunes, FASEB journal: official publication of the Federation of American Societies for Experimental Biology (2007), 21(13), 3629-39;

Metabolic Syndrome, see, for example, Flavonoid apigenin is an inhibitor of the NAD+ ase CD38: implications for cellular NAD+ metabolism, protein acetylation, and treatment of metabolic syndrome, Escande Carlos; Nin Veronica; Price Nathan L; Capellini Verena; Gomes Ana P; Barbosa Maria Thereza; O'Neil Luke; White Thomas A; Sinclair David A; Chini Eduardo N Diabetes (2013), 62(4), 1084-93;

end stage renal disease, see, for example, A genome scan for all-cause end-stage renal disease in African Americans, Freedman, Barry I.; Bowden, Donald W.; Rich, Stephen S.; Valis, Christopher J.; Sale, Michele M.; Hicks, Pamela J.; Langefeld, Carl D. Nephrology, Dialysis, Transplantation (2005), 20(4), 712-718;

dyslipidemia, see, for example, A genome-wide screen for interactions reveals a new locus on 4p15 modifying the effect of waist-to-hip ratio on total cholesterol, Surakka Ida; Isaacs Aaron; Karssen Lennart C; Laurila Pirkka-Pekka P; Middelberg Rita P S; Tikkanen Emmi; Ried Janina S; Lamina Claudia; Mangino Massimo; Igl Wilmar; et al PLoS genetics (2011), 7(10), e1002333;

hearing loss, see, for example, Sirt3 mediates reduction of oxidative damage and prevention of age-related hearing loss under caloric restriction Someya, Shinichi; Yu, Wei; Hallows, William C.; Xu, Jinze; Vann, James M.; Leeuwenburgh, Christiaan; Tanokura, Masaru; Denu, John M.; Prolla, Tomas A. Cell (Cambridge, Mass., United States) (2010), 143(5), 802-812;

steatosis/NASH, see, for example, Elevated microRNA-34a in obesity reduces NAD+(+) levels and SIRT1 activity by directly targeting NAMPT Choi Sung-E; Fu Ting; Seok Sunmi; Kim Dong-Hyun; Yu Eunkyung; Lee Kwan-Woo; Kang Yup; Li Xiaoling; Kemper Byron; Kemper Jongsook Kim Aging cell (2013);

Alzheimer's disease, see, for example, Nicotinamide riboside restores cognition through an upregulation of proliferator-activated receptor-γ coactivator 1α regulated β-secretase 1 degradation and mitochondrial gene expression in Alzheimer's mouse models Gong Bing; Pan Yong; Vempati Prashant; Zhao Wei; Knable Lindsay; Ho Lap; Wang Jun; Sastre Magdalena; Ono Kenjiro; Sauve Anthony A; et al Neurobiology of aging (2013), 34(6), 1581-8;

multiple sclerosis, see, for example, The importance of NAD+ in multiple sclerosis, Penberthy, W. Todd; Tsunoda, Ikuo Current Pharmaceutical Design (2009), 15(1), 64-99;

neurocognitive disorders, see, for example, CD38/cyclic ADP-ribose regulates astrocyte calcium signaling: implications for neuroinflammation and HIV-1-associated dementia Banerjee Sugato; Walseth Timothy F; Borgmann Kathleen; Wu Li; Bidasee Keshore R; Kannan Mathur S; Ghorpade Anuja Journal of neuroimmune pharmacology: The official journal of the Society on NeuroImmune Pharmacology (2008), 3(3), 154-64;

optic neuropathy, see, for example, Axonal and cell body protection by nicotinamide adenine dinucleotide in tumor necrosis factor-induced optic neuropathy Kitaoka, Yasushi; Hayashi, Yasuhiro; Kumai, Toshio; Takeda, Hiroyuki; Munemasa, Yasunari; Fujino, Hiromi; Kitaoka, Yuka; Ueno, Satoki; Sadun, Alfredo A.; Lam, Tim T. Journal of Neuropathology & Experimental Neurology (2009), 68(8), 915-927;

postmenopausal osteoporosis, see, for example, CD38 is associated with premenopausal and postmenopausal bone mineral density and postmenopausal bone loss Drummond Frances J; Mackrill John J; O'sullivan Kathleen; Daly Mary; Shanahan Fergus; Molloy Michael G Journal of bone and mineral metabolism (2006), 24(1), 28-35;

Bipolar disorder/Schizophrenia, see, for example, Association analysis of the chromosome 4p15-p16 candidate region for bipolar disorder and schizophrenia, Christoforou, A.; Le Hellard, S.; Thomson, P. A.; Morris, S. W.; Tenesa, A.; Pickard, B. S.; Wray, N. R.; Muir, W. J.; Blackwood, D. H.; Porteous, D. J.; Molecular Psychiatry (2007), 12(11), 1011-1025;

Huntington's disease, see, for example, The gene coding for PGC-1alpha modifies age at onset in Huntington's Disease, Weydt Patrick; Soyal Selma M; Gellera Cinzia; Didonato Stefano; Weidinger Claus; Oberkofler Hannes; Landwehrmeyer G Bernhard; Patsch Wolfgang Molecular neurodegeneration (2009), 4, 3;

diabetes, see, for example, Evidence of a novel quantitative-trait locus for obesity on chromosome 4p in mexican Americans Arya, Rector; Duggirala, Ravindranath; Jenkinson, Christopher P.; Almasy, Laura; Blangero, John; O'Connell, Peter; Stern, Michael P. American Journal of Human Genetics (2004), 74(2), 272-282;

Hartnup disease, see, for example, Hartnup disease Jepson, John B.; Spiro, Mary Jane, Metabolic Basis of Inherited Disease (1960), 1338-64;

Pellagra, see, for example, Pellagra: A clue as to why energy failure causes diseases? Williams, Adrian C.; Ramsden, David B. Medical Hypotheses (2007), 69(3), 618-628;

skin hyperpigmentation, see, for example, Oxidation of reduced nicotinamide adenine dinucleotide by melanin, Van Woert M H Life sciences (1967), 6(24), 2605-12;

diabetic neuropathy, see, for example, Functional and biochemical evidence indicating beneficial effect of Melatonin and Nicotinamide alone and in combination in experimental diabetic neuropathy, Negi Geeta; Kumar Ashutosh; Kaundal Ravinder K; Gulati Anil; Sharma Shyam S, Neuropharmacology (2010), 58(3), 585-92;

radiation protection, see, for example, NAD+ administration significantly attenuates synchrotron radiation X-ray-induced DNA damage and structural alterations of rodent testes Sheng, Caibin; Chen, Heyu; Wang, Ban; Liu, Tengyuan; Hong, Yunyi; Shao, Jiaxiang; He, Xin; Ma, Yingxin; Nie, Hui; Liu, Na; et al International Journal of Physiology, Pathophysiology and Pharmacology (2012), 4(1), 1-9;

UV skin damage, see, for example, NAD in skin: therapeutic approaches for niacin Benavente, Claudia A.; Jacobson, Myron K.; Jacobson, Elaine L. Current Pharmaceutical Design (2009), 15(1), 29-38;

psoriasis, see, for example, In search for new antipsoriatic agents: NAD+ topical composition, Wozniacka A; Szajerski P; Adamus J; Gebicki J; Sysa-Jedrzejowska A Skin pharmacology and physiology (2007), 20(1), 37-42;

periodontal disease, see, for example, CD38 expression in neutrophils from patients with localized aggressive periodontitis, Fujita Tsuyoshi; Kantarci Alpdogan;

Warbington Martha L; Zawawi Khalid H; Hasturk Hatice; Kurihara Hidemi; Van Dyke Thomas E Journal of periodontology (2005), 76(11), 1960-5;

chronic lymphocytic leukemia, see, for example, CD38 as a molecular compass guiding topographical decisions of chronic lymphocytic leukemia cells, Deaglio, Silvia; Vaisitti, Tiziana; Zucchetto, Antonella; Gattei, Valter; Malavasi, Fabio Seminars in Cancer Biology (2010), 20(6), 416-423;

amyelotrophic lateral sclerosis, see, for example, Biochemical alterations associated with ALS, Lawton, Kay A.; Cudkowicz, Merit E.; Brown, Meredith V.; Alexander, Danny; Caffrey, Rebecca; Wulff, Jacob E.; Bowser, Robert; Lawson, Robert; Jaffa, Matt; Milburn, Michael V.; et al Amyotrophic Lateral Sclerosis (2012), 13(1), 110-118;

Parkinson's disease, see, for example, Nicotinamide-N-methyltransferase is higher in the lumbar cerebrospinal fluid of patients with Parkinson's disease, Aoyama K; Matsubara K; Kondo M; Murakawa Y; Suno M; Yamashita K; Yamaguchi S; Kobayashi S Neuroscience letters (2001), 298(1), 78-80;

Leber's hereditary amaurosis, see, for example, Mutations in NMNAT1 cause Leber congenital amaurosis and identify a new disease pathway for retinal degeneration Koenekoop, Robert K.; Wang, Hui; Majewski, Jacek; Wang, Xia; Lopez, Irma; Ren, Huanan; Chen, Yiyun; Li, Yumei; Fishman, Gerald A.; Genead, Mohammed; et al., Nature Genetics (2012), 44(9), 1035-1039;

insulin resistance, see, for example, Nicotinamide Mononucleotide, a Key NAD+ Intermediate, Treats the Pathophysiology of Diet- and Age-Induced Diabetes in Mice, Yoshino, Jun; Mills, Kathryn F.; Yoon, Myeong Jin; Imai, Shin-ichiro, Cell Metabolism (2011), 14(4), 528-536;

type I diabetes, see, for example, The use of nicotinamide in the prevention of type 1 diabetes, Elliott, R. B.; Pilcher, C. C.; Stewart, A.; Fergusson, D.; McGregor, M. A. Annals of the New York Academy of Sciences (1993), 696 (Immunosuppressive and Antiinflammatory Drugs), 333-41.

SUMMARY OF THE INVENTION

Briefly, in one aspect, the present invention discloses compounds of Formula I

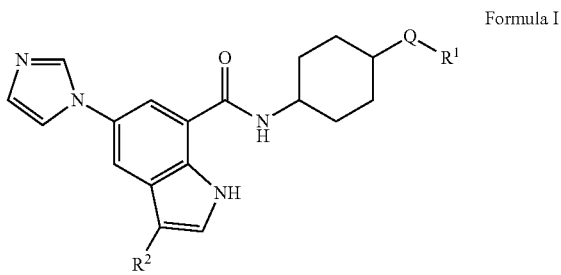

Formula I wherein Q is O, NH, N(H)C(O), or C(O)N(H);

$R^1$ is $C_{1-5}$alkylS(O)$_2$CH$_3$, or $C_{1-6}$alkyl wherein said alkyl can comprise straight-chain portions, branched chain portions, cycloalkyl portions, and wherein said $C_{1-6}$alkyl is optionally substituted by one OH or OCH$_3$ and wherein said $C_{1-6}$alkyl is optionally further substituted by 1 to 3 Fluorine atoms; and $R^2$ is H, $C_{1-3}$alkyl, or halogen.

In another aspect, the present invention discloses pharmaceutically acceptable salts of the compounds of Formula I.

In another aspect, the present invention discloses a method of treating a disease or condition that benefits from an increase in NAD+, comprising administration of a compound or salt of the invention.

BRIEF DESCRIPTION OF THE DRAWINGS

FIG. 1 summarizes the results from the LCMS method for NAD++ compound in vivo analysis, which is described beginning on page 61 and continuing on to page 62.

DETAILED DESCRIPTION OF THE INVENTION

Preferably, $R^2$ is H or Cl. Most preferably $R^2$ is H.

Preferably, the compounds of Formula I have the trans orientation on the cyclohexyl ring depicted below.

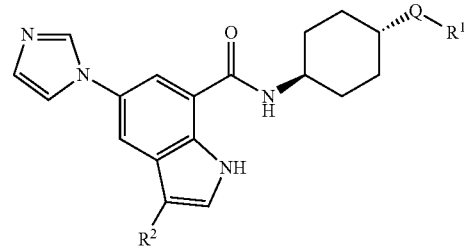

The present invention relates to the discovery of certain inhibitors of the CD38 enzyme that can be used for diseases where CD38 is over expressed or where elevating NAD+ levels will have beneficial effects by attenuating disease progression. The inventors here show compounds that inhibit CD38 potently and elevate blood and tissue NAD+ levels when given to rodents. These inhibitors can be used to treat a variety of diseases because NAD++ has a role in energy metabolism, oxidative stress, Ca++ homeostasis, gene transcription, mitochondrial function, and cellular apoptosis. Examples of diseases that can benefit from administration of CD38 inhibitors are given in the background section.

In particular, the compounds of the present invention may be useful for treating nonalcoholic steatohepatitis (NASH), chronic obstructive pulmonary disorder (COPD), and rheumatoid arthritis (RA).

EXAMPLES

The compounds of this invention may be made by a variety of methods, including well-known standard synthetic methods. Illustrative general synthetic methods are set out below and then specific compounds of the invention are prepared in the working Examples.

In all of the schemes described below, protecting groups for sensitive or reactive groups are employed where necessary in accordance with general principles of synthetic chemistry. Protecting groups are manipulated according to standard methods of organic synthesis (T. W. Green and P.

G. M. Wuts (1991) Protecting Groups in Organic Synthesis, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of Formula (I).

Those skilled in the art will recognize if a stereocenter exists in compounds of Formula (I). Accordingly, the present invention includes all possible stereoisomers and includes not only racemic compounds but the individual enantiomers as well. When a compound is desired as a single enantiomer, such may be obtained by stereospecific synthesis or by resolution of the final product or any convenient intermediate. Resolution of the final product, an intermediate, or a starting material may be effected by any suitable method known in the art. See, for example, Stereochemistry of Organic Compounds by E. L. Eliel, S. H. Wilen, and L. N. Mander (Wiley-Interscience, 1994), incorporated by reference with regard to stereochemistry.

Those skilled in the art will recognize that one method by which the imidazoindoles, as depicted in Formula (I), can be synthesized is from appropriately N-protected indolines. Directed deprotonation via an organolithium reagent like sec-butyl lithium in a suitable solvent like diethyl ether, typical but not limiting, followed by acylation with an alkyl chloroformate like methyl chloroformate generates the 7-carbonylated indoline. The protecting group can then be removed under acidic conditions like TFA, typical but not limiting, to give the NH indoline. Halogenation can be carried out with NIS or NBS, typical but not limiting, to provide the 5-halogenated indolines. The ester can then be hydrolyzed with lithium or sodium hydroxide in a suitable solvent like dioxane, typical but not limiting, generating the acid. The amide is then formed via reaction with an suitable amine in the presence of a base like DIPEA and a coupling reagent like HATU providing the amide, typical but not limiting. The imidazole is then synthesized using a suitable solvent like NMP in the presence of metal salt like copper iodide and imidazole under thermal conditions, typical but not limiting. The order of synthetic steps can also be Scheme 1

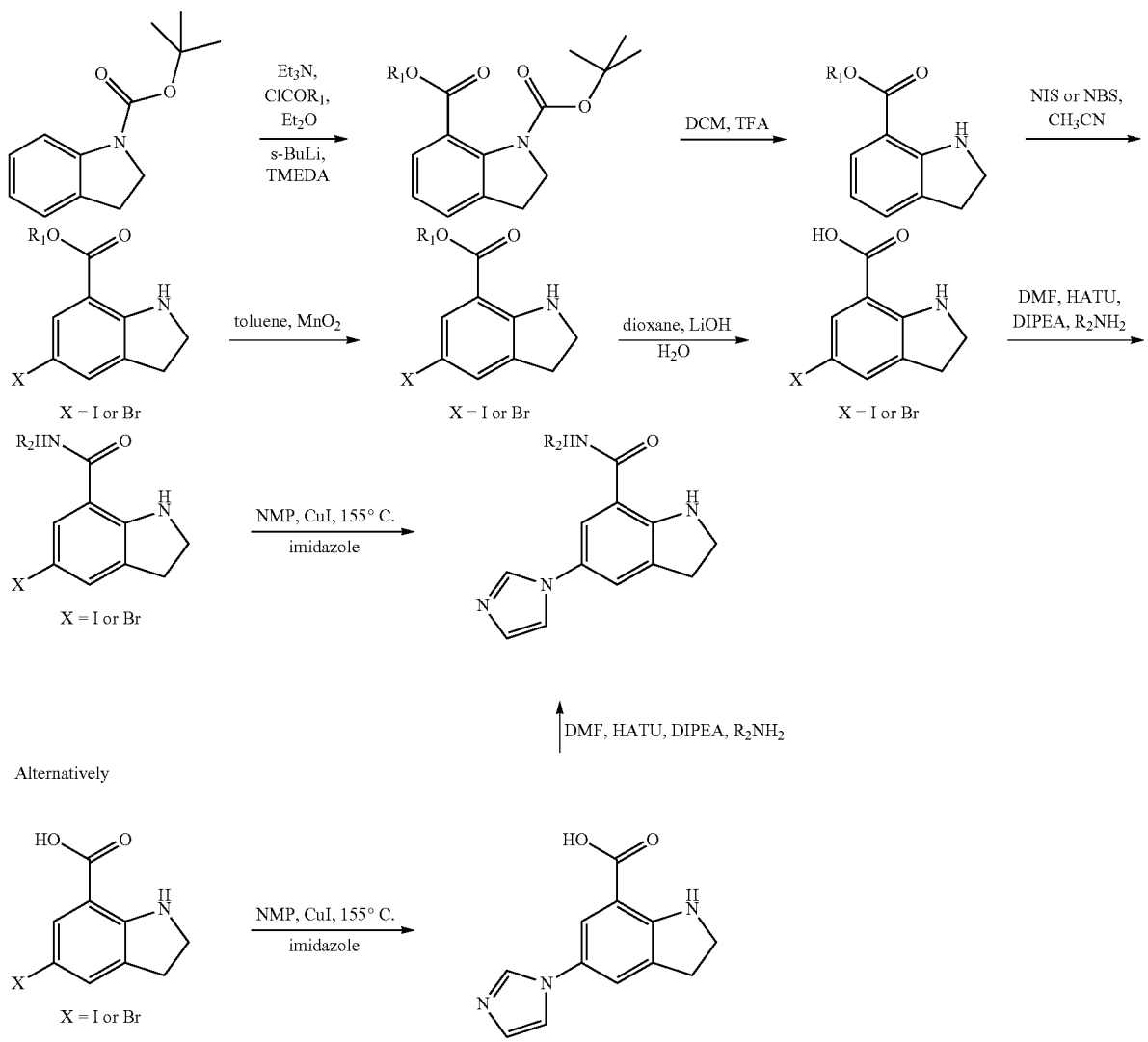

Alternatively switched such that the imidazole can be appended on after the hydrolysis reaction. (Scheme 1).

One skilled in the art will recognize that alternative synthetic routes exist to construct the indole core as depicted in Formula (I).

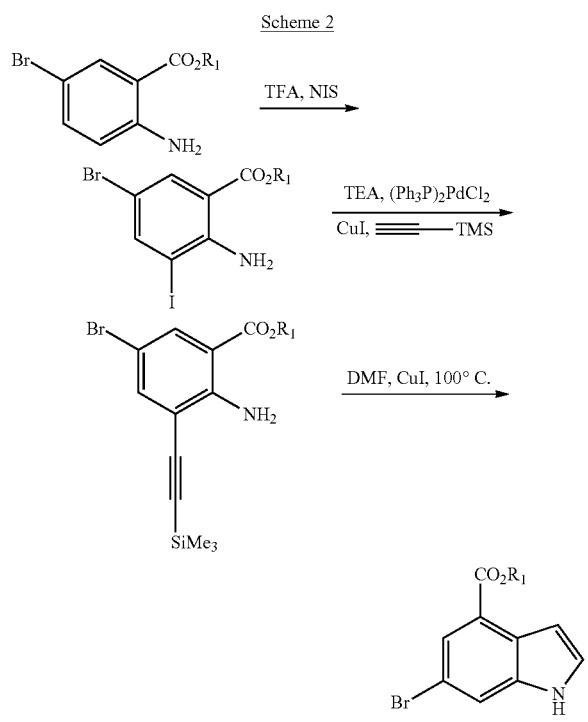

For example, reaction of a bromoanthranilic ester under halogenation conditions, like NIS under acidic conditions, typical but not limiting, provides the 3-iodo-5-bromoanthranilic ester. A metal catalyzed coupling reaction, like with palladium, with trimethylsilylacetylene in the presence of an organic base like triethylamine and copper iodide, typical conditions but not limiting, yields the desired indole. The indole can then be converted to the imidazoindole utilizing the aformentioned conditions (Scheme 2).

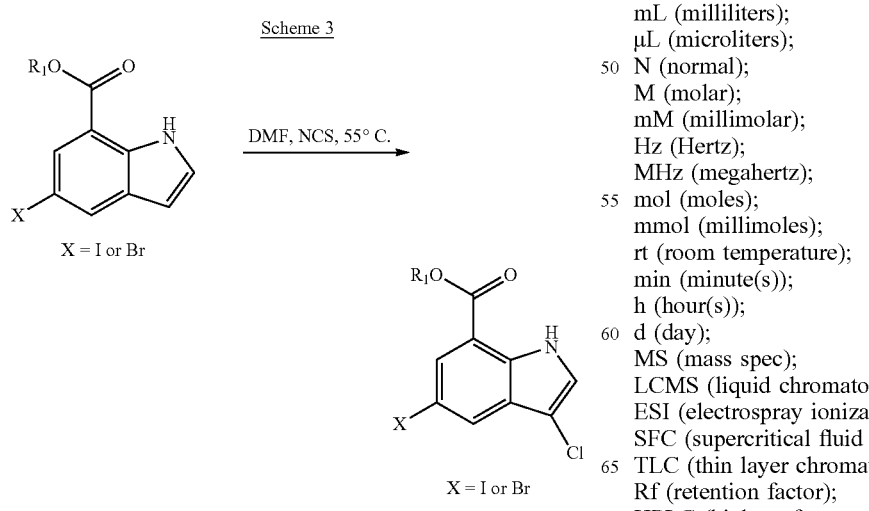

One skilled in the art will recognize that C3 substituted indoles can be synthesized from the aforementioned indole core. For example, treatment of either the 5-bromo or 5-iodoindole with NCS in DMF thermally generates the 3-chloroindole, typical but not limiting. Alternatively, reaction of the 5-bromo or 5-iodoindole with a ketone like acetone under Lewis acid conditions like TMSOTf followed by reduction with triethylsilane, typical but not limiting, provides the 3-alkyl substituted indoles which can be converted to the imidazoindoles via similar conditions as described previously (Scheme 3).

ABBREVIATIONS

As used herein the symbols and conventions used in these processes, schemes and examples are consistent with those used in the contemporary scientific literature, for example, the *Journal of the American Chemical Society* or the *Journal of Biological Chemistry*. Specifically, the following abbreviations may be used in the examples and throughout the specification:

g (grams);
mg (milligrams);
L (liters);
mL (milliliters);
μL (microliters);
N (normal);
M (molar);
mM (millimolar);
Hz (Hertz);
MHz (megahertz);
mol (moles);
mmol (millimoles);
rt (room temperature);
min (minute(s));
h (hour(s));
d (day);
MS (mass spec);
LCMS (liquid chromatography mass spec);
ESI (electrospray ionization);
SFC (supercritical fluid chromatography);
TLC (thin layer chromatography);
Rf (retention factor);
HPLC (high performance liquid chromatography);

UV (ultraviolet);
ee (enantiomeric excess);
VCD (vibrational circular dichoism);
PS (polymer supported);
$NH_4Cl$ (ammonium chloride);
THF (tetrahydrofuran);
MP-TSOH (macroporous polystyrene resin supported p-toluenesulfonic acid);
NaH (sodium hydride);
$NaBH_4$ (sodium borohydride);
$ZnI_2$ (zinc iodide);
TMSCN (trimethylsilylcyanide);
$Pd(PPh_3)_4$ (palladium tetrakistriphenyl phosphine);
LiOH (Lithium hydroxide);
$LiBH_4$ (lithium borohydride);
CuCN (copper cyanide);
$NH_4OH$ (ammonium hydroxide);
NBS (N-bromosuccinimide);
JLR (jacketed lab reactor);
$CH_2Cl_2$ or DCM (methylene chloride);
NaOH (sodium hydroxide);
TEA (triethylamine);
TFA (trifluoroacetic acid);
$CDCl_3$ (deuterated chloroform);
$CD_3OD$ (deuterated methanol);
$SiO_2$ (silica);
DMSO (dimethylsulfoxide);
EtOAc (EtOAc);
$Na_2SO_4$ (sodium sulfate);
HCl (hydrochloric acid);
$CHCl_3$ (chloroform);
DMF (N,N-dimethylformamide);
FA (formic acid);
$Cs_2CO_3$ (cesium carbonate);
Me (methyl);
Et (ethyl);
EtOH (ethanol);
MeOH (methanol);
t-Bu (tert-butyl);
$Et_2O$ (diethyl ether);
$N_2$ (nitrogen);
sat'd (saturated);
$MgSO_4$ (magnesium sulfate);
$NaHCO_3$ (sodium bicarbonate);
$Na_2CO_3$ (sodium carbonate);
$K_2CO_3$ (potassium carbonate);
TMEDA (tetramethyl ethylene diamine);
IPA (isopropyl alcohol);
NCS (N-chlorosuccinimide)
n-BuLi (n-butyllithium);
NMP (N-methyl-2-pyrrolidone);
HATU (O-(7-azabenzotriazole-1-yl)-N,N,N'N'-tetramethyluronium hexafluorophosphate);
DIEA (diisopropylethyl amine);
MCPBA (m-chloroperbenzoic acid);
MeCN or $CH_3CN$ (acetonitrile);
PTSA (p-toluene sulfonic acid);
DIAD (diisopropyl azodicarboxylate);
CsF (cesium fluoride);
$Zn(CN)_2$ (zinc cyanide);
$H_2SO_4$ (sulfuric acid);
TBME (t-butyl methyl ether);
dppf (1,1'-bis(diphenylphosphino)ferrocene);
$Pd_2(dba)_3$ (tris(dibenzylideneacetone)dipalladium(0)).
DMI (dimethylisosorbide)
atm (atmosphere);
Brett phos (2-(dicyclohexylphosphino)3,6-dimethoxy-2',4',6'-triisopropyl-1,1'-biphenyl;
DMEA (dimethylaminoethanol);
CuI (copper iodide);
$(Ph_3P)_2PdCl_2$ (bistriphenylphosphine palladium (II) chloride)
s-BuLi (sec-butyl lithium);
NIS (N-iodosuccinimide);
$MnO_2$ (manganese dioxide)

Unless otherwise indicated, all temperatures are expressed in ° C. (degrees Centigrade). All reactions conducted under an inert atmosphere at room temperature unless otherwise noted. Reagents employed without synthetic details are commercially available or made according to literature procedures. All compounds containing central or axial chirality are racemic unless otherwise indicated.

UPLC-MS analysis was conducted on a Waters Acquity UPLC system using a Waters BEH C18 column with dimensions 2.1×50 mm at 40° C. or on a Phenomenex Kinetex 1.7 um 2.1×50 mm XB-C18 100 A column at 40° C. A 0.5 µL partial loop with needle overfill injection was made, and UV detection was performed from 210 to 350 nm scanning at 40 Hz on a Waters Acquity PDA detector. A water+0.2% formic acid v/v (solvent A)/acetonitrile+0.15% formic acid v/v (solvent B) gradient was implemented with initial conditions 95/5% (A/B) to 1/99% over 1.10 min, and held until 1.5 min. A flow rate of 1 mL/min was used. Mass spectral analysis was performed on a Waters Acquity SQD with alternating positive/negative electrospray or atmospheric chemical ionization scanning from 125-1000 amu, with a scan time of 105 msec, and an interscan delay of 20 msec.

$^1$H NMR spectra were acquired on a Varian Inova 400 MHz or Bruker AS400 NMR spectrometer. The samples were dissolved in 99.9% deuterated Chloroform-d, DMSO-$d_6$, or Methanol-$d_4$, as indicated for each sample. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quin (quintet), m (multiplet), or b (broad).

Example 1: N-((1r,4r)-4-((2-Hydroxy-2-(trifluoromethyl)butyl)amino)cyclohexyl)-5-(1Himidazol-1-yl)-1H-indole-7-carboxamide A. 1-t-Butyl 7-methyl indoline-1,7-dicarboxylate A 1.4 M suspension of sec-butyllithium (200 mL, 280 mmol) was added over 25 min to a mechanically stirred suspension of t-butyl indoline-1-carboxylate (55.7 g, 254 mmol), TMEDA (100 mL, 663 mmol) and $Et_2O$ (1.1 L) at −75° C. The reaction mixture was stirred at −78° C. for 90 min. The thick suspension was added by cannula over 20 min to a mechanically stirred solution of methyl chloroformate (100 g, 1.06 mol) in $Et_2O$ (650 mL) maintaining the reaction temperature between −55 to −50° C. The suspension was stirred at −77° C. for 45 min, warmed to −20° C.

over 1.5 h and quenched by dropwise addition of MeOH (60 mL) over 20 min (temperature increased to 4° C.). The reaction mixture was stirred 20 min and poured into ice water (3 L). The layers were separated and the Et₂O phase was washed with 10% Na₂H₂PO₄ (1 L), dried over MgSO₄ and concentrated by rotovap chasing with heptane. The solid was triturated with heptane and filtered to afford 1-t-butyl 7-methyl indoline-1,7-dicarboxylate (47 g, 169 mmol) as a beige solid: 1H NMR (CDCl₃) δ: 7.50 (d, 1H, J=8 Hz), 7.28 (d, 1H, J=8 Hz), 7.02 (t, 1H, J=8 Hz), 4.12 (t, 2H, J=8 Hz), 3.84 (s, 3H), 3.08 (t, 2H, J=8 Hz), 1.51 (2, 9H). LCMS: (ES API) MH+=278

B. Methyl indoline-7-carboxylate trifluoroacetate

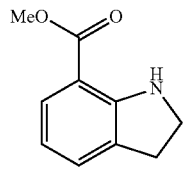

A solution of 1-t-butyl 7-methyl indoline-1,7-dicarboxylate (47 g, 169 mmol) in CH₂Cl₂ (100 mL) was cooled in an ice bath and TFA (100 mL) was added. The solution was stirred for 4 h with warming to rt and concentrated by rotovap chasing twice with CH₃CN and once with Et₂O. The resulting solid was triturated with Et₂O (35 mL) and the solids were collected by filtration. A second crop was obtained in a similar fashion from the mother liquors. The two batches were combined to afford the trifluoroacetate salt of methyl indoline-7-carboxylate as a beige solid (41 g, 141 mmol): 1H NMR (CDCl₃) δ: 8.52 (br s, 2H), 7.75 (d, 1H, J=8 Hz), 7.39 (d, 1H, J=7 Hz), 7.02 (br t, 1H, J=8 Hz), 3.91 (s, 3H), 3.90 (t, 2H, J=9 Hz), 3.22 (t, 2H, J=9 Hz). LCMS: (ES API) MH+=178.

C. Methyl 5-iodoindoline-7-carboxylate

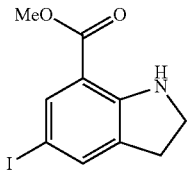 [SMILES: COC(=O)c1cc(I)cc2c1NCC2]

A stirred suspension of the trifluoroacetate salt of methyl indoline-7-carboxylate (41 g, 141 mmol) in CH₃CN (600 mL) was cooled to −17° C. and NIS (35 g, 156 mmol) was added portionwise over 20 min maintaining the reaction temperature below −10° C. The reaction mixture was stirred for 40 min at −12° C. and quenched by addition of 10% Na₂S₂O₃ (250 mL). The suspension was stirred for 15 min at 0° C. and the solids were collected by filtration. A second crop of crystals was obtained from the mother liquors and recrystallized from hot heptane. The combined solids were dried in a vacuum oven at 55° C. overnight to afford methyl 5-iodoindoline-7-carboxylate as a pale yellow solid (31 g, 102 mmol). 1H NMR (CDCl₃) δ: 8.52 (br s, 2H), 7.85 (s, 1H), 7.38 (s, 1H), 6.15 (br s, 1H), 3.86 (s, 3H), 3.73 (t, 2H, J=9 Hz), 3.05 (t, 2H, J=9 Hz). LCMS: (ES API) MH+=304.

D. Methyl 5-iodo-1H-indole-7-carboxylate

A stirred solution of methyl 5-iodoindoline-7-carboxylate (31 g, 102 mmol) in toluene (625 mL) was charged with MnO₂ (46 g, 529 mmol) and the reaction mixture was heated to 75° C. over 1 h and maintained at 75° C. for 1.5 h. The mixture was cooled to 30° C. and filtered rinsing with CH₂Cl₂. The filtrate was concentrated by rotovap to afford methyl 5-iodo-1H-indole-7-carboxylate as a pale yellow solid (27.5 g, 91 mmol). 1H NMR (DMSO-d₆) δ: 11.3 (br s, 1H), 8.22 (s, 1H), 7.42 (m, 1H), 6.54 (m, 1H), 3.94 (s, 3H). LCMS: (ES API) MH+=302.

E. 5-Iodo-1H-indole-7-carboxylic acid

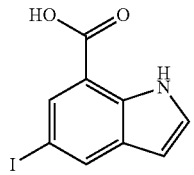 [SMILES: O=C(O)c1cc(I)cc2cc[nH]c12]

A 3 M solution of NaOH (60 mL, 180 mmol) was added to a stirred solution of methyl 5-iodo-1H-indole-7-carboxylate (7.5 g, 24.91 mmol) in MeOH (60 mL); THF (60 mL) was added and the reaction mixture was stirred for 1 h at rt. The reaction mixture was concentrated by rotovap and acidified with concentrated HCl (20 mL). The resulting solids were collected by filtration and dried in a vacuum oven at 45° C. to afford 5-iodo-1H-indole-7-carboxylic acid as a white solid (6.8 g, 23.69 mmol). 1H NMR (DMSO-d₆) δ: 11.3 (br s, 1H), 11.2 (s, 1H), 8.18 (s, 1H), 7.93 (s, 1H), 7.37 (m, 1H), 6.51 (m, 1H). LCMS: (ES API) MH−=286.

F. 2-(Aminomethyl)-1,1,1-trifluorobutan-2-ol hydrochloride

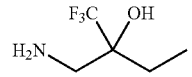

To a diethyl ether (5 mL) solution of 2-hydroxy-2-(trifluoromethyl)butanenitrile (500 mg, 3.27 mmol) at 0° C. under N₂, LiAlH (7.18 mL, 7.18 mmol) (1.0 M solution in THF) was added slowly. The resulting mixture was then stirred at rt over the weekend. The mixture was quenched with 0.5 mL of water at 0° C., then 0.5 mL 15% NaOH was added followed by 2.5 mL water. The mixture was stirred for 1.5 h then was filtered and washed with plenty of ether. After that, 2 mL of a 4.0 N HCl solution in dioxane was slowly added and stirred for 30 min. The solvents were removed in vacuo to afford 2-(aminomethyl)-1,1,1-trifluorobutan-2-ol hydrochloride (530 mg, 2.74 mmol) as a white solid. 1H NMR (DMSO-d$_6$) δ: 8.14 (br. s., 3H), 6.76 (br. s., 1H), 3.04 (m, 2H), 1.78 (q, J=7.53 Hz, 2H), 0.94 (t, J=7.40 Hz, 3H). LCMS: (ES API) MH+=158 (ELSD).

G. Benzyl (4-((2-hydroxy-2-(trifluoromethyl)butyl)amino)cyclohexyl)carbamate

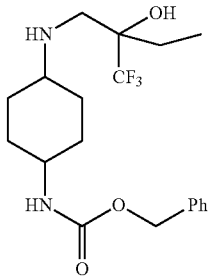 [SMILES: CCC(O)(CNC1CCC(NC(=O)OCc2ccccc2)CC1)C(F)(F)F]

To a 1,2-DCE (80 mL) mixture of 2-(aminomethyl)-1,1,1-trifluorobutan-2-ol hydrochloride (1.72 g, 8.90 mmol) and benzyl (4-oxocyclohexyl)carbamate (2.0 g, 8.09 mmol), 4 A molecular sieves (8.0 g) and Et$_3$N (1.35 ml, 9.71 mmol) were added. The resulting mixture was stirred for 2 h at rt at which time sodium triacetoxyborohydride (2.06 g, 9.71 mmol) was added followed by a few drops of acetic acid. The mixture was stirred overnight then filtered through celite. The filtrate was taken up in CH$_2$Cl$_2$ and washed with sat'd NaHCO$_3$ followed by drying over MgSO$_4$. The solvent was removed in vacuo and the residue purified on the ISCO Combiflash (0-15% MeOH/DCM with 1% NH$_4$OH) yielding a diastereomeric mixture of benzyl (4-((2-hydroxy-2-(trifluoromethyl)butyl)amino)cyclohexyl)carbamate (2.4 g, 6.18 mmol) as a white solid. 1H NMR (CDCl$_3$) δ: 7.29-7.44 (m, H), 5.11 (two singlets, 2H), [4.82 (m), 4.63 (m), together making 1H], [3.97 (m), 3.75 (m), together making 1H], 3.07 (m, 1H) 2.09-2.45 (m, 2H), 1.93-2.13 (m, 2H), 1.41-1.90 (m, 6H), 1.10-1.31 (m, 2H), 0.84-1.05 (m, 3H). LCMS: (ES API) M+H=389.

H. 2-(((4-Aminocyclohexyl)amino)methyl)-1,1,1-trifluorobutan-2-ol

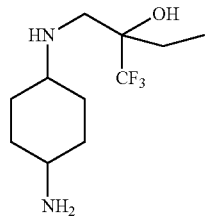 [SMILES: CCC(O)(CNC1CCC(N)CC1)C(F)(F)F]

To a methanol (30 ml) solution of benzyl (4-((2-hydroxy-2-(trifluoromethyl)butyl)amino)cyclohexyl)carbamate (2.4 g, 6.18 mmol), Pd/C (0.986 g, 0.927 mmol, 10% on carbon) was added. The mixture was degassed under N$_2$ and then stirred under H$_2$ balloon overnight. The mixture was filtered through celite and the filtrate concentrated in vacuo to afford 2-(((4-aminocyclohexyl)amino)methyl)-1,1,1-trifluorobutan-2-ol (1.85 g, 7.28 mmol) as a white solid tainted with a trace amount of Pd. 1H NMR (METHANOL-d$_4$) δ: 2.33 (m, 1H), 2.21 (m, 1H) 1.79-2.15 (m, 6H), 1.44-1.75 (m, 4H), 1.10 (d, J=7.03 Hz, 3H). LCMS: (ES API) MH+=255 (ELSD).

I. N-(4-((2-Hydroxy-2-(trifluoromethyl)butyl)amino)cyclohexyl)-5-iodo-1H-indole-7-carboxamide

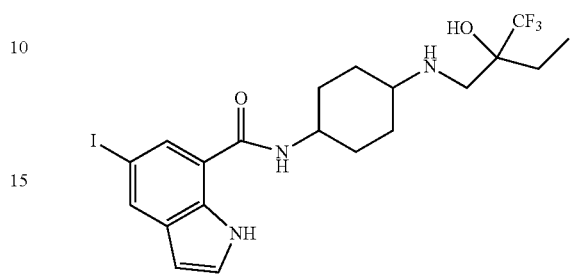

To a DMF (10 mL) solution of 5-iodo-1H-indole-7-carboxylic acid (400 mg, 1.39 mmol) was added HATU (636 mg, 1.67 mmol) followed by Hunig's base (0.487 mL, 2.79 mmol). The resulting mixture was stirred for 15 min before 2-(((4-aminocyclohexyl)amino)methyl)-1,1,1-trifluorobutan-2-ol (532 mg, 2.09 mmol) was added. This reaction mixture was stirred overnight at which time the reaction was quenched by adding sat'd NaHCO$_3$ solution followed by water. After diluting with DCM, the two phases were partitioned, and the aqueous was extracted with DCM. The combined organics were washed with water and brine then dried over MgSO$_4$. Upon filtration, the filtrate was concentrated in vacuo to afford the crude material as a cis/trans mixture that was carried to the next step without purification. 1H NMR (CDCl$_3$) δ: 10.2 (br. s., 1H) 8.04, 8.13 (2 singlets, 1H), 8.00 (m, 1H), 7.54-7.65 (2 sets of m, 1H) 7.19-7.29 (m, 2H) 6.17-6.51 (m, 2H), 3.06 (m, 1H), 2.40-2.52 (m, 2H), 1.50-2.15 (m, 8H), 1.20-1.33 (m, 2H), 0.88-1.01 (m, 3H). LCMS: (ES API) MH+=524.

J. N-((1r,4r)-4-((2-hydroxy-2-(trifluoromethyl)butyl)amino)cyclohexyl)-5-(1Himidazol-1-yl)-1H-indole-7-carboxamide and N-((1s,4S)-4-((2-hydroxy-2-(trifluoromethyl)butyl)amino)cyclohexyl)-5-(1Himidazol-1-yl)-1H-indole-7-carboxamide

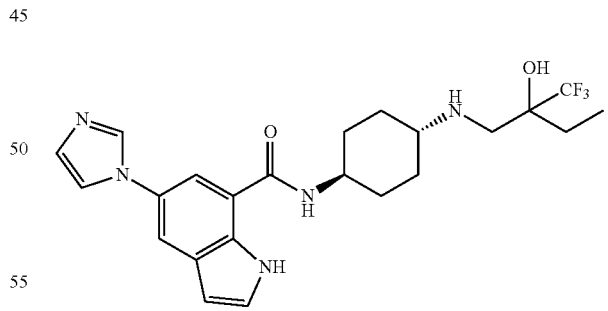

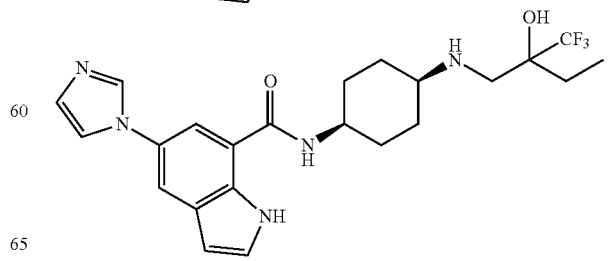

A NMP solution (12 mL) containing N-(4-((2-hydroxy-2-(trifluoromethyl)butyl)amino)cyclohexyl)-5-iodo-1H-indole-7-carboxamide (695 mg, 1.33 mmol), copper(I) iodide (25.3 mg, 0.13 mmol) and imidazole (226 mg, 3.32 mmol) was heated to 155° C. for 8 h. The dark heterogeneous solution was filtered 2× to remove solids and the amber liquid directly purified on the Agilent semi-prep HPLC (20-95% ACN/0.1% NH$_4$OH/H$_2$O) using a XBridge 30×150 mm C18 column. The fractions containing desired product were concentrated yielding N-((1r,4r)-4-((2-hydroxy-2-(trifluoromethyl)butyl)amino)cyclohexyl)-5-(1H-imidazol-1-yl)-1H-indole-7-carboxamide (40 mg, 0.07 mmol) as a brown solid and N-((1s,4s)-4-((2-hydroxy-2-(trifluoromethyl)butyl)amino)cyclohexyl)-5-(1H-imidazol-1-yl)-1H-indole-7-carboxamide (51 mg, 0.10 mmol) also as a brown solid. Trans: 1H NMR (MeOH-d$_4$) δ: 8.09 (br. s., 1H), 7.87 (s, 1H), 7.75 (s, 1H), 7.56 (br. s., 1H), 7.44 (d, J=2.93 Hz, 1H), 7.13 (br. s., 1H), 6.59 (d, J=3.12 Hz, 1H), 3.93 (t, J=11.5 Hz, 1H), 2.87 (d, J=12.9 Hz, 1H), 2.71 (d, J=12.9 Hz, 1H), 2.37-2.50 (m, 1H), 2.02 (t, J=10.6 Hz, 4H), 1.61-1.82 (m, 2H), 1.37-1.55 (m, 2H), 1.18-1.35 (m, 2H), 0.94 (t, J=7.42 Hz, 3H). LCMS (ES API) MH+=464. Cis: 1H NMR (MeOH-d$_4$) δ: 8.09 (br. s., 1H), 7.86 (d, J=1.37 Hz, 1H), 7.78 (s, 1H), 7.57 (br. s., 1H), 7.44 (d, J=3.12 Hz, 1H), 7.13 (br. s., 1H), 6.59 (d, J=2.93 Hz, 1H), 4.05 (t, J=8.20 Hz, 1H), 2.85 (d, J=12.9 Hz, 1H), 2.61-2.75 (m, 2H), 1.52-1.96 (m, 10H), 0.95 (t, J=7.42 Hz, 3H). LCMS (ES API) MH+=464.

Example 2: 5-(1H-Imidazol-1-yl)-N-((1R,4r)-4-(((R)-1,1,1-trifluoro-3-hydroxy-2-methylpropan-2-yl)amino)cyclohexyl)-1H-indole-7-carboxamide A. 5-(1H-Imidazol-1-yl)-1H-indole-7-carboxylic acid

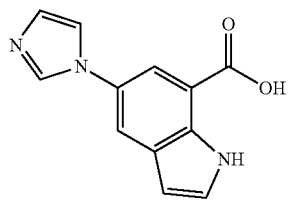 [SMILES: O=C(O)c1cc(-n2ccnc2)cc2cc[nH]c12]

5-Iodo-1H-indole-7-carboxylic acid (1.5 g, 5.23 mmol), imidazole (1.067 g, 15.7 mmol), copper(I) iodide (0.100 g, 0.523 mmol), and potassium carbonate (2.167 g, 15.7 mmol) were placed in a thick-walled glass tube and NMP (15 mL) was added. The resulting reaction mixture was heated at 160° C. for 20 h. The reaction was cooled to rt and diluted with 20 mL of MeOH and filtered through a pad of celite, rinsing with MeOH. Removal of the MeOH and NMP under vacuum afforded a dark oil. The crude material was then purified by reverse phase preparative HPLC (Agilent semi-prep HPLC, (5-60% ACN/0.1% NH$_4$OH/H$_2$O) using a XBridge 30×150 mm C18 column) to afford, after removal of solvents under vacuum, 5-(1H-imidazol-1-yl)-1H-indole-7-carboxylic acid as a dark brown solid. 1H NMR (DMSO-d$_6$) δ: 11.2 (s, br, 1H), 8.06 (s, 1H), 7.63 (m, 3H), 7.37 (s, br, 1H), 7.07 (s, 1H), 6.43 (m, 1H); LCMS (ES API) MH+=228.

B. (R)—N,N-Dibenzyl-3-methyl-3-(trifluoromethyl)-1-oxa-4-azaspiro[4.5]decan-8-amine

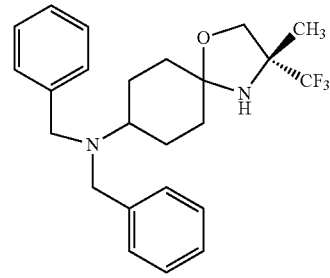 [SMILES: C[C@]1(C(F)(F)F)COC2(CCC(N(Cc3ccccc3)Cc3ccccc3)CC2)N1]

1.00 g (5.57 mmol) of the HCl salt of (R)-2-amino-3,3,3-trifluoro-2-methylpropan-1-ol (prepared by the method of Simon, J. et. al., *Organic Letters* 2012, 604-607) was placed in a sealed tube and slurried with 2 mL of 1,4-dioxane and 10 mL of toluene. Triethylamine (0.854 mL, 6.13 mmol) was added, followed by 4-(dibenzylamino)cyclohexanone (1.389 g, 4.73 mmol) and p-TsOH (0.212 g, 1.114 mmol). Activated 4 Å molecular sieves were added, and the reaction mixture was heated to 115° C. for 26 h. The reaction was cooled to rt, the sieves were filtered off, and the solvents were removed under vacuum. The crude reaction mixture was purified directly without a workup via silica gel chromatography (ISCO Combiflash Rf, 40 g silica gel column, SS: 0-50% EtOAc in hexanes gradient elution, 15 min run time) to afford (R)—N,N-dibenzyl-3-methyl-3-(trifluoromethyl)-1-oxa-4-azaspiro[4.5]decan-8-amine as an inseparable mixture of diastereomers. 1H NMR (CDCl$_3$) δ: 7.34 (m, 4H), 7.25 (m, 4H), 7.18 (m, 2H), 4.07 (m, 1H), 3.64 (m, 2H), 2.53 (m, 1H), 1.98-1.82 (m, 2H), 1.77-1.48 (m, 9H), 1.39 (m, 3H), 1.26 (m, 1H); LCMS (ES API) MH+=419.

C. (R)-2-(((1r,4R)-4-(Dibenzylamino)cyclohexyl)amino)-3,3,3-trifluoro-2-methylpropan-1-ol

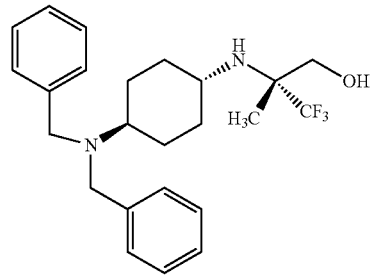 [SMILES: C[C@](CO)(N[C@H]1CC[C@H](N(Cc2ccccc2)Cc2ccccc2)CC1)C(F)(F)F]

(R)—N,N-Dibenzyl-3-methyl-3-(trifluoromethyl)-1-oxa-4-azaspiro[4.5]decan-8-amine (1.07 g, 2.56 mmol) was dissolved in 20 mL anhydrous THF. Lithium aluminum hydride (7.67 mL, 7.67 mmol) was added and the resulting solution was stirred at rt for 18 h. The reaction was then quenched by adding 290 μL of water, followed by 290 μL of 15% NaOH and then 870 μL of water. The crude reaction was stirred 5 min then filtered to remove the aluminum salts. The filtrate was concentrated under vacuum to afford a light yellow oil. The crude material was purified via silica gel chromatography (ISCO Combiflash Rf, 24 g silica gel column, 10-50% EtOAc/hexanes) to afford the cis isomer (R)-2-(((1s,4S)-4-

(dibenzylamino)cyclohexyl)amino)-3,3,3-trifluoro-2-methylpropan-1-ol and the trans isomer (R)-2-(((1r,4R)-4-(dibenzylamino)cyclohexyl)amino)-3,3,3-trifluoro-2-methylpropan-1-ol as white solids. Trans isomer: 1H NMR (CDCl₃) δ: 7.38-7.19 (m, 10H), 3.61 (s, 4H), 3.49 (m, 1H), 3.41 (m, 1H), 2.66 (t, 1H, J=11.1), 2.47 (m, 2H), 1.88 (m, 4H), 1.56-1.36 (m, 3H), 1.27 (s, 3H), 1.06 (m, 2H); LCMS (ES API) MH+=421.

D. (R)-2-(((1r,4R)-4-aminocyclohexyl)amino)-3,3,3-trifluoro-2-methylpropan-1-ol

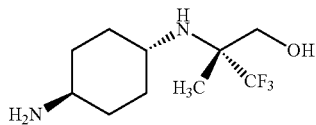

(R)-2-(((1r,4R)-4-(Dibenzylamino)cyclohexyl)amino)-3,3,3-trifluoro-2-methylpropan-1-ol (675 mg, 1.605 mmol) was dissolved in 5 mL of absolute EtOH and placed in a thick-walled glass tube. Pearlman's catalyst (113 mg, 0.161 mmol) was added. The reaction vessel was evacuated and flushed with nitrogen 3 times, then pressurized with H₂ to 40 psi, and stirred at rt for 16 h. The reaction mixture was filtered to remove the catalyst, rinsing with EtOAc, and the solvents were removed under vacuum to afford (R)-2-(((1r,4R)-4-aminocyclohexyl)amino)-3,3,3-trifluoro-2-methylpropan-1-ol as a white solid. 1H NMR (CDCl₃) δ: 3.51 (m, 1H), 3.42 (m, 1H), 2.72 (m, 1H), 1.88 (m, 5H), 1.69-1.49 (m, 5H), 1.28-1.15 (m, 5H); LCMS (ES API) MH+=241.

E. 5-(1H-Imidazol-1-yl)-N-((1R,4r)-4-(((R)-1,1,1-trifluoro-3-hydroxy-2-methylpropan-2-yl)amino)cyclohexyl)-1H-indole-7-carboxamide

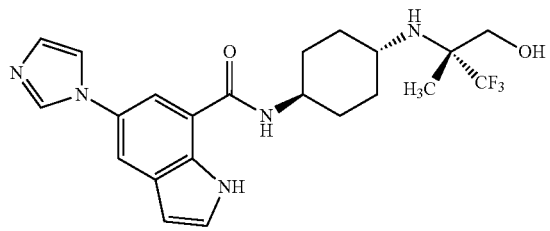 [SMILES: C[C@](CO)(N[C@H]1CC[C@H](NC(=O)c2cc(-n3ccnc3)cc3cc[nH]c23)CC1)C(F)(F)F]

5-(1H-Imidazol-1-yl)-1H-indole-7-carboxylic acid (72 mg, 0.317 mmol) was dissolved in a mixture of 2 mL of anhydrous DMF and 1 mL of NMP. Triethylamine (0.132 mL, 0.951 mmol) was added, followed by HATU (133 mg, 0.349 mmol). The reaction mixture was stirred at rt for 10 min, then (R)-2-(((1r,4R)-4-aminocyclohexyl)amino)-3,3,3-trifluoro-2-methylpropan-1-ol (80 mg, 0.333 mmol) was added as a solid. The resulting reaction mixture was stirred at rt for 2 h. The reaction mixture was purified directly without a workup by reverse phase preparative HPLC (Agilent semi-prep HPLC, (20-95% ACN/0.1% NH₄OH/H₂O) using an XBridge 30×150 mm C18 column) to afford, after removal of solvents under vacuum, 5-(1H-imidazol-1-yl)-N-((1R,4r)-4-(((R)-1,1,1-trifluoro-3-hydroxy-2-methylpropan-2-yl) amino)cyclohexyl)-1H-indole-7-carboxamide as a white solid. 1H NMR (DMSO-d₆) δ: 11.3 (s, br, 1H), 8.34 (d, 1H, J=7.8 Hz), 8.15 (s, 1H), 7.90 (d, 1H, J=1.4 Hz), 7.84 (d, 1H, J=1.4 Hz), 7.68 (s, 1H), 7.42 (s, br, 1H), 7.09 (s, 1H), 6.52 (s, br, 1H), 5.06 (s, br, 1H), 3.79 (m, 1H), 3.41 (m, 2H), 2.63 (m, 1H), 1.86 (m, 5H), 1.40 (q, 2H, J=12.4), 1.18 (m, 5H); LCMS (ES API) MH+=450.

Example 3: N-((1r,4r)-4-(2-Hydroxy-2-methylpropoxy)cyclohexyl)-5-(1H-imidazol-1-yl)-3-isopropyl-1H-indole-7-carboxamide A. Methyl 5-bromo-3-isopropyl-1H-indole-7-carboxylate

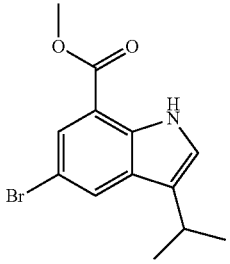 [SMILES: COC(=O)c1cc(Br)cc2c(C(C)C)c[nH]c12]

Propan-2-one (300 mg, 5.17 mmol) was dissolved in DCM (10 mL) at 0° C. Trimethylsilyl trifluoromethanesulfonate (525 mg, 2.361 mmol) was then added dropwise over 1 min. The reaction mixture was stirred 3 min then methyl 5-bromo-1H-indole-7-carboxylate (example 4 step C) (500 mg, 1.968 mmol) was added in one portion. The mixture was stirred at 0° C. for 30 min then triethylsilane (0.654 mL, 3.94 mmol) was added dropwise and the reaction was allowed to stir and warm to rt overnight. The reaction mixture was diluted with ethyl acetate and the subsequent organics were washed with saturated sodium bicarbonate. The organics were separated from the aqueous mixture and directly concentrated onto silica gel. The pre-absorbed sample was then purified on an ISCO Combiflash, eluting with 0-50% EtOAc/hexanes. The desired product peak was collected and concentrated to dryness. It was determined by NMR and LCMS that the product was approximately 70% pure methyl 5-bromo-3-isopropyl-1H-indole-7-carboxylate (264 mg, 0.891 mmol). 1H NMR (DMSO-d₆) δ: 11.1 (br. s., 1H), 8.04 (d, J=1.6 Hz, 1H), 7.79 (d, J=1.8 Hz, 1H), 7.21 (d, J=2.3 Hz, 1H), 3.94 (s, 3H), 3.17 (quin, J=6.8 Hz, 1H), 1.29 (d, J=6.8 Hz, 6H).

B. 5-Bromo-3-isopropyl-1H-indole-7-carboxylic acid

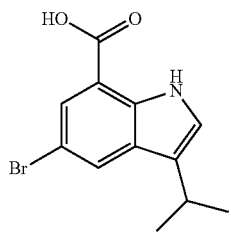 [SMILES: CC(C)c1c[nH]c2c(C(=O)O)cc(Br)cc12]

Methyl 5-bromo-3-isopropyl-1H-indole-7-carboxylate (264 mg, 0.891 mmol) was combined with lithium hydroxide hydrate (41.1 mg, 0.981 mmol), water (1.5 mL) and 1,4-dioxane (6 mL) with stirring. The mixture was heated to 50° C. for 4 h then at rt overnight. The reaction was concentrated down to dryness and further dried on high vacuum overnight. The crude isolated product was determined to be approximately 70% pure which resulted from the use of impure starting material for the reaction providing 5-bromo-3-isopropyl-1H-indole-7-carboxylic acid lithium salt (258 mg, 0.624 mmol). LCMS (ES API) MH−=280, 282.

C. 5-Bromo-N-((1r,4r)-4-(2-hydroxy-2-methylpropoxy)cyclohexyl)-3-isopropyl-1H-indole-7-carboxamide

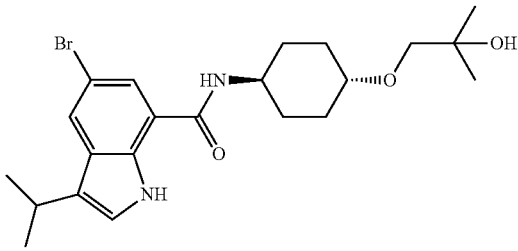 [SMILES: CC(C)c1c[nH]c2c(C(=O)N[C@H]3CC[C@H](OCC(C)(C)O)CC3)cc(Br)cc12]

5-Bromo-3-isopropyl-1H-indole-7-carboxylic acid (100 mg, 0.354 mmol) was combined with HATU (148 mg, 0.390 mmol) and DIEA (~50 mg) in DMF (3 mL). The reaction was stirred for 10 min then 1-(((1r,4r)-4-aminocyclohexyl)oxy)-2-methylpropan-2-ol (73.0 mg, 0.390 mmol) and ~51 mg DIEA were added to the stirring mixture. This was allowed to stir overnight at rt. The crude reaction was concentrated to dryness on the V10 evaporator to remove the DMF. The reaction mixture was diluted with DCM and the subsequent organics were washed with saturated sodium bicarbonate and brine. The organics were separated from the aqueous, treated with sodium sulfate, filtered and concentrated to dryness to give the desired product with impurities providing 5-bromo-N-((1r,4r)-4-(2-hydroxy-2-methylpropoxy)cyclohexyl)-3-isopropyl-1H-indole-7-carboxamide (80 mg, 0.177 mmol), which was then used directly in the next reaction. 1H NMR (DMSO-$d_6$) δ: 11.0 (br. s., 1H), 8.40 (d, J=7.8 Hz, 1H), 7.87 (d, J=1.4 Hz, 1H), 7.80 (d, J=1.4 Hz, 1H), 7.12 (d, J=2.1 Hz, 1H), 4.23 (s, 1H), 3.77-3.87 (m, 1H), 3.05-3.29 (m, 4H), 2.04 (d, J=12.7 Hz, 2H), 1.89 (d, J=10.0 Hz, 2H), 1.33-1.49 (m, 2H), 1.14-1.31 (m, 8H), 1.02-1.10 (m, 6H). LCMS (ES API) MH+=451, 453.

D. N-((1r,4r)-4-(2-Hydroxy-2-methylpropoxy)cyclohexyl)-5-(1H-imidazol-1-yl-3-isopropyl-1H-indole-7-carboxamide

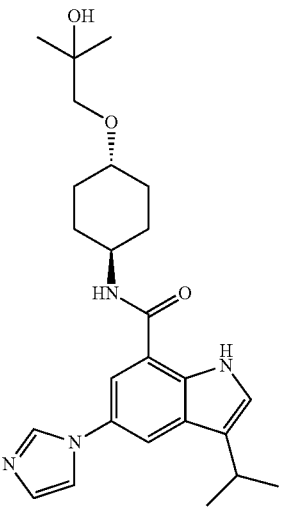 [SMILES: CC(C)c1c[nH]c2c(C(=O)N[C@H]3CC[C@H](OCC(C)(C)O)CC3)cc(-n3ccnc3)cc12]

5-Bromo-N-((1r,4r)-4-(2-hydroxy-2-methylpropoxy)cyclohexyl)-3-isopropyl-1H-indole-7-carboxamide (80 mg, 0.177 mmol) was placed in a microwave reaction vessel with 1H-imidazole (48.3 mg, 0.709 mmol), $K_2CO_3$ (49.0 mg, 0.354 mmol), copper(I) iodide (6.75 mg, 0.035 mmol) and NMP (2 mL). This mixture was heated at 120° C. for 4 h in the microwave, then at 160° C. for an additional 12 h. The reaction was then filtered through a fine PTFE filter before purification on a basic (1% $NH_4OH$ in $H_2O$): $CH_3CN$ Agilent 20-95% gradient. The desired product peak was collected and concentrated to dryness. Ethyl ether was then added and solids that persisted were filtered off to give the desired product N-((1r,4r)-4-(2-hydroxy-2-methylpropoxy)cyclohexyl)-5-(1H-imidazol-1-yl-3-isopropyl-1H-indole-7-carboxamide (18 mg, 0.039 mmol). 1H NMR (DMSO-$d_6$) δ: 11.0 (br. s., 1H), 8.36 (d, J=7.6 Hz, 1H), 8.19 (s, 1H), 7.89 (d, J=1.6 Hz, 1H), 7.83 (d, J=1.6 Hz, 1H), 7.73 (s, 1H), 7.18 (d, J=2.0 Hz, 1H), 7.12 (s, 1H), 4.23 (s, 1H), 3.81-3.91 (m, 1H), 3.19 (s, 2H), 3.14-3.28 (m, 2H), 2.05 (d, J=10.2 Hz, 2H), 1.93 (d, J=11.3 Hz, 2H), 1.35-1.48 (m, 2H), 1.31 (d, J=6.8 Hz, 6H), 1.21-1.34 (m, 2H), 1.07 (s, 6H), LCMS (ES API) MH+=439.

Example 4: 5-(1H-Imidazol-1-yl)-N-((1s,4s)-4-(methylcarbamoyl)cyclohexyl)-1H-indole-7-carboxamide

A. Methyl 2-amino-5-bromo-3-iodobenzoate

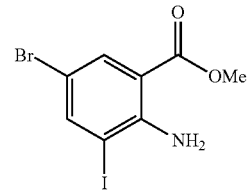 [SMILES: COC(=O)c1cc(Br)cc(I)c1N]

To a stirring of solution of methyl 2-amino-5-bromobenzoate (5 g, 21.73 mmol) in TFA (20 mL, 260 mmol) is added NIS (4.99 g, 22.17 mmol) in one portion. After 1 h, the reaction mixture is concentrated under reduced pressure. The residue is dissolved in EtOAc and washed sequentially with saturated $Na_2CO_3$ solution (2×), 10% aq. sodium dithionite (2×) and brine (1×), dried over $Na_2SO_4$, filtered and concentrated to give the title compound (7.47 g, 18.89 mmol, 90% purity) as a dark brown solid. LCMS (ES API) MH+=356 & 358 for Br isotopes.

B. Methyl 2-amino-5-bromo-3-((trimethylsilyl)ethynyl)benzoate

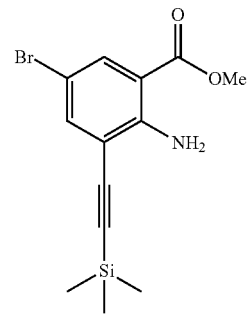 [SMILES: COC(=O)c1cc(Br)cc(C#C[Si](C)(C)C)c1N]

To a solution of methyl 2-amino-5-bromo-3-iodobenzoate (7.47 g, 20.99 mmol) in TEA (40 mL, 287 mmol) is added Pd(PPh$_3$)$_2$Cl$_2$ (0.884 g, 1.259 mmol), and copper(I) iodide (0.240 g, 1.259 mmol). The mixture is stirred under N$_2$ for about 5 min, and then trimethylsilylacetylene (3.83 mL, 27.3 mmol) is added. The mixture is stirred at rt for 1 h. The reaction is followed by LCMS (only 6% product after 1 h). The mixture is then transferred to a pressure tube and additional Pd(PPh$_3$)$_2$Cl$_2$ (0.14 g, 0.199 mmol) and copper(I) iodide (0.036 g, 0.189 mmol) are added. The mixture is purged with N$_2$ for 1 min, and then it is heated at 60° C. for 2 h (LCMS shows 54% mono-alkyne and 35% bis-alkyne). The reaction mixture is concentrated under reduced pressure. The residue is taken up in CH$_2$Cl$_2$ and filtered through a plug of Celite. The Celite plug is washed with CH$_2$Cl$_2$. The filtrate is washed with water (2×) and brine (1×), dried over Na$_2$SO$_4$, filtered and concentrated. The residue is chromatographed over silica gel (120 g ISCO column) eluting with 0-5% EtOAc/hexane gradient to yield a mixture of methyl 2-amino-5-bromo-3-((trimethylsilyl)ethynyl)benzoate and methyl 2-amino-3,5-bis((trimethylsilyl)ethynyl)benzoate (4.2 to 1 ratio by 1H NMR). LCMS (ES API) MH+=326 & 328 for Br isotopes mono-alkyne product; and LCMS (ES API) MH+=344 bis-alkyne product.

C. Methyl 5-bromo-1H-indole-7-carboxylate

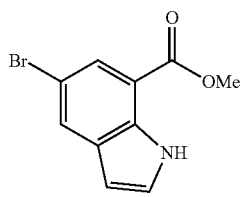 [SMILES: COC(=O)c1cc(Br)cc2cc[nH]c12]

A mixture of methyl 2-amino-5-bromo-3-((trimethylsilyl)ethynyl)benzoate (500 mg, 1.53 mmol; contaminated with ~20% of methyl 2-amino-3,5-bis((trimethylsilyl)ethynyl)benzoate) and 2 eq of CuI (584 mg, 3.07 mmol) in DMF (4 mL) is set under N$_2$ and heated in a sealed tube at 100° C. for 80 min. Upon cooling, the reaction mixture is diluted with Et$_2$O and filtered through a plug of Celite. The Celite plug is washed with Et$_2$O and EtOAc. The filtrate is concentrated under reduced pressure. The residue is chromatographed over silica gel eluting with 0-15% EtOAc-hexane gradient to give the title compound as a light yellow solid. LCMS (ES API) MH+=254 & 256 for Br isotopes.

D. 5-Bromo-1H-indole-7-carboxylic acid

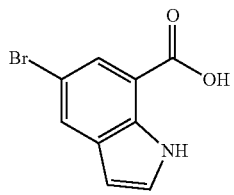 [SMILES: O=C(O)c1cc(Br)cc2cc[nH]c12]

To a solution of methyl 5-bromo-1H-indole-7-carboxylate (200 mg, 0.787 mmol) in 1:1 THF/MeOH (4 mL) is added a solution of NaOH (212 mg, 5.30 mmol) in water (2 mL). The homogenous solution is stirred at rt overnight. The reaction mixture is acidified slowly with 1.0 N HCl (~8 mL). A light yellow solid precipitated out which was collected by filtration, washed sequentially with water and hexane, and dried to give the title compound as a light yellow solid (183 mg, 0.724 mmol). LCMS (ES API) MH−=238 & 240 for Br isotopes.

E. 5-Bromo-N-((1s,4S)-4-(methylcarbamoyl)cyclohexyl)-1H-indole-7-carboxamide

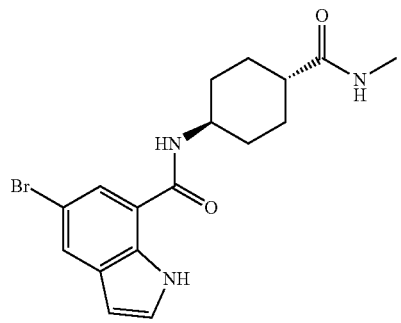 [SMILES: CNC(=O)[C@H]1CC[C@H](NC(=O)c2cc(Br)cc3cc[nH]c23)CC1]

To a solution of 5-bromo-1H-indole-7-carboxylic acid (182 mg, 0.758 mmol) in DMF (3 mL) is added DIEA (0.172 mL, 0.986 mmol) and HATU (346 mg, 0.910 mmol). After 1 min, (1r,4r)-4-amino-N-methylcyclohexanecarboxamide (142 mg, 0.910 mmol) is added, followed by DIEA (0.172 mL, 0.986 mmol). After ~30 min, the reaction mixture is slowly diluted with water (~10 mL), and a white solid precipitates out. After stirring for a few minutes, the solid is collected by filtration, washed sequentially with water and hexane and dried under high vacuum. The material is then chromatographed over silica gel (24 g ISCO column) to give the title compound as a white solid (210 mg, 0.516 mmol). LCMS (ES API) MH+=378 & 380 for Br isotopes.

F. 5-(1H-imidazol-1-yl)-N-((1s,4S)-4-(methylcarbamoyl)cyclohexyl)-1H-indole-7-carboxamide

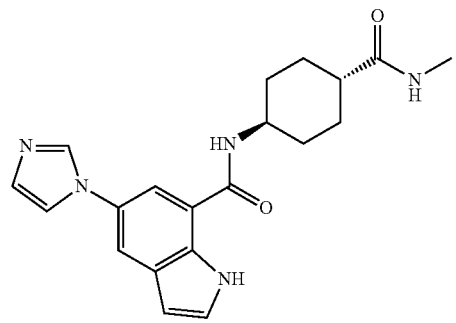 [SMILES: CNC(=O)[C@H]1CC[C@H](NC(=O)c2cc(-n3ccnc3)cc3cc[nH]c23)CC1]

A mixture of 5-bromo-N-((1s,4S)-4-(methylcarbamoyl) cyclohexyl)-1H-indole-7-carboxamide (60 mg, 0.159 mmol), 1H-imidazole (21.60 mg, 0.317 mmol), copper(I) iodide (3.02 mg, 0.016 mmol) and K$_2$CO$_3$ (43.8 mg, 0.317 mmol) in DMF (2 mL) is purged with N$_2$ for a few minutes, and then it is heated in a sealed tube at 150° C. for 19 h. (LCMS shows 42% conversion). Additional 1H-imidazole (21.60 mg, 0.317 mmol), copper(I) iodide (3.02 mg, 0.016 mmol) and K$_2$CO$_3$ (43.8 mg, 0.317 mmol) are added, reset under N₂ and heated at 150° C. in a sealed tube for another 15 h. Upon cooling, the reaction mixture is diluted with MeOH (~5 mL). The insoluble material is filtered off and washed with MeOH (~10 mL) and CH₂Cl₂ (~10 mL). The filtrate is concentrated down to the DMF phase. The residue is purified by preparative HPLC (Phenomenex Luna column; 5-50% MeCN/water with 0.1% NH₄OH). The fractions with product are concentrated to dryness to give a yellow solid. The material is further purified by silica gel chromatography (1 mm chromatotron plate) eluting with 0-10% MeOH/CH₂Cl₂. The product is then crystallized from CH₂Cl₂/hexane (plus a minimal amount of MeOH) to give the title compound as a light beige solid (29 mg, 0.077 mmol). 1 HNMR (DMSO-d₆) δ: 11.3 (s, NH), 8.41 (d, J=7.8 Hz, NH), 8.18 (s, 1H), 7.93 (d, J=1.8 Hz, 1H), 7.86 (d, J=1.8 Hz, 1H), 7.75-7.71 (m, 2H), 7.44 (t, J=2.7 Hz, 1H), 7.12 (s, 1H), 6.55 (t, J=2.4 Hz, 1H), 3.9-3.8 (m, 1H), 2.57 (d, J=4.5 Hz, 3H), 2.14-2.04 (m, 1H), 1.99-1.93 (m, 2H), 1.83-1.70 (m, 2H), 1.55-1.30 (m, 4H). LCMS (ES API) MH+=366.

Example 5: Synthesis of 5-(1H-imidazol-1-yl)-N-((1s,4s)-4-(2-methoxyethoxy)cyclohexyl)-1H-indole-7-carboxamide A. 5-Iodo-N-((1r,4r)-4-(2-methoxyethoxy)cyclohexyl)-1H-indole-7-carboxamide

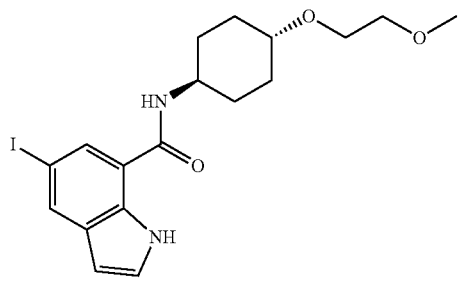 [SMILES: COCCO[C@H]1CC[C@H](NC(=O)c2cc(I)cc3cc[nH]c23)CC1]

To a solution of 5-iodo-1H-indole-7-carboxylic acid (270 mg, 0.941 mmol) in DMF (2 mL) is added DIEA (0.214 mL, 1.22 mmol) and HATU (429 mg, 1.129 mmol). After stirring for 1 min, a solution of (1r,4r)-4-(2-methoxyethoxy)cyclohexanamine (196 mg, 1.129 mmol) in DMF (0.5 mL) is added, followed by additional DIEA (0.214 mL, 1.223 mmol). After 1 h, the reaction mixture is diluted with EtOAc and washed with dilute K₂CO₃ solution. The organic phase is washed with dilute K₂CO₃ solution (1×) and with brine (1×), dried over Na₂SO₄, filtered and concentrated. The residue is chromatographed over silica gel (40 g ISCO column) eluting with 10-50% EtOAc/hexane gradient. The product is further purified by reverse phase HPLC (C18 Phenomenex Luna column; gradient: 10-100% MeCN/water with 0.1% TFA). The fractions with product are combined and concentrated down to the aqueous phase. The residue is diluted with EtOAc and neutralized with K₂CO₃ aqueous solution. The phases are separated. The organic phase is washed with brine, dried over Na₂SO₄, filtered and concentrated to give the title compound as a white solid (265 mg, 0.551 mmol). LCMS (ES API) MH+=443.

B. 5-(1H-Imidazol-1-yl)-N-((1s,4S)-4-(2-methoxyethoxy)cyclohexyl)-1H-indole-7-carboxamide

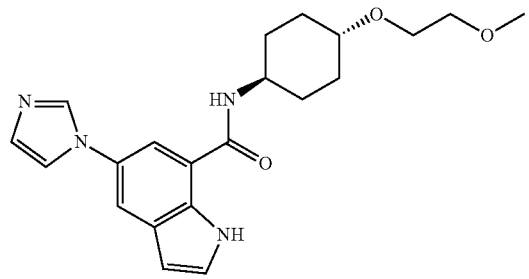 [SMILES: COCCO[C@H]1CC[C@H](NC(=O)c2cc(-n3ccnc3)cc3cc[nH]c23)CC1]

A mixture of 5-iodo-N-((1r,4r)-4-(2-methoxyethoxy)cyclohexyl)-1H-indole-7-carboxamide (60 mg, 0.136 mmol), 1H-imidazole (27.7 mg, 0.407 mmol), copper(I) iodide (2.58 mg, 0.014 mmol) and K₂CO₃ (56.2 mg, 0.407 mmol) in DMF (2 mL) is purged with N₂ for a few minutes, and then it is heated in a sealed tube at 150° C. for 19 h. (LCMS shows 44% product and 56% SM). Additional 2 eq each of 1H-imidazole (18.47 mg, 0.271 mmol) and K₂CO₃ (37.5 mg, 0.271 mmol) and a catalytic amount of copper(I) iodide (2.58 mg, 0.014 mmol) are added The mixture is heated for another 10 h and upon cooling, the reaction mixture is diluted with MeOH and filtered through a small plug of Celite. The solids are washed with MeOH and CH₂Cl2. The filtrate is concentrated to dryness. The residue is purified by reverse phase HPLC (C18 Phenomenex Luna column; gradient: 10-100% MeCN/water with 0.1% TFA). The fractions with product are combined and concentrated. The residue is partitioned between EtOAc and aqueous NaHCO₃ solution. The organic phase is washed with brine, dried over Na₂SO₄, filtered and concentrated. The residue is crystallized from CH₂Cl₂/hexane to give the title compound as a light yellow solid (24 mg, 0.060 mmol). 1H NMR (DMSO-d₆) δ: 11.3 (s, NH), 8.40 (d, J=7.6 Hz, NH), 8.18 (s, 1H), 7.93 (d, J=1.8 Hz, 1H), 7.86 (d, J=2.0 Hz, 1H), 7.72 (s, 1H), 7.45 (t, J=2.7 Hz, 1H), 7.12 (s, 1H), 6.55 (t, J=2.5 Hz, 1H), 3.91-3.82 (m, 1H), 3.56-3.53 (m, 2H), 3.44-3.42 (m, 2H), 3.32-3.20 (m, 1H), 3.25 (s, 3H), 2.08-2.0 (m, 2H), 1.97-1.90 (m, 2H), 1.45-1.35 (m, 2H), 1.30-1.20 (m, 2H). LCMS (ES API) MH+=383.

Example 6: N-((1r,4r)-4-(2-Hydroxy-2-methylpropoxy)cyclohexyl)-5-(1H-imidazol-1-yl)-1H-indole-7-carboxamide A. (1r,4r)-4-(Dibenzylamino)cyclohexanol

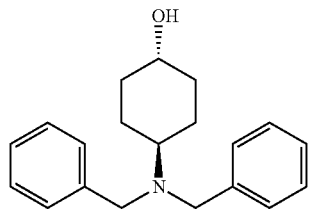 [SMILES: O[C@H]1CC[C@H](N(Cc2ccccc2)Cc2ccccc2)CC1]

To (1r,4r)-4-aminocyclohexanol hydrochloride (5.0 g, 33.0 mmol) and sodium bicarbonate (8.31 g, 99 mmol) stirring in EtOH (102 mL) was added benzyl bromide (7.8 mL, 65.6 mmol) before heating to 80° C. for 24 h. The reaction was filtered, warmed and concentrated under reduced pressure. The material was taken up in DCM and washed with 1.0 N aq. NaOH (2×). The combined aq. NaOH fractions were back extracted with DCM. The combined organics were washed with brine, dried over sodium sulfate, filtered and concentrated under reduced pressure. The residue was purified by silica gel chromatography eluting with a gradient from 15-45% EtOAc/hexanes yielding a white solid as (1r,4r)-4-(dibenzylamino)cyclohexanol (5.18 g, 17.5 mmol). 1H NMR (CDCl$_3$) δ: 1.14-1.28 (m, 2H), 1.30 (d, J=4.77 Hz, 1H), 1.38-1.52 (m, 2H), 1.91 (d, J=12.55 Hz, 2H), 2.00 (br. s., 1H), 2.53 (tt, J=11.7, 3.48 Hz, 1H), 3.50-3.59 (m, 1H), 3.62 (s, 4H), 7.18-7.25 (m, 2H), 7.27-7.32 (m, 4H), 7.33-7.38 (m, 4H). LCMS: (ESI) MH+=296.

B. tert-Butyl 2-(((1r,4r)-4-(dibenzylamino)cyclohexyl)oxy)acetate

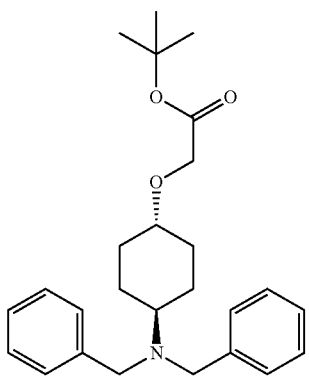 [SMILES: CC(C)(C)OC(=O)CO[C@H]1CC[C@H](N(Cc2ccccc2)Cc2ccccc2)CC1]

(1r,4r)-4-(Dibenzylamino)cyclohexanol (1.0 g, 3.4 mmol) and tert-butyl 2-bromoacetate (1.0 mL, 6.8 mmol) were stirring in DMF (5 mL) at 55° C. then a 60% dispersion in mineral of NaH (0.27 g, 6.8 mmol) was added portionwise over 1 h. The LCMS displayed some product and starting material, thus added more tert-butyl 2-bromoacetate (1.00 mL, 6.8 mmol) and 60% dispersion in mineral of NaH (0.27 g, 6.8 mmol) was added portion wise over 1 h. The reaction was allowed to stir at same temperature overnight before quenching with water. The reaction was poured into a separatory funnel, diluted with 1.0 N aq. NaOH and extracted with ethyl acetate (1×). The organic layer was washed with water (2×), followed by brine. The combined aq. fractions were extracted with ethyl acetate and the combined organics were dried over sodium sulfate, filtered and concentrated under reduced pressure. The residue was purified by silica gel chromatography via ISCO Combiflash eluting with a gradient from 2-15% (3:1 ratio of ethyl acetate:ethanol:hexanes). The fractions recovered were concentrated under reduced pressure to a colorless oil as tert-butyl 2-(((1r,4r)-4-(dibenzylamino)cyclohexyl)oxy)acetate (497 mg, 1.21 mmol). 1H NMR (CDCl$_3$) δ: 1.43-1.46 (m, 4H), 1.47 (s, 9H), 1.92 (d, J=12.3 Hz, 2H), 2.07-2.14 (m, 2H), 2.48-2.58 (m, 1H), 3.24-3.30 (m, 1H), 3.61 (s, 4H), 3.96 (s, 2H), 7.17-7.24 (m, 2H), 7.26-7.32 (m, 4H), 7.34-7.38 (m, 4H). LCMS: (ELSD) MH+=410.

C. 1-(((1r,4r)-4-(Dibenzylamino)cyclohexyl)oxy)-2-methylpropan-2-ol

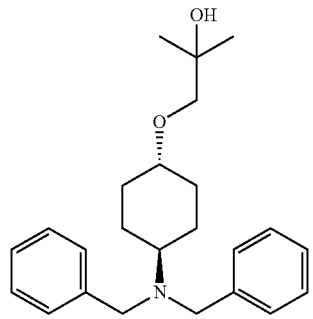 [SMILES: CC(C)(O)CO[C@H]1CC[C@H](N(Cc2ccccc2)Cc2ccccc2)CC1]

Tert-butyl 2-(((1r,4r)-4-(dibenzylamino)cyclohexyl)oxy) acetate (0.40 g, 0.977 mmol) was stirring in THF (2.5 mL) under nitrogen at 0° C. then a 3.0 M solution of methylmagnesium bromide (0.8 mL, 2.4 mmol) in diethyl ether was added. The reaction stirred at rt for 3 h then quenched with sat. aq. NH$_4$Cl (3 mL) and stirred at rt overnight. The reaction was poured into separatory funnel and diluted with ethyl acetate then washed with sat'd aq. sodium bicarbonate (1×), water (2×) and brine. The organics were dried over sodium sulfate, filtered and concentrated under reduced pressure. The residue was purified by silica gel chromatography via ISCO Combiflash eluting with a gradient from 5-15% (3:1 ratio of ethyl acetate:ethanol:hexanes) providing a colorless oil that solidified over time as 1-(((1r,4r)-4-(dibenzylamino)cyclohexyl)oxy)-2-methylpropan-2-ol (0.168 g, 0.457 mmol). 1H NMR (CDCl$_3$) δ: 1.09-1.22 (m, 8H), 1.33-1.47 (m, 2H), 1.88-1.97 (m, 2H), 2.04-2.11 (m, 2H), 2.53 (tt, J=11.7, 3.36 Hz, 1H), 3.19 (tt, J=11.0, 4.36 Hz, 1H), 3.24 (s, 2H), 3.61 (s, 4H), 7.18-7.24 (m, 2H), 7.26-7.33 (m, 4H), 7.34-7.39 (m, 4H). LCMS: (ELSD) MH+=368.

D. 1-(((1r,4r)-4-Aminocyclohexyl)oxy)-2-methylpropan-2-ol

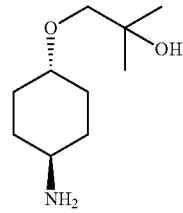

A mixture of 1-(((1r,4r)-4-(dibenzylamino)cyclohexyl) oxy)-2-methylpropan-2-ol (620 mg, 1.69 mmol) and palladium hydroxide on carbon (300 mg, 2.14 mmol) in EtOH (5 mL) is hydrogenated at 55 psi (Fisher-Porter apparatus) for 2 h. The reaction mixture is filtered through a plug of celite. The catalyst was washed with MeOH and CH2Cl2. The filtrate was concentrated to dryness and dried under high vacuum to give the title compound as a grey solid (306 mg). 1H NMR (CDCl$_3$) δ: 3.25 (s, 2H), 3.3-3.2 (m, 1H), 2.81-2.75 (m, 1H), 2.6-2.37 (very broad s, 3H), 2.05-1.98 (m, 2H), 1.95-1.88 (m, 2H), 1.35-1.07 (m, 4H), 1.17 (s, 6H).

E. N-((1r,4r)-4-(2-Hydroxy-2-methylpropoxy)cyclohexyl)-5-iodo-1H-indole-7-carboxamide

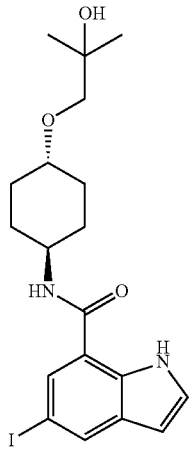 [SMILES: CC(C)(O)CO[C@H]1CC[C@H](NC(=O)c2cc(I)cc3cc[nH]c23)CC1]

5-Iodo-1H-indole-7-carboxylic acid (0.175 g, 0.61 mmol) was stirring in DMF (2 mL) then DIPEA (0.16 ml, 0.914 mmol) was added followed by HATU (0.278 g, 0.732 mmol). The reaction was allowed to stir at rt for ~5 min before 1-(((1r,4r)-4-aminocyclohexyl)oxy)-2-methylpropan-2-ol (0.15 g, 0.801 mmol) was added. The reaction was allowed to stir at same temperature for 4 h before diluting with ethyl acetate and washing with water (2×) followed by brine. The organics were dried over sodium sulfate, filtered and concentrated under reduced pressure. The residue was purified by silica gel chromatography eluting with a gradient from 30-75% ethyl acetate/hexanes yielding N-((1r,4r)-4-(2-hydroxy-2-methylpropoxy)cyclohexyl)-5-iodo-1H-indole-7-carboxamide (0.258 g, 0.565 mmol). 1H NMR (CDCl$_3$) δ: 10.3 (br. s., 1H), 8.11 (s, 1H), 7.56 (s, 1H), 7.29 (t, J=2.64 Hz, 1H), 7.27 (s, 1H), 6.50 (t, J=2.64 Hz, 1H), 6.11 (d, J=7.53 Hz, 1H), 4.02 (m, J=10.9, 10.92, 7.34, 3.73, 3.73 Hz, 1H), 3.29-3.39 (m, 3H), 2.08-2.21 (m, 4H), 1.42-1.55 (m, 2H), 1.30-1.41 (m, 2H), 1.22 (s, 6H). LCMS (ES API) MH+=457

F. N-((1r,4r)-4-(2-Hydroxy-2-methylpropoxy)cyclohexyl)-5-(1H-imidazol-1-yl-1H-indole-7-carboxamide

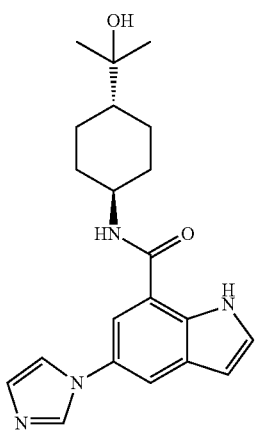 [SMILES: CC(C)(O)[C@H]1CC[C@H](NC(=O)c2cc(-n3ccnc3)cc3cc[nH]c23)CC1]

N-((1r,4r)-4-(2-hydroxy-2-methylpropoxy)cyclohexyl)-5-iodo-1H-indole-7-carboxamide (0.25 g, 0.548 mmol), imidazole (0.112 g, 1.644 mmol), K$_2$CO$_3$ (0.227 g, 1.644 mmol) and copper(I) iodide (0.021 g, 0.110 mmol) in NMP (2 mL) was microwaved at 160° C. for 4 h. The reaction was purified by Agilent reverse phase C18 HPLC eluting with a gradient from 20-95% CH$_3$CN/water/0.1% NH$_4$OH. Fractions recovered were concentrated under reduce pressure then lyophilized to a tan fluffy amorphous solid as N-((1r,4r)-4-(2-hydroxy-2-methylpropoxy)cyclohexyl)-5-(1H-imidazol-1-yl)-1H-indole-7-carboxamide (28 mg, 0.070 mmol). 1H NMR (CDCl$_3$) δ: 10.4 (br. s., 1H), 7.79 (s, 1H), 7.44 (t, J=2.64 Hz, 1H), 7.36-7.41 (m, 1H), 6.63 (t, J=2.51 Hz, 1H), 6.42 (br. s., 1H), 4.04 (br. s., 1H), 3.26-3.38 (m, 3H), 2.10 (br. s., 4H), 1.44 (m, J=12.8 Hz, 4H), 1.21 (s, 6H); a peak is hidden under CDCl$_3$ peak. LCMS (ES API) MH+=397.

Example 7: N-((1r,4r)-4-(2-Hydroxypropoxy)cyclohexyl)-5-(1H-imidazol-1-yl)-1H-indole-7-carboxamide

A. (1r,4r)-N,N-Dibenzyl-4-((2-methylally)oxy)cyclohexanamine

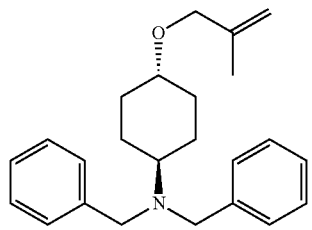 [SMILES: C=C(C)CO[C@H]1CC[C@H](N(Cc2ccccc2)Cc2ccccc2)CC1]

(1r,4r)-4-(Dibenzylamino)cyclohexanol (0.39 g, 1.32 mmol) and 3-iodo-2-methylprop-1-ene (0.481 g, 2.64 mmol) were stirring in DMF (2.5 mL) at 55° C. when a 60% dispersion in mineral oil of NaH (0.106 g, 2.64 mmol) was SLOWLY added portionwise. The reaction stirred at same temperature for ~1 h before cooling to rt and diluting with DCM. The organics were washed with 1.0 N aq. NaOH (1×) then with water (2×) followed by brine. The combined aq. fractions were extracted with DCM and the combined organics were dried over sodium sulfate, filtered and concentrated under reduced pressure yielding a colorless residue as (1r,4r)-N,N-dibenzyl-4-((2-methylallyl)oxy)cyclohexanamine (423 mg, 1.21 mmol). 1H NMR (CDCl$_3$) δ: 1.11-1.23 (m, 2H), 1.27 (s, 3H), 1.39 (qd, J=12.67, 3.03 Hz, 2H) 1.72 (s, 3H), 1.86-1.97 (m, 2H), 2.06 (br. s., 2H), 2.49-2.60 (m, 1H), 3.18 (tt, J=11.0, 4.06 Hz, 1H), 3.61 (s, 4H), 3.88 (s, 2H), 7.18-7.24 (m, 2H), 7.27-7.31 (m, 4H), 7.34-7.38 (m, 4H). LCMS: (ESI) MH+=350.

B. 3-(((1r,4r)-4-(Dibenzylamino)cyclohexyl)oxy)-2-methylpropan-1-ol

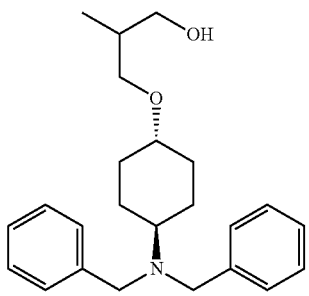 [SMILES: CC(CO)CO[C@H]1CC[C@H](N(Cc2ccccc2)Cc2ccccc2)CC1]

Borane-tetrahydrofuran complex (2.86 mL, 2.86 mmol) was stirring under nitrogen at 0° C. then 2,3-dimethylbut-2-ene (0.354 mL, 2.86 mmol) was added dropwise. After addition the reaction was allowed to stir at the same temperature for 2 h. (1r,4r)-N,N-dibenzyl-4-((2-methylally)oxy)cyclohexanamine (1.0 g, 2.86 mmol) was taken up in THF (6 mL) and added to the reaction slowly. After addition, the reaction stirred at same temperature for ~15 min before warming to rt where it stirred for 1.5 h. TLC showed the reaction to be complete. Thus 35% aq. hydrogen peroxide (0.8 mL, 9.14 mmol) was added and let stir at rt overnight. The solution was diluted with EtOAc, washed with water (2×) and brine. The organics were dried over sodium sulfate, filtered and concentrated under reduced pressure. The residue was purified by silica gel chromatography eluting with a gradient from 15-50% EtOAc/hexanes providing a colorless oil as 3-(((1r,4r)-4-(dibenzylamino)cyclohexyl)oxy)-2-methylpropan-1-ol (580 mg, 1.58 mmol). 1H NMR (CHLOROFORM-d) δ: 0.84 (d, J=7.03 Hz, 3H), 1.09-1.21 (m, 2H), 1.32-1.45 (m, 2H), 1.92 (d, J=12.8 Hz, 2H), 2.00 (ddd, J=11.3, 7.53, 4.02 Hz, 1H), 2.04-2.11 (m, 2H), 2.53 (tt, J=11.8, 3.42 Hz, 1H), 2.86 (dd, J=7.53, 3.76 Hz, 1H), 3.16 (tt, J=10.9, 4.17 Hz, 1H), 3.36 (t, J=8.66 Hz, 1H), 3.51-3.60 (m, 2H), 3.61 (s, 4H), 7.18-7.24 (m, 2H), 7.27-7.32 (m, 4H), 7.34-7.38 (m, 4H). LCMS: (ESI) MH+=368.

C. 3-(((1r,4r)-4-Aminocyclohexyl)oxy)-2-methylpropan-1-ol

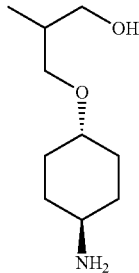

3-(((1r,4r)-4-(Dibenzylamino)cyclohexyl)oxy)-2-methylpropan-1-ol (0.58 g, 1.58 mmol) and palladium hydroxide on carbon (0.111 g, 0.789 mmol) in EtOH (15 mL) was hydrogenated at 40 psi while stirring at rt overnight. TLC showed the reaction to be complete. The solution was filtered through a pad of celite and the celite was rinsed with EtOAc, concentrated under reduced pressure to a colorless oil that turned into a white solid as 3-(((1r,4r)-4-aminocyclohexyl)oxy)-2-methylpropan-1-ol (0.27 g, 1.44 mmol). 1H NMR (METHANOL-d4) δ: 0.91 (d, J=7.03 Hz, 3H), 1.11-1.31 (m, 4H), 1.78-1.86 (m, 1H), 1.86-1.91 (m, 2H), 1.99-2.07 (m, 2H), 2.59-2.69 (m, 1H), 3.17-3.26 (m, 1H), 3.35 (dd, J=9.29, 6.02 Hz, 1H), 3.43 (ddd, J=11.9, 9.98, 6.27 Hz, 2H), 3.49-3.55 (m, 1H).

D. N-((1r,4r)-4-(2-Hydroxypropoxy)cyclohexyl)-5-iodo-1H-indole-7-carboxamide

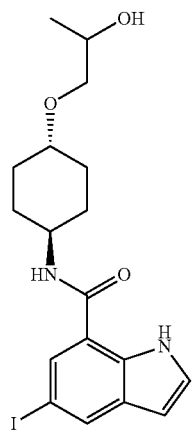 [SMILES: CC(O)CO[C@H]1CC[C@H](NC(=O)c2cc(I)cc3cc[nH]c23)CC1]

5-iodo-1H-indole-7-carboxylic acid (0.3 g, 1.045 mmol) was stirring in DMF (10 mL) then DIPEA (0.3 mL, 1.718 mmol) was added followed by HATU (0.477 g, 1.254 mmol). The reaction stirred at rt for ~10 min before 1-(((1r,4r)-4-aminocyclohexyl)oxy)propan-2-ol (0.235 g, 1.359 mmol) was added and the reaction remained stirring under the same conditions overnight. The reaction was diluted with water and a solid precipitate formed. It was collected by filtration and dried under vacuum overnight to recover a tan solid as N-((1r,4r)-4-(2-hydroxypropoxy)cyclohexyl)-5-iodo-1H-indole-7-carboxamide (443 mg, 1.002 mmol). 1H NMR (DMSO-d$_6$) δ: 11.2 (br. s., 1H), 8.39 (d, J=7.78 Hz, 1H), 8.07 (s, 1H), 7.92 (d, J=1.25 Hz, 1H), 7.33 (t, J=2.76 Hz, 1H), 6.41-6.47 (m, 1H), 4.48 (d, J=4.77 Hz, 1H), 3.77-3.87 (m, 1H), 3.68 (dt, J=11.2, 5.71 Hz, 1H), 3.17-3.28 (m, 3H), 2.04 (d, J=10.0 Hz, 2H), 1.88 (br. s., 2H), 1.35-1.49 (m, 2H), 1.20-1.32 (m, 2H), 1.03 (d, J=6.27 Hz, 3H). LCMS (ES API) MH+=443.

E. N-((1r,4r)-4-(2-Hydroxypropoxy)cyclohexyl)-5-(1H-imidazol-1-yl)-1H-indole-7-carboxamide

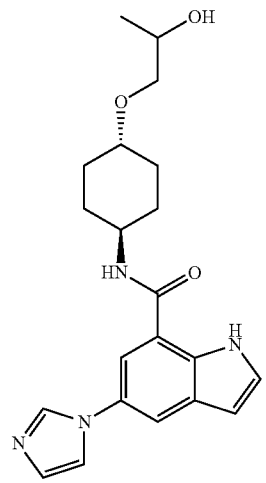 [SMILES: CC(O)CO[C@H]1CC[C@H](NC(=O)c2cc(-n3ccnc3)cc3cc[nH]c23)CC1]

N-((1r,4r)-4-(2-Hydroxypropoxy)cyclohexyl)-5-iodo-1H-indole-7-carboxamide (0.44 g, 0.995 mmol), copper(I) iodide (0.038 g, 0.199 mmol), imidazole (0.169 g, 2.487 mmol) and K₂CO₃ (0.344 g, 2.487 mmol) in NMP (3 mL) was microwaved at 160° C. for 4 h. The reaction was filtered through a pad of celite and washed with ethyl acetate. The filtrate was concentrated under reduced pressure and purified by reverse phase C18 Agilent HPLC eluting with a gradient from 20-95% CAN/water/0.1% NH₄OH. The fractions recovered were concentrated under reduced pressure, and then lyophilized to a solid. The solid was triturated with diethyl ether to recover a tan solid as N-((1r,4r)-4-(2-hydroxypropoxy)cyclohexyl)-5-(1H-imidazol-1-yl)-1H-indole-7-carboxamide (191 mg, 0.474 mmol). 1H NMR (DMSO-d₆) δ: 11.3 (br. s., 1H), 8.37 (d, J=7.53 Hz, 1H), 8.16 (s, 1H), 7.92 (s, 1H), 7.85 (s, 1H), 7.70 (s, 1H), 7.44 (d, J=2.76 Hz, 1H), 7.11 (s, 1H), 6.55 (d, J=2.51 Hz, 1H), 4.48 (d, J=4.77 Hz, 1H), 3.81-3.94 (m, 1H), 3.68 (dt, J=11.2, 5.80 Hz, 1H), 3.32-3.36 (m, 1H), 3.24-3.29 (m, 1H), 3.19-3.24 (m, 1H), 2.05 (d, J=10.5 Hz, 2H), 1.94 (d, J=10.8 Hz, 2H), 1.36-1.50 (m, 2H), 1.21-1.34 (m, 2H), 1.04 (d, J=6.27 Hz, 3H). LCMS (ES API) MH+=383.

Example 8: 3-Chloro-N-((1r,4r)-4-(2-hydroxypropoxy)cyclohexyl)-5-(1H-imidazol-1-yl)-1H-indole-7-carboxamide A. 3-Chloro-N-((1r,4r)-4-(2-hydroxypropoxy)cyclohexyl)-5-(1H-imidazol-1-yl)-1H-indole-7-carboxamide

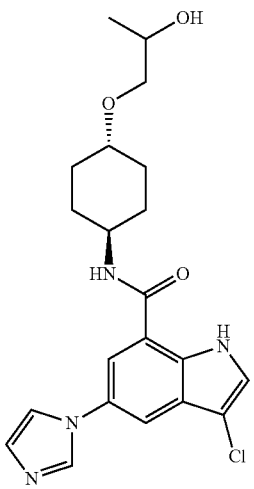 [SMILES: CC(O)CO[C@H]1CC[C@H](NC(=O)c2cc(-n3ccnc3)cc3c(Cl)c[nH]c23)CC1]

N-((1r,4r)-4-(2-Hydroxypropoxy)cyclohexyl)-5-(1H-imidazol-1-yl)-1H-indole-7-carboxamide (0.1 g, 0.261 mmol) was stirring in DMF (2.0 mL) then NCS (0.038 g, 0.288 mmol) dissolved in DMF (0.5 mL) was added. The reaction was allowed to stir at rt overnight, then heated to 50° C. for 14 h before purifying by reverse phase Agilent HPLC eluting with a gradient from 20-95% CH₃CN/water/0.1% NH₄OH. The fractions recovered were concentrated under reduced pressure then lyophilized to a solid. The solid was crystallized from diethyl ether and ethyl acetate to afford a brown solid as 3-chloro-N-((1r,4r)-4-(2-hydroxypropoxy) cyclohexyl)-5-(1H-imidazol-1-yl-1H-indole-7-carboxamide (54.6 mg, 0.130 mmol). 1H NMR (MeOH-d₄) δ: 8.16 (s, 1H), 7.85 (dd, J=9.16, 1.88 Hz, 2H), 7.63 (s, 1H), 7.48 (s, 1H), 7.18 (s, 1H), 3.92-4.01 (m, 1H), 3.81-3.90 (m, 1H), 3.37-3.41 (m, 2H), 3.35 (dd, J=4.14, 2.13 Hz, 1H), 2.03-2.21 (m, 4H), 1.34-1.57 (m, 4H), 1.15 (d, J=6.27 Hz, 3H). LCMS (ES API) MH+=417

Example 9: 5-(1H-Imidazol-1-yl)-N-(1r,4r)-4-(3,3,3-trifluoro-2-hydroxy-2-methylpropoxy)cyclohexyl)-1H-indole-7-carboxamide A. 2-(((1r,4r)-4-(Dibenzylamino)cyclohexyl)oxy) acetic acid hydrochloride

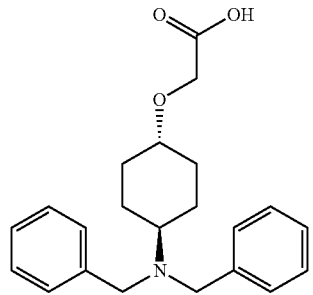 [SMILES: O=C(O)CO[C@H]1CC[C@H](N(Cc2ccccc2)Cc2ccccc2)CC1]

tert-Butyl 2-(((1r,4r)-4-(dibenzylamino)cyclohexyl)oxy) acetate (2.0 g, 4.88 mmol) was stirring in DCM (5.0 mL) and TFA (3 mL) at rt for 1 h before concentrating under reduced pressure. The residue was taken up in 1,4-dioxane (5 mL) and 4.0M HCl in dioxane (2 mL) was added and then stirred at 0° C. Diethyl ether (20 mL) was added and the resulting precipitate was stirred at the same temperature for ~10 min before collecting by vacuum filtration. The solid was washed with diethyl ether providing a white solid as 2-(((1r,4r)-4-(dibenzylamino)cyclohexyl)oxy)acetic acid hydrochloride (2.03 g, 5.21 mmol). LCMS (ES API) MH+=354.

B. 2-(((1r,4r)-4-(Dibenzylamino)cyclohexyl)oxy)-N-methoxy-N-methylacetamide

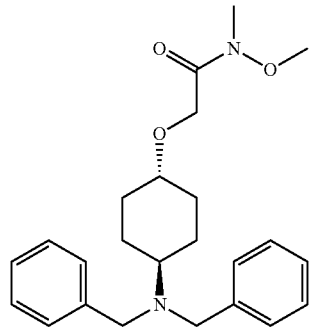 [SMILES: CON(C)C(=O)CO[C@H]1CC[C@H](N(Cc2ccccc2)Cc2ccccc2)CC1]

2-(((1r,4r)-4-(Dibenzylamino)cyclohexyl)oxy)acetic acid hydrochloride (2.0 g, 5.13 mmol) was stirred in DMF (50 mL) followed by the addition of DIPEA (3 mL, 17.18 mmol) and HATU (2.34 g, 6.16 mmol). The reaction stirred at rt for 5 min when N,O-dimethylhydroxylamine hydrochloride (0.751 g, 7.69 mmol) was added. The reaction was allowed to stir at the same temperature overnight. The reaction was diluted with ethyl acetate and washed with sat. aqueous sodium bicarbonate. The organics were separated and washed with brine, dried over sodium sulfate, filtered and concentrated under reduced pressure. The residue was purified by silica gel chromatography eluting with a gradient from 50-90% ethyl acetate/heptanes. The factions recovered were concentrated under reduced pressure and solidified under high vacuum generating a yellowish solid as 2-(((1r, 4r)-4-(dibenzylamino)cyclohexyl)oxy)-N-methoxy-N- methylacetamide (1.735 g, 4.38 mmol). 1H NMR (CDCl₃) δ: 7.18-7.40 (m, 10H), 4.27 (s, 2H), 3.68 (s, 3H), 3.61 (s, 4H), 3.27-3.37 (m, 1H), 3.18 (s, 3H), 2.49-2.60 (m, 1H), 2.14 (d, J=10.8 Hz, 2H), 1.92 (d, J=12.0 Hz, 2H), 1.34-1.46 (m, 2H), 1.17-1.30 (m, 2H). LCMS (ES API) MH+=398.

C. 1-(((1r,4r)-4-(Dibenzylamino)cyclohexyl)oxy)proban-2-one

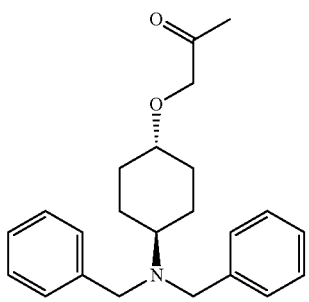 [SMILES: CC(=O)CO[C@H]1CC[C@H](N(Cc2ccccc2)Cc2ccccc2)CC1]

2-(((1r,4r)-4-(Dibenzylamino)cyclohexyl)oxy)-N-methoxy-N-methylacetamide (1.73 g, 4.36 mmol) was stirring in THF (7 mL) in an ice bath when a 3.0 M solution in diethyl ether of methylmagnesium bromide (2 mL, 6.0 mmol) was slowly added. The reaction was allowed to stir at the same temperature for ~10 min before warming to rt and stirred overnight. The reaction was quenched with sat. aqueous NH₄Cl and extracted with ethyl acetate. The organics were washed with brine, dried over sodium sulfate, filtered and concentrated under reduced pressure providing an orange oil as 1-(((1r,4r)-4-(dibenzylamino)cyclohexyl)oxy)propan-2-one (1.52 g, 4.32 mmol). 1H NMR (CDCl₃) δ: 7.34-7.39 (m, 4H), 7.29 (t, 4H), 7.18-7.24 (m, 2H), 4.03 (s, 2H), 3.61 (s, 4H), 3.17-3.26 (m, 1H), 2.50-2.60 (m, 1H), 2.15 (s, 3H), 2.04-2.12 (m, 2H), 1.94 (d, J=12.0 Hz, 2H), 1.33-1.48 (m, 2H), 1.16-1.28 (m, 2H). LCMS (ES API) MH+=352.

D. 3-(((1r,4r)-4-(Dibenzylamino)cyclohexyl)oxy)-1,1,1-trifluoro-2-methylpropan-2-ol

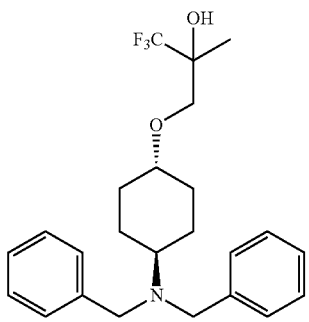 [SMILES: CC(O)(CO[C@H]1CC[C@H](N(Cc2ccccc2)Cc2ccccc2)CC1)C(F)(F)F]

1-(((1r,4r)-4-(Dibenzylamino)cyclohexyl)oxy)propan-2-one (1.0 g, 2.85 mmol) and cesium fluoride (0.432 g, 2.85 mmol) in THF (6.5 mL) were stirring in an ice bath, when trimethyl(trifluoromethyl)silane (1.2 mL, 8.12 mmol) was slowly added. The reaction stirred at the same temperature for 1 h. A 1.0 M solution in THF of TBAF (3.2 mL, 3.20 mmol) was added and the reaction was allowed to stir at 0° C. for 1 h. The reaction was diluted with ethyl acetate and washed with water, followed by brine. The organics were dried over sodium sulfate, filtered and concentrated under reduced pressure to an orange oil that was purified by silica gel chromatography on an ISCO Combiflash eluting with 30% ethyl acetate/heptanes. The fractions recovered were concentrated under reduced pressure to a yellow solid as 3-(((1r,4r)-4-(dibenzylamino)cyclohexyl)oxy)-1,1,1-trifluoro-2-methylpropan-2-ol (0.888 g, 2.107 mmol). 1H NMR (CDCl₃) δ: 7.33-7.39 (m, 4H), 7.27-7.32 (m, 4H), 7.19-7.24 (m, 2H), 3.67 (d, J=9.79 Hz, 1H), 3.61 (s, 4H), 3.35 (dd, J=9.91, 1.13 Hz, 1H), 3.19-3.28 (m, 1H), 2.49-2.59 (m, 1H), 2.06 (d, J=6.53 Hz, 2H), 1.91 (br. s., 2H), 1.34-1.47 (m, 2H), 1.31 (s, 3H), 1.14-1.24 (m, 2H). LCMS (ES API) MH+=422.

E. 3-(((1r,4r)-4-Aminocyclohexyl)oxy)-1,1,1-trifluoro-2-methylpropan-2-ol

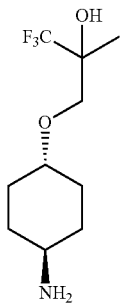

3-(((1r,4r)-4-(Dibenzylamino)cyclohexyl)oxy)-1,1,1-trifluoro-2-methylpropan-2-ol (0.923 mL, 2.107 mmol) and 20 wt % Pearlman's catalyst (0.089 g, 0.632 mmol) was stirring in EtOH (20 mL) and flushed with hydrogen via balloon (3×) before left to stir at rt overnight. The reaction was filtered through a pad of celite and washed with ethyl acetate. The filtrate was concentrated under reduced pressure to a greenish oil as 3-(((1r,4r)-4-aminocyclohexyl)oxy)-1,1,1-trifluoro-2-methylpropan-2-ol (0.483 g, 2.00 mmol). 1H NMR (CDCl₃) δ: 3.70 (d, J=9.79 Hz, 1H), 3.39 (dd, J=9.79, 1.25 Hz, 1H), 3.26-3.34 (m, 1H), 2.71-2.81 (m, 1H), 2.02 (d, J=10.5 Hz, 2H), 1.86-1.95 (m, 2H), 1.28-1.41 (m, 5H), 1.11-1.22 (m, 2H). LCMS (ELSD) MH+=242.

F. 5-Iodo-N-((1r,4r)-4-(3,3,3-trifluoro-2-hydroxy-2-methylpropoxy)cyclohexyl)-1H-indole-7-carboxamide

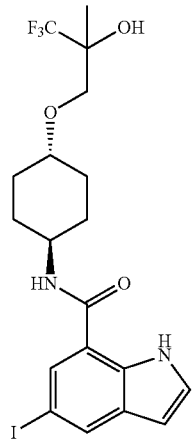 [SMILES: CC(O)(CO[C@H]1CC[C@H](NC(=O)c2cc(I)cc3cc[nH]c23)CC1)C(F)(F)F]

5-Iodo-1H-indole-7-carboxylic acid (0.1 g, 0.348 mmol) was stirring in DMF (3 mL) then DIPEA (0.3 mL, 1.72 mmol) was added followed by HATU (0.159 g, 0.418 mmol). The reaction stirred at rt for ~10 min before 3-(((1r,4r)-4-aminocyclohexyl)oxy)-1,1,1-trifluoro-2-methylpropan-2-ol (0.109 g, 0.453 mmol) was added and the reaction remained stirring under same conditions overnight. The reaction was diluted with water and extracted with diethyl ether (2×). The combined organics were washed with brine, dried over sodium sulfate, filtered and concentrated under reduced pressure. The residue was purified by silica gel chromatography via ISCO Combiflash (12 g column) eluting with a gradient from 30-50% ethyl acetate/heptanes providing a white solid as 5-iodo-N-((1r,4r)-4-(3,3,3-trifluoro-2-hydroxy-2-methylpropoxy)cyclohexyl)-1H-indole-7-carboxamide (122 mg, 0.239 mmol). 1H NMR (CDCl$_3$) δ: 10.3 (br. s., 1H), 8.11 (s, 1H), 7.55 (s, 1H), 7.30 (t, J=2.76 Hz, 1H), 6.49-6.52 (m, 1H), 6.06 (d, J=7.28 Hz, 1H), 3.97-4.08 (m, 1H), 3.74 (d, J=9.79 Hz, 1H), 3.45 (dd, J=9.91, 1.38 Hz, 1H), 3.34-3.42 (m, 1H), 3.14 (s, 1H), 2.08-2.24 (m, 4H), 1.45-1.57 (m, 5H), 1.31-1.42 (m, 2H). LCMS (ES API) MH+=511.

G. 5-(1H-Imidazol-1-yl)-N-((1r,4r)-4-(3,3,3-trifluoro-2-hydroxy-2-methylpropoxy)cyclohexyl)-1H-indole-7-carboxamide

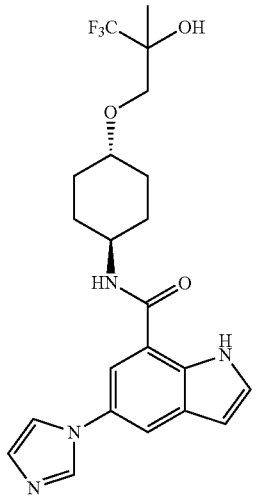 [SMILES: CC(O)(CO[C@H]1CC[C@H](NC(=O)c2cc(-n3ccnc3)cc3cc[nH]c23)CC1)C(F)(F)F]

5-Iodo-N-((1r,4r)-4-(3,3,3-trifluoro-2-hydroxy-2-methylpropoxy)cyclohexyl)-1H-indole-7-carboxamide (0.122 g, 0.239 mmol), imidazole (0.041 g, 0.598 mmol), K$_2$CO$_3$ (0.10 g, 0.724 mmol), and copper(I) iodide (9.11 mg, 0.048 mmol) in NMP (1 mL) was microwaved at 150° C. for 4 h. Additional imidazole (0.016 g, 0.239 mmol) was added and microwaved at same temperature for another 2 h. The reaction was filtered and washed with ethyl acetate and the filtrate was concentrated under reduced pressure. The residue was purified by reverse phase C18 HPLC eluting with a gradient from 20-95% CH$_3$CN/water/0.1% NH$_4$OH. The fractions recovered were concentrated under reduced pressure and lyophilized to a brown solid. The solid was crystallized from ethyl acetate and hexanes to recover a brown solid as 5-(1H-imidazol-1-yl)-N-((1r,4r)-4-(3,3,3-trifluoro-2-hydroxy-2-methylpropoxy)cyclohexyl)-1H-indole-7-carboxamide (15.6 mg, 0.034 mmol). 1H NMR (MeOH-d$_4$) δ: 8.11 (br. s., 1H), 7.90 (d, J=1.76 Hz, 1H), 7.77 (d, J=1.76 Hz, 1H), 7.59 (br. s., 1H), 7.47 (d, J=3.26 Hz, 1H), 7.16 (br. s., 1H), 6.62 (d, J=3.26 Hz, 1H), 3.98 (m, J=4.52 Hz, 1H), 3.57 (s, 2H), 3.35-3.41 (m, 1H), 2.12 (m, J=12.8 Hz, 4H), 1.39-1.58 (m, 4H), 1.35 (s, 3H). LCMS (ES API) MH+=451.

Example 10: 5-(1H-Imidazol-1-yl)-N-((1r,4r)-4-((3,3,3-trifluoro-2-hydroxy-2-methylpropyl)amino)cyclohexyl)-1H-indole-7-carboxamide A. tert-Butyl ((1r,4r)-4-(dibenzylamino)cyclohexyl)carbamate

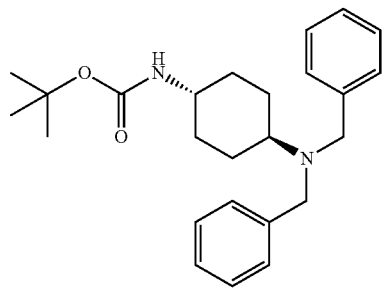 [SMILES: CC(C)(C)OC(=O)N[C@H]1CC[C@H](N(Cc2ccccc2)Cc2ccccc2)CC1]

tert-Butyl ((1r,4r)-4-aminocyclohexyl)carbamate (1.0 g, 4.67 mmol), benzyl bromide (1.2 mL, 10.09 mmol) and K$_2$CO$_3$ (1.612 g, 11.67 mmol) suspended in acetonitrile (15 mL) was heated to 80° C. overnight. After cooling to rt, the solution was filtered and washed with ethyl acetate. It was purified by silica gel chromatography via the ISCO Combiflash (40 g column) eluting with 15% ethyl acetate/heptanes affording a white solid as tert-butyl ((1r,4r)-4-(dibenzylamino)cyclohexyl)carbamate (1.42 g, 3.60 mmol). 1H NMR (CDCl$_3$) δ: 7.33-7.39 (m, 4H), 7.28-7.33 (m, 4H), 7.18-7.23 (m, 2H), 3.62 (s, 4H), 2.49 (t, J=11.5 Hz, 1H), 2.03 (d, J=11.3 Hz, 2H), 1.91 (d, J=12.0 Hz, 2H), 1.40-1.53 (m, 11H), 1.02 (m, J=12.0 Hz, 2H). LCMS (ES API) MH+=395

B. (1r,4r)-N1,N1-Dibenzylcyclohexane-1,4-diamine

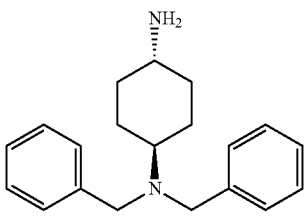 [SMILES: N[C@H]1CC[C@H](N(Cc2ccccc2)Cc2ccccc2)CC1]

tert-Butyl ((1r,4r)-4-(dibenzylamino)cyclohexyl)carbamate (1.4 g, 3.55 mmol) was stirring in dioxane (15 mL) and a 4.0 M solution of HCl (5 mL, 20.0 mmol) in dioxane. The reaction was allowed to stir at rt for 2 h and no reaction was seen. Therefore methanol (10 mL) was added and stirring continued for 1.5 h before concentrating under reduced pressure. The white gummy solid was taken up in DCM and washed with sat. aqueous potassium carbonate (3 mL). The layers were separated and the cloudy organic layer was diluted ethyl acetate then dried over sodium sulfate, filtered and concentrated under reduced pressure yielding a white solid as (1r,4r)-N1,N1-dibenzylcyclohexane-1,4-diamine (1.09 g, 3.70 mmol). 1H NMR (MeOH-d$_4$) δ: 7.35 (d, J=7.43 Hz, 4H), 7.26 (t, J=7.43 Hz, 4H), 7.15-7.21 (m, 2H), 3.60 (s, 4H), 2.44-2.61 (m, 2H), 1.88 (d, J=10.6 Hz, 4H), 1.40-1.56 (m, 2H), 0.95-1.09 (m, 2H). LCMS (ES API) MH+=383.

C. N-((1r,4r)-4-(Dibenzylamino)cyclohexyl)-3,3,3-trifluoro-2-hydroxy-2-methylpropanamide

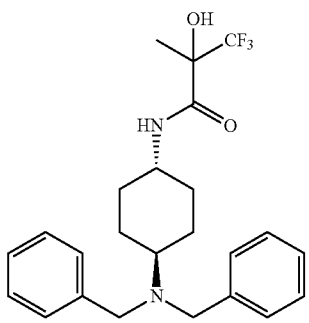 [SMILES: CC(O)(C(=O)N[C@H]1CC[C@H](N(Cc2ccccc2)Cc2ccccc2)CC1)C(F)(F)F]

(1r,4r)-N1,N1-Dibenzylcyclohexane-1,4-diamine (0.95 g, 3.23 mmol) was stirring in DMF (31 mL) then HATU (1.472 g, 3.87 mmol), 3,3,3-trifluoro-2-hydroxy-2-methylpropanoic acid (0.561 g, 3.55 mmol) and DIPEA (1 mL, 5.73 mmol) were added. The reaction was allowed to stir at rt overnight, before diluting with DCM and washing with sat. aqueous sodium bicarbonate, water and brine. The organics were dried over sodium sulfate, filtered and concentrated under reduced pressure. The residue was purified by silica gel chromatography by ISCO Combiflash (24 g column) eluting with a gradient from 20-60% ethyl acetate/heptanes. The fractions recovered yielded a white solid as N-((1r,4r)-4-(dibenzylamino)cyclohexyl)-3,3,3-trifluoro-2-hydroxy-2-methylpropanamide (1.09 g, 2.509 mmol). LCMS (ES API) MH+=435.

D. 3-(((1r,4r)-4-(Dibenzylamino)cyclohexyl)amino)-1,1,1-trifluoro-2-methylpropan-2-ol

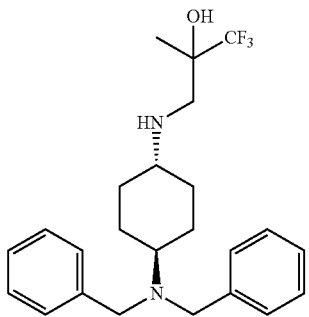 [SMILES: CC(O)(CN[C@H]1CC[C@H](N(Cc2ccccc2)Cc2ccccc2)CC1)C(F)(F)F]

N-((1r,4r)-4-(Dibenzylamino)cyclohexyl)-3,3,3-trifluoro-2-hydroxy-2-methylpropanamide (0.5 g, 1.151 mmol) was stirring in THF (3 mL) in an ice bath when a 1.0 M solution in THF of BH$_3$·THF (3.5 mL, 3.50 mmol) was slowly added. After addition the reaction was warmed to rt then heated to 50° C. for 3 h. The reaction was cooled to rt and placed in an ice bath and quenched with sat. aqueous sodium bicarbonate. The solution was poured into a separatory funnel diluted with water and extracted with ethyl acetate (2×). The combined organics were washed with brine, dried over sodium sulfate, filtered and concentrated under reduced pressure. The residue was purified by silica gel chromatography via ISCO Combiflash (24 g column) eluting with a gradient from 15-60% ethyl acetate/heptanes providing 3-(((1r,4r)-4-(dibenzylamino)cyclohexyl)amino)-1,1,1-trifluoro-2-methylpropan-2-ol (0.103 g, 0.245 mmol). LCMS (ELSD) MH+=421.

E. 3-(((1r,4r)-4-Aminocyclohexyl)amino)-1,1,1-trifluoro-2-methylpropan-2-ol

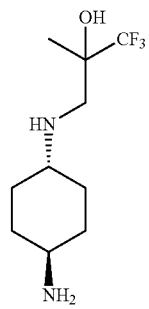

3-(((1r,4r)-4-(Dibenzylamino)cyclohexyl)amino)-1,1,1-trifluoro-2-methylpropan-2-ol (0.1 g, 0.238 mmol) and 20 wt % Pearlman's catalyst (0.017 g, 0.024 mmol) stirring in EtOH (2.5 mL) was hydrogenated via balloon overnight. The reaction was filtered through a pad of celite and washed with ethyl acetate. The filtrate was concentrated under reduced pressure providing 3-(((1r,4r)-4-aminocyclohexyl)amino)-1,1,1-trifluoro-2-methylpropan-2-ol (50.7 mg, 0.211 mmol). 1H NMR (CDCl$_3$) δ: 3.46 (s, 1H), 3.17 (d, J=13.3 Hz, 1H), 2.62-2.72 (m, 1H), 2.35-2.43 (m, 2H), 1.84-1.99 (m, 4H), 1.29 (s, 3H), 1.07-1.19 (m, 4H). LCMS (ESLD) MH+=241.

F. 5-Iodo-N-(1r,4r)-4-((3,3,3-trifluoro-2-hydroxy-2-methylpropyl)amino)cyclohexyl)-1H-indole-7-carboxamide

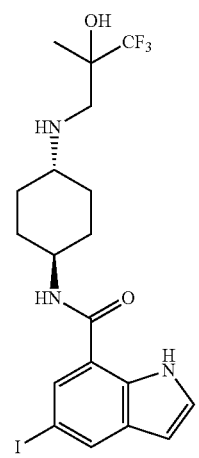 [SMILES: CC(O)(CN[C@H]1CC[C@H](NC(=O)c2cc(I)cc3cc[nH]c23)CC1)C(F)(F)F]

5-Iodo-1H-indole-7-carboxylic acid (0.054 g, 0.187 mmol) was stirring in DMF (2 mL) then DIPEA (0.10 mL, 0.573 mmol) was added followed by HATU (0.075 g, 0.198 mmol). The reaction stirred at rt for ~10 min when 3-(((1r,4r)-4-aminocyclohexyl)amino)-1,1,1-trifluoro-2-methylpropan-2-ol (0.05 g, 0.208 mmol) was added and stirring overnight. The reaction was diluted with water and extracted with diethyl ether (2×). The combined organics were washed with brine, dried over sodium sulfate, filtered and concentrated under reduced pressure. The residue was purified by silica gel chromatography via ISCO Combiflash (12 g column) eluting with a gradient from 30-50% ethyl acetate/heptanes providing a white solid as 5-iodo-N-((1r,4r)-4-((3,3,3-trifluoro-2-hydroxy-2-methylpropyl)amino)cyclohexyl)-1H-indole-7-carboxamide (104 mg, 0.204 mmol). 1H NMR (MeOH-d$_4$) δ: 8.06 (d, J=1.51 Hz, 1H) 7.86 (d, J=1.00 Hz, 1H) 7.33 (d, J=3.26 Hz, 1H) 6.46 (d, J=3.26 Hz, 1H) 3.88-3.97 (m, 1H) 2.92 (d, J=12.3 Hz, 1H) 2.81 (s, 3H) 2.69 (d, J=12.3 Hz, 1H) 2.45-2.54 (m, 1H) 2.01-2.06 (m, 4H) 1.42-1.51 (m, 2H) 1.36 (s, 3H) 1.24-1.34 (m, 2H).

G. 5-(1H-Imidazol-1-yl)-N-((1r,4r)-4-((3,3,3-trifluoro-2-hydroxy-2-methylpropyl)amino)cyclohexyl)-1H-indole-7-carboxamide

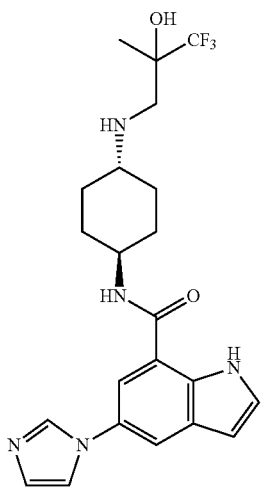 [SMILES: CC(O)(CN[C@H]1CC[C@H](NC(=O)c2cc(-n3ccnc3)cc3cc[nH]c23)CC1)C(F)(F)F]

5-Iodo-N-((1r,4r)-4-((3,3,3-trifluoro-2-hydroxy-2-methylpropyl)amino)cyclohexyl)-1H-indole-7-carboxamide (0.10 g, 0.196 mmol), imidazole (0.045 g, 0.654 mmol), K$_2$CO$_3$ (0.090 g, 0.654 mmol), and copper(I) iodide (8.31 mg, 0.044 mmol) in NMP (1 mL) was microwaved at 160° C. for 4 h. The reaction was filtered and washed with ethyl acetate. The filtrate was concentrated under reduced pressure and the residue was purified by reverse phase C18 Agilent HPLC eluting with a gradient from 20-95% CH$_3$CN/water/NH$_4$OH. The fractions recovered were concentrated under reduced pressure to recover a brown solid residue as 5-(1H-imidazol-1-yl)-N-((1r,4r)-4-((3,3,3-trifluoro-2-hydroxy-2-methylpropyl)amino)cyclohexyl)-1H-indole-7-carboxamide (19.8 mg, 0.040 mmol). 1H NMR (MeOH-d$_4$) δ: 1.26-1.38 (m, 5H) 1.41-1.57 (m, 2H) 2.06 (t, J=10.3 Hz, 4H) 2.43-2.53 (m, 1H) 2.69 (d, J=12.6 Hz, 1H) 2.92 (d, J=12.3 Hz, 1H) 3.92-4.03 (m, 1H) 6.62 (d, J=3.26 Hz, 1H) 7.18 (br. s., 1H) 7.47 (d, J=3.26 Hz, 1H) 7.60 (br. s., 1H) 7.78 (d, J=1.25 Hz, 1H) 7.89 (d, J=1.51 Hz, 1H) 8.12 (br. s., 1H) LCMS (ES API) M+=450.

Example 11: 5-(1H-Imidazol-1-yl)-N-((1r,4r)-4-(3,3,3-trifluoro-2-hydroxy-2-methylpropanamido)cyclohexyl)-1H-indole-7-carboxamide A. N-((1r,4r)-4-Aminocyclohexyl)-3,3,3-trifluoro-2-hydroxy-2-methylpropanamide

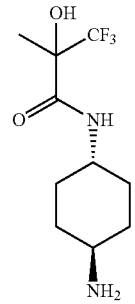 [SMILES: CC(O)(C(=O)N[C@H]1CC[C@H](N)CC1)C(F)(F)F]

N-((1r,4r)-4-(Dibenzylamino)cyclohexyl)-3,3,3-trifluoro-2-hydroxy-2-methylpropanamide (0.69 g, 1.588 mmol) and 20 wt % Pearlman's catalyst (0.223 g, 0.318 mmol) in EtOH (16 mL) was purged with hydrogen via balloon and stirred at rt overnight. The reaction was filtered through celite and washed with ethyl acetate. The filtrate was concentrated under reduced pressure generating a solid as N-((1r,4r)-4-aminocyclohexyl)-3,3,3-trifluoro-2-hydroxy-2-methylpropanamide (455 mg, 1.790 mmol). LCMS (ELSD) MH+=255.

B. 5-Iodo-N-((1r,4r)-4-(3,3,3-trifluoro-2-hydroxy-2-methylpropanamido)cyclohexyl)-1H-indole-7-carboxamide

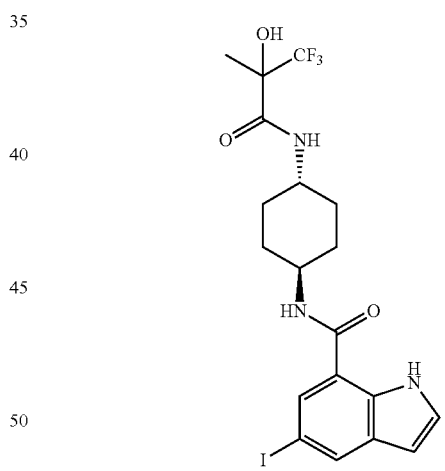

5-Iodo-1H-indole-7-carboxylic acid (0.2 g, 0.697 mmol) was stirring in DMF (6 mL) then DIPEA (0.365 mL, 2.090 mmol) was added followed by HATU (0.30 g, 0.789 mmol). The reaction stirred at rt for ~10 min when N-((1r,4r)-4-aminocyclohexyl)-3,3,3-trifluoro-2-hydroxy-2-methylpropanamide (0.213 g, 0.836 mmol) was added and the reaction stirred overnight. The reaction was diluted with water and extracted with diethyl ether (2×). The combined organics were washed with brine, dried over sodium sulfate, filtered and concentrated under reduced pressure providing an initial brown oil which solidified as 5-iodo-N-((1r,4r)-4-(3,3,3-trifluoro-2-hydroxy-2-methylpropanamido)cyclohexyl)-1H-indole-7-carboxamide (0.40 g, 0.764 mmol). 1H NMR (MeOH-d$_4$) δ: 1.51-1.57 (m, 4H) 1.96 (d, J=6.02 Hz, 1H) 2.05 (d, J=6.02 Hz, 1H) 2.81 (s, 2H) 3.68-3.80 (m, 1H) 3.95

(d, J=3.76 Hz, 1H) 6.47 (d, J=3.01 Hz, 1H) 7.33 (d, J=3.26 Hz, 1H) 7.86 (d, J=1.25 Hz, 1H) 8.07 (d, J=1.25 Hz, 1H). LCMS (ES API) M+=524.

C. 5-(1H-Imidazol-1-yl)-N-((1r,4r)-4-(3,3,3-trifluoro-2-hydroxy-2-methylpropanamido)cyclohexyl)-1H-indole-7-carboxamide

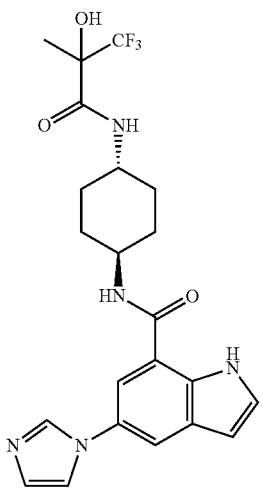 [SMILES: CC(O)(C(=O)N[C@H]1CC[C@H](NC(=O)c2cc(-n3ccnc3)cc3cc[nH]c23)CC1)C(F)(F)F]

5-Iodo-N-((1r,4r)-4-(3,3,3-trifluoro-2-hydroxy-2-methylpropanamido)cyclohexyl)-1H-indole-7-carboxamide (0.40 g, 0.764 mmol), imidazole (0.16 g, 2.350 mmol), $K_2CO_3$ (0.32 g, 2.315 mmol), and copper(I) iodide (0.03 g, 0.158 mmol) in NMP (3 mL) was stirring in an oil bath at 150° C. overnight. The reaction was filtered through a pad of celite and washed with ethyl acetate. The filtrate was concentrated under reduced pressure and purified by reverse phase C18 Agilent HPLC eluting with a gradient from 20-95% $CH_3CN$/water/0.1% $NH_4OH$. The fractions recovered were concentrated under reduced pressure, then triturated with diethyl ether/ethyl acetate yielding a tan solid as 5-(1H-imidazol-1-yl)-N-((1r,4r)-4-(3,3,3-trifluoro-2-hydroxy-2-methylpropanamido)cyclohexyl)-1H-indole-7-carboxamide (124.6 mg, 0.269 mmol). 1H NMR (MeOH-$d_4$) δ: 1.50-1.62 (m, 7H) 1.97 (br. s., 2H) 2.10 (br. s., 2H) 3.35 (br. s., 1H) 6.62 (d, J=3.01 Hz, 1H) 7.16 (br. s., 1H) 7.48 (d, J=3.26 Hz, 1H) 7.59 (br. s., 1H) 7.79 (d, J=1.76 Hz, 1H) 7.91 (d, J=2.01 Hz, 1H) 8.11 (br. s., 1H), one proton is hidden under MeOD peak. LC-MS (ES API) MH+=464.

Example 12: N-((1r,4r)-4-((2,2-Difluoroethyl)amino)cyclohexyl)-5-(1H-imidazol-1-yl)-1H-indole-7-carboxamide

A. tert-Butyl (trans-4-((2,2-difluoroethyl)amino)cyclohexyl)carbamate

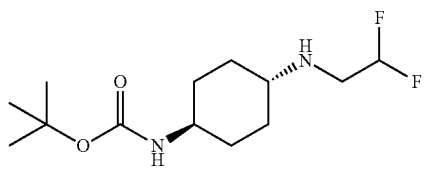 [SMILES: CC(C)(C)OC(=O)N[C@H]1CC[C@H](NCC(F)F)CC1]

N,N-Diisopropylethylamine (1.63 mL, 9.33 mmol) was added to tert-butyl (trans-4-aminocyclohexyl)carbamate (1.00 g, 4.67 mmol) in 1,4-dioxane (7.70 mL) at rt followed by 2,2-difluoroethyl trifluoromethanesulfonate (1.20 g, 5.60 mmol) and the reaction mixture was stirred at 70° C. for 16 h. The reaction mixture was concentrated and the residue was purified by silica gel chromatography, eluting with ethyl acetate:hexanes (3:2) to give tert-butyl (trans-4-((2,2-difluoroethyl)amino)cyclohexyl)carbamate (0.791 g, 2.70 mmol). 1H NMR (DMSO-$d_6$) δ: 6.68 (d, 1H, J=8 Hz), 5.90 (tt, 1H, J=56, 5 Hz), 3.20-3.06 (m, 1H), 2.85 (tt, 2H, J=16, 5 Hz), 2.34-2.22 (m, 1H), 1.82 (brd, 2H, J=12 Hz), 1.80-1.66 (m, 3H), 1.35 (s, 9H), 1.11 (dq, 2H, J=14, 3 Hz), 0.97 (dq, 2H, J=13, 3 Hz). LCMS: (ESI) M+H=279.

B. trans-N1-(2,2-Difluoroethyl)cyclohexane-1,4-diamine dihydrochloride

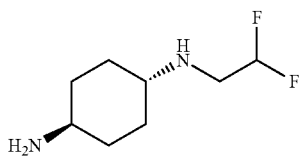 [SMILES: N[C@H]1CC[C@H](NCC(F)F)CC1]

4.0 M Hydrochloric acid (7.10 mL, 28.4 mmol) in dioxane was added to tert-butyl (trans-4-((2,2-difluoroethyl)amino)cyclohexyl)carbamate (0.791 g, 2.84 mmol) in methanol (7.10 mL) at rt and the reaction mixture was stirred for 20 h. The reaction mixture was concentrated to give trans-N1-(2,2-difluoroethyl)cyclohexane-1,4-diamine dihydrochloride (0.705 g, 2.67 mmol). 1H NMR (DMSO-d6) δ: 9.61 (br s, 2H), 8.10 (br s, 3H), 6.48 (tt, 1H, J=54, 3 Hz), 3.58-3.32 (m, 2H), 3.10-2.88 (m, 2H), 2.13 (brd, 2H, J=11 Hz), 2.01 (brd, 2H, J=11 Hz), 1.45 (q, 2H, J=13 Hz), 1.35 (q, 2H, J=13 Hz); LCMS: (ESI) M+H=179.

C. N-((1r,4r)-4-((2,2-Difluoroethyl)amino)cyclohexyl)-5-iodo-1H-indole-7-carboxamide

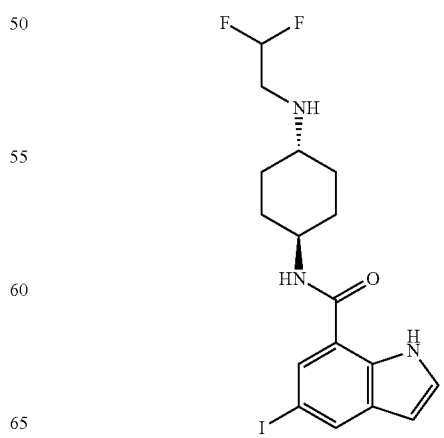

5-Iodo-1H-indole-7-carboxylic acid (0.20 g, 0.697 mmol) was stirring in DMF (6.4 mL) then DIPEA (0.61 mL, 3.48 mmol) was added followed by HATU (0.306 g, 0.805 mmol). The reaction stirred at rt for ~10 min when (1r,4r)-N1-(2,2-difluoroethyl)cyclohexane-1,4-diamine (0.216 g, 0.860 mmol) was added and the reaction remained stirring under same conditions overnight. The reaction was diluted with water and a precipitate formed which was collected and dried under vacuum providing a tan solid as N-((1r,4r)-4-((2,2-difluoroethyl)amino)cyclohexyl)-5-iodo-1H-indole-7-carboxamide (0.213 g, 0.476 mmol). 1H NMR (MeOH-d₄) δ: 8.06 (s, 1H) 7.85 (s, 1H) 7.33 (d, J=3.26 Hz, 1H) 6.47 (d, J=3.01 Hz, 1H) 5.73-6.07 (m, 1H) 3.93 (t, J=11.7 Hz, 1H) 2.99 (td, J=15.4, 4.27 Hz, 2H) 2.55 (t, J=11.0 Hz, 1H) 2.05 (d, J=10.0 Hz, 4H) 1.42-1.55 (m, 2H) 1.22-1.35 (m, 2H). LCMS (ES API) MH+=448

D. N-((1r,4r)-4-((2,2-Difluoroethyl)amino)cyclohexyl)-5-(1H-imidazol-1-yl)-1H-indole-7-carboxamide

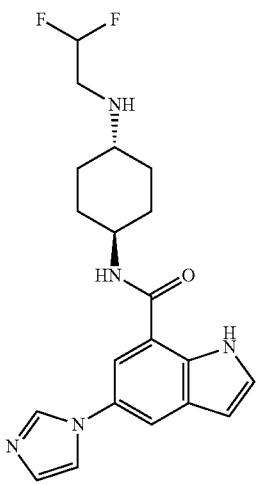 [SMILES: O=C(N[C@H]1CC[C@H](NCC(F)F)CC1)c1cc(-n2ccnc2)cc2cc[nH]c12]

N-((1r,4r)-4-((2,2-Difluoroethyl)amino)cyclohexyl)-5-iodo-1H-indole-7-carboxamide (0.2 g, 0.447 mmol), imidazole (0.091 g, 1.341 mmol), K₂CO₃ (0.185 g, 1.341 mmol), and copper(I) iodide (0.017 g, 0.089 mmol) in NMP (2 mL) was stirring in an oil bath at 150° C. overnight. The reaction was filtered through a pad of celite and washed with ethyl acetate. The filtrate was concentrated under reduced pressure and purified by reverse phase C18 Agilent HPLC eluting with a gradient from 20-95% ACN:water:0.1% NH₄OH. The fractions recovered were concentrated under reduced pressure, then triturated with Et₂O/EtOAc yielding a tan solid as N-((1r,4r)-4-((2,2-difluoroethyl)amino)cyclohexyl)-5-(1H-imidazol-1-yl)-1H-indole-7-carboxamide (45.4 mg, 0.111 mmol). 1H NMR (MeOH-d₄) δ: 8.11 (s, 1H) 7.90 (d, J=1.76 Hz, 1H) 7.78 (d, J=1.76 Hz, 1H), 7.59 (s, 1H) 7.47 (d, J=3.01 Hz, 1H) 7.16 (s, 1H) 6.62 (d, J=3.01 Hz, 1H) 5.74-6.08 (m, 1H) 3.92-4.04 (m, 1H) 2.99 (td, J=15.6, 4.27 Hz, 2H) 2.51-2.59 (m, 1H) 2.08 (d, J=9.79 Hz, 4H) 1.42-1.56 (m, 2H) 1.24-1.38 (m, 2H). LC-MS (ES API) MH+=390

Example 13: 3-Chloro-N-((1r,4r)-4-((2,2-difluoroethyl)amino)cyclohexyl)-5-(1H-imidazol-1-yl)-1H-indole-7-carboxamide

A. 3-Chloro-N-((1r,4r)-4-((2,2-difluoroethyl)amino)cyclohexyl)-5-(1H-imidazol-1-yl)-1H-indole-7-carboxamide

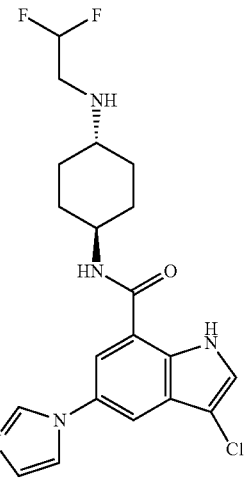

N-((1r,4r)-4-((2,2-Difluoroethyl)amino)cyclohexyl)-5-(1H-imidazol-1-yl)-1H-indole-7-carboxamide (0.023 g, 0.059 mmol) was stirring in DMF (0.5 mL) then NCS (8.72 mg, 0.065 mmol) dissolved in DMF (0.5 mL) was added. The reaction was allowed to stir at rt at 60° C. overnight. Additional NCS (8.72 mg, 0.065 mmol) was added and the reaction stirred at the same temperature overnight. The reaction was purified by reverse phase Agilent HPLC eluting with a gradient from 20-80% ACN:water:0.1% NH₄OH. The fractions recovered were concentrated under reduced pressure then lyophilized to a faint solid as 3-chloro-N-((1r,4r)-4-((2,2-difluoroethyl)amino)cyclohexyl)-5-(1H-imidazol-1-yl)-1H-indole-7-carboxamide (2 mg, 3.79 μmol). 1H NMR (MeOH-d₄) δ: 7.93-8.06 (m, 1H) 7.73 (s, 2H) 7.36-7.44 (m, 2H) 7.17 (br. s., 1H) 5.71-6.10 (m, 1H) 3.89-4.04 (m, 1H) 3.02 (td, J 15.1, 4.14 Hz, 2H) 2.56-2.65 (m, 1H) 2.07 (t, J=13.9 Hz, 4H) 1.25-1.47 (m, 4H). LCMS (ES API) MH+=422.

Example 14: N-((1r,4r)-4-(2-Hydroxy-3-methylbutoxy)cyclohexyl)-5-(1H-imidazol-1-yl)-1H-indole-7-carboxamide

A. 2-(((1r,4r)-4-(Dibenzylamino)cyclohexyl)oxy)acetic acid hydrochloride

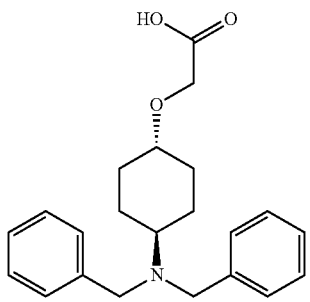 [SMILES: O=C(O)CO[C@H]1CC[C@H](N(Cc2ccccc2)Cc2ccccc2)CC1]

tert-Butyl 2-(((1r,4r)-4-(dibenzylamino)cyclohexyl)oxy) acetate (10 g, 24.42 mmol) was stirring in DCM (200 mL) and TFA (30 mL) at rt for 2 h before concentrating under reduced pressure. The residue was taken up in dioxane (15 mL) and a 4.0 M dioxane solution of HCl was added. The solution was cooled in an ice bath and stirred for 5 min before diethyl ether (30 mL) was added. A white precipitate formed and the suspension was stirred in the ice bath for an additional 30 min before filtering. A white solid was collected as 2-(((1r,4r)-4-(dibenzylamino)cyclohexyl)oxy)acetic acid hydrochloride (10.34 g, 26.5 mmol) with some residual dioxane. 1H NMR (MeOH-d$_4$) δ: 7.44-7.52 (m, 6H), 7.37-7.43 (m, 4H), 4.53 (d, J=13.3 Hz, 2H), 4.27 (d, J=13.3 Hz, 2H), 4.13 (s, 2H), 3.40-3.50 (m, 1H), 3.19-3.28 (m, 1H), 2.30 (d, J=10.5 Hz, 2H), 2.21 (d, J=12.3 Hz, 2H), 1.88 (qd, J=12.6, 2.26 Hz, 2H), 1.29 (q, 2H). LCMS (ES API) MH+=354.

B. 2-(((1r,4r)-4-(Dibenzylamino)cyclohexyl)oxy)-N-methoxy-N-methylacetamide

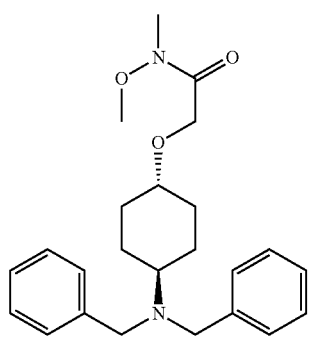 [SMILES: CON(C)C(=O)CO[C@H]1CC[C@H](N(Cc2ccccc2)Cc2ccccc2)CC1]

2-(((1r,4r)-4-(Dibenzylamino)cyclohexyl)oxy)acetic acid (5.0 g, 14.15 mmol) and N,O-dimethylhydroxylamine hydrochloride (2.07 g, 21.2 mmol) was stirring in DMF (100 mL) then HATU (6.45 g, 16.98 mmol) and DIPEA (7.5 mL, 42.9 mmol) were added. The reaction was allowed to stir at rt overnight before diluting with water and extracting with ethyl acetate. The aqueous phase was separated and extracted with ethyl acetate (1×). The combined organics were washed with brine, dried over sodium sulfate, filtered and concentrated under reduced pressure. The residue was purified by silica gel chromatography eluting with a gradient from 15-50% ethyl acetate:heptanes. The fractions recovered off the beginning of column afforded a white solid as product. The column was then flushed with a gradient from 2-10% MeOH:DCM to afforded a yellow solid as product with some minor impurities. The recovered materials were combined to yield 2-(((1r,4r)-4-(dibenzylamino)cyclohexyl) oxy)-N-methoxy-N-methylacetamide (1.28 g, 3.23 mmol). 1H NMR (MeOH-d$_4$) δ: 1.05-1.21 (m, 2H) 1.38-1.53 (m, 2H) 1.91 (d, J=12.3 Hz, 2H) 2.12 (d, J=12.0 Hz, 2H) 2.50 (tt, J=11.76, 3.29 Hz, 1H) 3.17 (s, 3H) 3.59 (s, 4H) 3.71 (s, 3H) 4.29 (br. s., 2H) 7.14-7.22 (m, 2H) 7.26 (t, J=7.40 Hz, 4H) 7.31-7.38 (m, 4H). LCMS (ES API) MH+=397.

C. 1-(((1r,4r)-4-(Dibenzylamino)cyclohexyl)oxy)-3-methylbutan-2-one

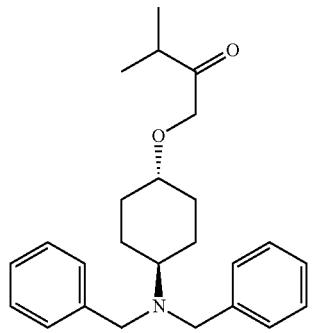 [SMILES: CC(C)C(=O)CO[C@H]1CC[C@H](N(Cc2ccccc2)Cc2ccccc2)CC1]

2-(((1r,4r)-4-(Dibenzylamino)cyclohexyl)oxy)-N-methoxy-N-methylacetamide (1.2 g, 3.03 mmol) was stirring in THF (10 mL) under nitrogen then a 1.3 M solution in THF of isopropylmagnesium chloride (3.5 mL, 4.55 mmol) was slowly added. The reaction was allowed to stir at the same temperature for ~10 min before warming to rt to stir for 1 h. The reaction was placed in an ice bath and quenched with sat. aqueous NH$_4$Cl, then poured into a separatory funnel and diluted with water. The organics were extracted with ethyl acetate and washed with water then brine. The organics were dried over sodium sulfate, filtered and concentrated under reduced pressure yielding a yellow oil as 1-(((1r,4r)-4-(dibenzylamino)cyclohexyl)oxy)-3-methylbutan-2-one (1.18 g, 3.11 mmol). 1H NMR (MeOH-d$_4$) δ: 1.03-1.19 (m, 8H) 1.37-1.51 (m, 2H) 1.90 (d, J=12.6 Hz, 2H) 2.09 (d, J=11.8 Hz, 2H) 2.50 (tt, J=11.8, 3.29 Hz, 1H) 2.72-2.79 (m, 1H) 3.23 (tt, J=10.9, 4.02 Hz, 1H) 3.59 (s, 4H) 4.22 (s, 2H) 7.15-7.21 (m, 2H) 7.26 (t, J=7.40 Hz, 4H) 7.31-7.37 (m, 4H). LCMS (ES API) MH+=381.

D. 1-(((1r,4r)-4-(Dibenzylamino)cyclohexyl)oxy)-3-methylbutan-2-ol

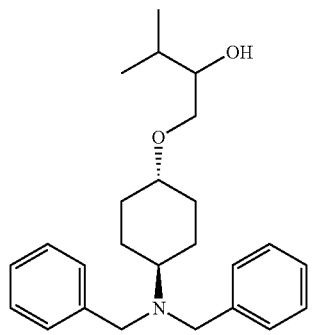 [SMILES: CC(C)C(O)CO[C@H]1CC[C@H](N(Cc2ccccc2)Cc2ccccc2)CC1]

1-(((1r,4r)-4-(Dibenzylamino)cyclohexyl)oxy)-3-methylbutan-2-one (0.558 g, 1.470 mmol) was stirring in THF (3.5 mL) in an ice bath under nitrogen then a 1.0 M solution in THF of LAH (1.5 mL, 1.5 mmol) was slowly added. The reaction was allowed to stir for 1 h before quenching with water (0.05 mL), 15% aq. NaOH (0.05 mL) followed by water (0.15 mL). After quenching the reaction was diluted with ethyl acetate and washed with water followed by brine. The organics were dried over sodium sulfate, filtered and concentrated under reduced pressure to recover an oil as 1-(((1r,4r)-4-(dibenzylamino)cyclohexyl)oxy)-3-methylbutan-2-ol (540 mg, 1.42 mmol). 1H NMR (CDCl₃) δ: 0.90 (d, J=6.78 Hz, 3H) 0.96 (d, J=6.78 Hz, 3H) 1.12-1.21 (m, 2H) 1.34-1.45 (m, 2H) 1.69 (dq, J=13.4, 6.76 Hz, 1H) 1.92 (d, J=13.0 Hz, 2H) 2.04-2.11 (m, 2H) 2.49-2.59 (m, 1H) 3.19 (tt, J=10.8, 4.20 Hz, 1H) 3.26-3.34 (m, 1H) 3.43 (ddt, J=8.41, 5.90, 2.89, 2.89 Hz, 1H) 3.53 (dd, J=9.16, 2.89 Hz, 1H) 3.62 (s, 4H) 7.19-7.24 (m, 2H) 7.27-7.32 (m, 4H) 7.33-7.39 (m, 4H). LCMS (ES API) MH+=382.

E. 1-(((1r,4r)-4-Aminocyclohexyl)oxy)-3-methylbutan-2-ol

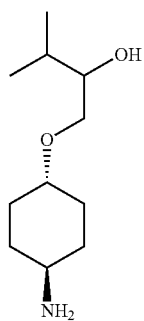

1-(((1r,4r)-4-(Dibenzylamino)cyclohexyl)oxy)-3-methylbutan-2-ol (0.54 g, 1.415 mmol) and 20 wt % Pearlman's catalyst (0.199 g, 0.283 mmol) stirring in EtOH (15 ml) was hydrogenated via balloon for 2 h. The reaction was filtered through celite and the pad was rinsed with ethyl acetate. The filtrate was concentrated under reduced pressure providing a colorless oil as 1-(((1r,4r)-4-aminocyclohexyl)oxy)-3-methylbutan-2-ol (0.258 g, 1.282 mmol). 1H NMR (MeOH-d₄) δ: 3.48-3.57 (m, 1H) 3.38-3.44 (m, 2H) 3.21-3.29 (m, 1H) 2.64 (tt, J=10.6, 3.92 Hz, 1H) 2.01-2.09 (m, 2H) 1.85-1.94 (m, 2H) 1.68-1.80 (m, 1H) 1.11-1.34 (m, 4H) 0.93 (d, J=7.03 Hz, 6H).

F. N-((1r,4r)-4-(2-Hydroxy-3-methylbutoxy)cyclohexyl)-5-(1H-imidazol-1-yl)-1H-indole-7-carboxamide

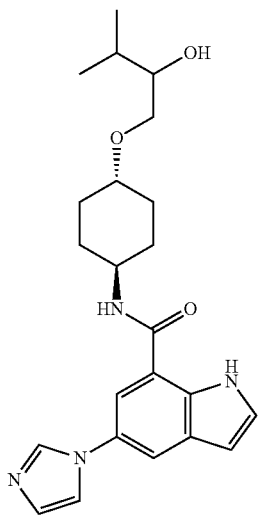 [SMILES: CC(C)C(O)CO[C@H]1CC[C@H](NC(=O)c2cc(-n3ccnc3)cc3cc[nH]c23)CC1]

5-Iodo-1H-indole-7-carboxylic acid (75 mg, 0.261 mmol) was stirring in DMF (2.5 mL) then DIPEA (0.14 mL, 0.802 mmol) was added followed by HATU (0.109 g, 0.287 mmol). The reaction stirred at rt for ~10 min when 1-(((1r,4r)-4-aminocyclohexyl)oxy)-3-methylbutan-2-ol (0.056 g, 0.278 mmol) was added and the reaction was stirred under same conditions overnight. The reaction was diluted with water and extracted with ethyl acetate. The ethyl acetate was washed with sodium bicarbonate followed by brine. The organics were dried over sodium sulfate, filtered and concentrated under reduced pressure providing a golden oil as crude N-((1r,4r)-4-(2-hydroxy-3-methylbutoxy)cyclohexyl)-5-iodo-1H-indole-7-carboxamide. LCMS (ES API) MH+=471.

Crude N-((1r,4r)-4-(2-hydroxy-3-methylbutoxy)cyclohexyl)-5-iodo-1H-indole-7-carboxamide, imidazole (0.053 g, 0.784 mmol), K₂CO₃ (0.108 g, 0.784 mmol), and copper (I) iodide (9.95 mg, 0.052 mmol) in NMP (2.5 mL) were stirring at 150° C. overnight. The reaction was cooled to rt and filtered through a pad of celite. The filtrate was concentrated under reduced pressure and purified by reverse phase C18 Agilent HPLC eluting with a gradient from 20-80% ACN:water:0.1% NH₄OH. The recovered material was triturated with diethyl ether to provide a brown solid as N-((1r,4r)-4-(2-hydroxy-3-methylbutoxy)cyclohexyl)-5-(1H-imidazol-1-yl)-1H-indole-7-carboxamide (19.2 mg, 0.044 mmol). 1H NMR (MeOH-d₄) δ: 8.12 (br. s., 1H) 7.89 (s, 1H) 7.77 (s, 1H) 7.60 (br. s., 1H) 7.47 (d, J=3.01 Hz, 1H) 7.18 (br. s., 1H) 6.62 (d, J=3.01 Hz, 1H) 3.97 (t, J=10.9 Hz, 1H) 3.52-3.60 (m, 1H) 3.41-3.48 (m, 2H) 3.33-3.38 (m, 1H) 2.03-2.20 (m, 4H) 1.71-1.82 (m, 1H) 1.34-1.58 (m, 4H), 0.94 (d, J=6.78 Hz, 6H). LCMS (ES API) MH+=411.

Example 15: N-((1r,4r)-4-(2-Cyclopropyl-2-hydroxypropoxy)cyclohexyl)-5-(1H-imidazol-1-yl)-1H-indole-7-carboxamide A. 1-(((1r,4r)-4-(Dibenzylamino)cyclohexyl)oxy)-2,3-dimethylbutan-2-ol

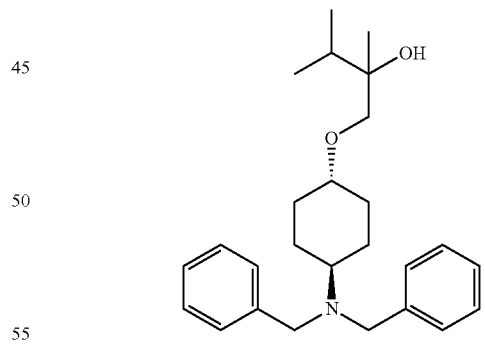

1-(((1r,4r)-4-(Dibenzylamino)cyclohexyl)oxy)-3-methylbutan-2-one (0.625 g, 1.647 mmol) in THF (4.5 mL) was stirring in an ice bath under nitrogen when a 3.0 M solution of methylmagnesium chloride (0.6 mL, 1.80 mmol) in THF was added. The reaction was allowed to stir at the same temperature for 1 h before quenching with sat. aqueous NH₄Cl. The reaction was diluted with water and poured into a separatory funnel, then extracted with ethyl acetate. The organics were washed with water, brine and dried over sodium sulfate followed by filtration. The solvent was removed in vacuo and generating a yellow oil as 1-(((1r, 4r)-4-(dibenzylamino)cyclohexyl)oxy)-2,3-dimethylbutan-2-ol (606 mg, 1.532 mmol). 1H NMR (CDCl₃) δ: 0.85 (d, J=7.03 Hz, 3H) 0.93 (d, J=7.03 Hz, 3H) 1.02 (s, 3H) 1.10-1.21 (m, 2H) 1.33-1.46 (m, 2H) 1.80 (spt, J=6.90 Hz, 1H) 1.88-1.98 (m, 2H) 2.03-2.10 (m, 2H) 2.53 (tt, J=11.6, 3.20 Hz, 1H) 3.17 (tt, J=10.8, 4.20 Hz, 1H) 3.23 (d, J=8.78 Hz, 1H) 3.38 (d, J=8.78 Hz, 1H) 3.62 (s, 4H) 7.18-7.24 (m, 2H) 7.27-7.32 (m, 4H) 7.34-7.39 (m, 4H). LCMS (ES API) MH+=396.

B. 1-(((1r,4r)-4-Aminocyclohexyl)oxy)-2,3-dimethylbutan-2-ol

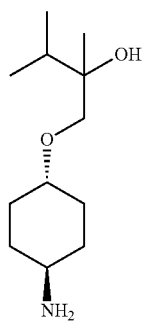

1-(((1r,4r)-4-(Dibenzylamino)cyclohexyl)oxy)-2,3-dimethylbutan-2-ol (0.60 g, 1.517 mmol) and 20 wt % of Pearlman's catalyst (0.213 g, 0.303 mmol) stirring in ethanol (15 mL) was hydrogenated via balloon for 2 h. The reaction was then filtered through a pad of celite and the pad was rinsed with ethyl acetate. The filtrate was concentrated under reduced pressure to recover a colorless oil as 1-(((1r,4r)-4-aminocyclohexyl)oxy)-2,3-dimethylbutan-2-ol (311 mg, 1.444 mmol). 1H NMR (MeOH-d₄) δ: 3.32-3.40 (m, 2H) 3.32-3.40 (m, 2H) 3.18-3.27 (m, 1H) 2.60-2.70 (m, 1H) 2.00-2.09 (m, 2H) 1.79-1.94 (m, 3H) 1.12-1.36 (m, 4H) 1.04 (s, 3H) 0.90 (dd, J=16.6, 7.03 Hz, 6H).

C. N-((1r,4r)-4-(2-Cyclopropyl-2-hydroxypropoxy)cyclohexyl)-5-iodo-1H-indole-7-carboxamide

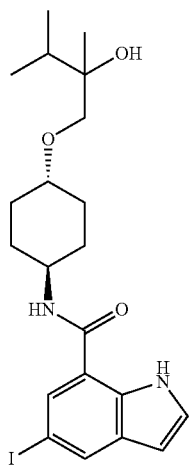 [SMILES: CC(C)C(C)(O)CO[C@H]1CC[C@H](NC(=O)c2cc(I)cc3cc[nH]c23)CC1]

5-Iodo-1H-indole-7-carboxylic acid (0.10 g, 0.348 mmol), 1-(((1r,4r)-4-aminocyclohexyl)oxy)-2-cyclopropylpropan-2-ol (0.089 g, 0.418 mmol), HATU (0.146 g, 0.383 mmol) and DIPEA (0.18 ml, 1.045 mmol) were stirred in DMF (3.3 mL) overnight. The reaction was poured into a separatory funnel then portioned between ethyl acetate and water. The organics were washed with water (1×) followed by brine, then dried over sodium sulfate. The solvent was removed under vacuum and the residue was purified by silica gel chromatography eluting with a gradient from 20-50% ethyl acetatate:heptanes yielding a white solid as N-((1r,4r)-4-(2-cyclopropyl-2-hydroxypropoxy)cyclohexyl)-5-iodo-1H-indole-7-carboxamide (164 mg, 0.340 mmol). 1H NMR (CDCl₃) δ: 0.33-0.41 (m, 3H) 0.43-0.52 (m, 1H) 0.86-0.96 (m, 1H) 1.12 (s, 3H) 1.31-1.42 (m, 2H) 1.44-1.57 (m, 2H) 2.15 (t, J=14.4 Hz, 4H) 3.30-3.47 (m, 3H) 3.97-4.07 (m, 1H) 6.07 (d, J=7.78 Hz, 1H) 6.50 (t, J=2.64 Hz, 1H) 7.30 (t, J=2.64 Hz, 1H) 7.56 (d, J=1.00 Hz, 1H) 8.11 (s, 1H) 10.27 (br. s., 1H). LCMS (ES API) MH+=482.

D. N,N-((1r,4r)-4-(2-Cyclopropyl-2-hydroxypropoxy)cyclohexyl)-5-(1H-imidazol-1-yl)-1H-indole-7-carboxamide

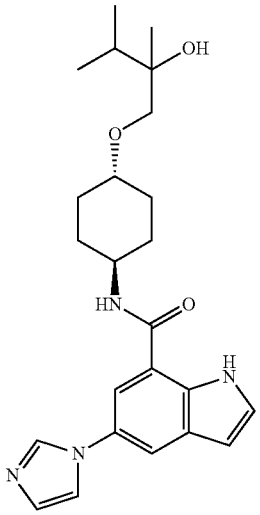 [SMILES: CC(C)C(C)(O)CO[C@H]1CC[C@H](NC(=O)c2cc(-n3ccnc3)cc3cc[nH]c23)CC1]

N-((1r,4r)-4-(2-Cyclopropyl-2-hydroxypropoxy)cyclohexyl)-5-iodo-1H-indole-7-carboxamide (164 mg, 0.340 mmol), imidazole (0.071 g, 1.045 mmol), K₂CO₃ (0.144 g, 1.045 mmol), and copper(I) iodide (0.013 g, 0.070 mmol) in NMP (3 mL) was heated to 140° C. overnight. The reaction was cooled to rt and filtered through celite. The filtrate was concentrated under reduced pressure then purified by reverse phase C18 Agilent HPLC eluting with a gradient from 20-95% ACN:water:0.1% NH₄OH. The recovered oil was triturated with heptanes/diethyl ether to recover a solid as N-((1r,4r)-4-(2-cyclopropyl-2-hydroxypropoxy)cyclohexyl)-5-(1H-imidazol-1-yl)-1H-indole-7-carboxamide (42.6 mg, 0.100 mmol). 1H NMR (MeOH-d₄) δ: 0.28-0.39 (m, 3H) 0.40-0.51 (m, 1H) 0.91-1.02 (m, 1H) 1.13 (s, 3H) 1.36-1.59 (m, 4H) 2.04-2.22 (m, 4H) 3.33-3.42 (m, 3H) 3.91-4.06 (m, 1H) 6.62 (d, J=3.26 Hz, 1H) 7.16 (br. s., 1H) 7.47 (d, J=3.26 Hz, 1H) 7.59 (br. s., 1H) 7.78 (d, J=1.25 Hz, 1H) 7.90 (d, J=1.51 Hz, 1H) 8.11 (br. s., 1H). LCMS (ES API) MH+=423.

Example 16: 5-(1H-Imidazol-1-yl)-N-((1R,4r)-4-(((R)-1-(methylsulfonyl)propan-2-yl)amino)cyclohexyl)-1H-indole-7-carboxamide A. Benzyl (4-(((R)-1-(methylthio)propan-2-yl)amino)cyclohexyl)carbamate

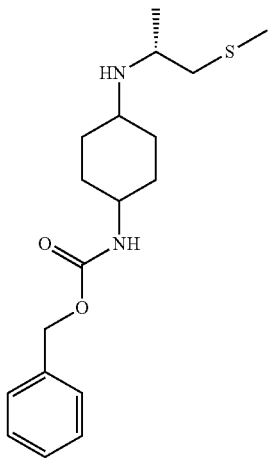 [SMILES: CSC[C@@H](C)NC1CCC(NC(=O)OCc2ccccc2)CC1]

(R)-1-(Methylthio)propan-2-amine (0.304 g, 2.89 mmol) and benzyl (4-oxocyclohexyl)carbamate (0.65 g, 2.63 mmol) were stirring in DCE (13 mL) with molecular sieves for 2 h before sodium triacetoxyborohydride (0.669 g, 3.15 mmol) and a few drops of acetic acid. The reaction stirred at rt overnight, before filtering through a pad of celite and rinsed with DCM. The filtrate was washed with sat. aqueous sodium bicarbonate followed by brine. The organics were dried over sodium sulfate, filtered and concentrated under reduced pressure providing an oil that began to become a gummy solid overnight as benzyl (4-(((R)-1-(methylthio)propan-2-yl)amino)cyclohexyl)carbamate (894 mg, 2.66 mmol). LCMS (ES API) MH+=338.

B. (R)-Benzyl (4-((1-(methylsulfonyl)propan-2-yl)amino)cyclohexyl)carbamate

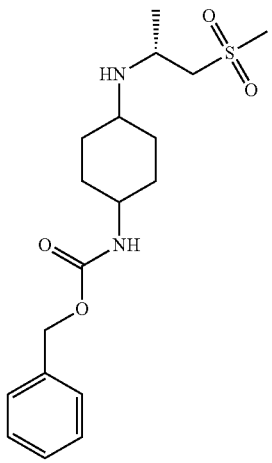 [SMILES: C[C@H](CS(C)(=O)=O)NC1CCC(NC(=O)OCc2ccccc2)CC1]

Benzyl (4-(((R)-1-(methylthio)propan-2-yl)amino)cyclohexyl)carbamate (0.75 g, 2.229 mmol) was stirring in MeOH (5 mL) at rt then a mixture of oxone (1.6 g, 2.60 mmol) in water (2 mL) was added. The reaction stirred at rt for 1 h, then concentrated to aqueous under reduced pressure. The solution was diluted with water and extracted with ethyl acetate (2×). The combined organics were washed with brine then dried over sodium sulfate, filtered and concentrated under reduced pressure generating a colorless solid. The solid was purified by silica gel chromatography (ISCO Combiflash) eluting with a gradient from 2-10% MeOH:DCM yielding a colorless oil as (R)-benzyl (4-((1-(methylsulfonyl)propan-2-yl)amino)cyclohexyl)carbamate (88 mg, 0.239 mmol). LCMS (ES API) MH+=369.

C. (R)-N1-(1-(Methylsulfonyl)propan-2-yl)cyclohexane-1,4-diamine

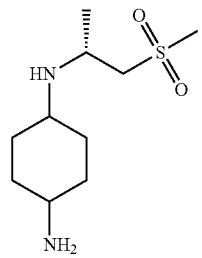

(R)-Benzyl (4-((1-(methylsulfonyl)propan-2-yl)amino)cyclohexyl)carbamate (0.088 g, 0.239 mmol) and 20 wt % Pearlman's catalyst (0.034 g, 0.048 mmol) stirring in ethanol (2.5 mL) was hydrogenated via a balloon at rt overnight. The reaction was filtered through a pad of celite and washed with ethyl acetate. The filtrate was concentrated under reduced pressure to recover a golden oil as (R)-N1-(1-(methylsulfonyl)propan-2-yl)cyclohexane-1,4-diamine (0.053 g, 0.226 mmol). LCMS (ESLD) MH+=235.

D. 5-Iodo-N-(4-((1-(methylsulfonyhpropan-2-yl)amino)cyclohexyl)-1H-indole-7-carboxamide

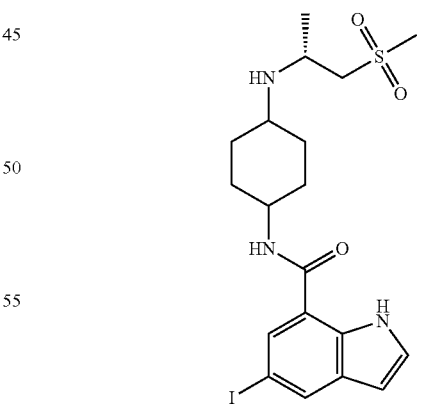

5-Iodo-1H-indole-7-carboxylic acid (0.055 g, 0.192 mmol) in DMF (2.033 ml) had DIPEA (0.1 mL, 0.573 mmol) and HATU (0.081 g, 0.213 mmol) added to it. The reaction stirred at rt for ~10 min when N1-(1-(methylsulfonyl)propan-2-yl)cyclohexane-1,4-diamine (0.05 g, 0.213 mmol) was added and the reaction was stirred overnight. The reaction was diluted with water and extracted with ethyl acetate (2×). The combined organics were washed with sat. aqueous sodium bicarbonate and brine followed by drying over sodium sulfate. The solvent was removed in vacuo yielding a golden oil as 5-iodo-N-(4-((1-(methylsulfonyl)propan-2-yl)amino)cyclohexyl)-1H-indole-7-carboxamide (106 mg, 0.211 mmol). LCMS (ESLD) MH+=504.

E. 5-(1H-Imidazol-1-yl)-N-((1R,4r)-4-(((R)-1-(methylsulfonyl)propan-2-yl)amino)cyclohexyl)-1H-indole-7-carboxamide

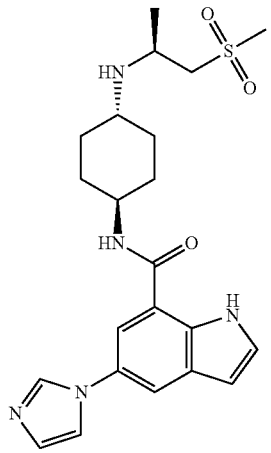 [SMILES: C[C@@H](CS(C)(=O)=O)N[C@H]1CC[C@H](NC(=O)c2cc(-n3ccnc3)cc3cc[nH]c23)CC1]

5-Iodo-N-(4-((1-(methylsulfonyl)propan-2-yl)amino)cyclohexyl)-1H-indole-7-carboxamide (0.10 g, 0.199 mmol), imidazole (0.041 g, 0.596 mmol), $K_2CO_3$ (0.082 g, 0.596 mmol), and copper(I) iodide (7.57 mg, 0.040 mmol) in NMP (1.5 mL) was stirred in an oil bath at 150° C. overnight. The reaction was filtered through a pad of celite and washed with ethyl acetate. The filtrate was concentrated under reduced pressure and purified by reverse phase C18 Agilent HPLC eluting with a gradient from 20-95% ACN:water:0.1% $NH_4OH$. The fractions recovered were concentrated under reduced pressure to recover the diastereomers as brown solids. 5-(1H-imidazol-1-yl)-N-((1R,4r)-4-(((R)-1-(methylsulfonyl)propan-2-yl)amino)cyclohexyl)-1H-indole-7-carboxamide (4.2 mg, 8.52 µmol). 1H NMR (MeOH-$d_4$) δ: 1.24-1.32 (m, 5H) 1.45-1.59 (m, 2H) 2.03-2.13 (m, 4H) 2.61-2.69 (m, 1H) 3.06 (s, 3H) 3.14, (d, J=5.02 Hz, 1H) 3.22 (d, J=7.03 Hz, 1H) 3.42-3.51 (m, 1H) 3.97 (t, J=11.7 Hz, 1H) 6.60-6.66 (m, 1H) 7.16 (br. s., 1H) 7.47 (d, J=3.26 Hz, 1H) 7.59 (br. s., 1H) 7.78 (d, J=1.76 Hz, 1H) 7.90 (d, J=2.01 Hz, 1H) 8.11 (br. s., 1H). LCMS (ESLD) MH+=444.

5-(1H-imidazol-1-yl)-N-((1S,4S)-4-(((R)-1-(methylsulfonyl)propan-2-yl)amino)cyclohexyl)-1H-indole-7-carboxamide (5.6 mg, 0.012 mmol). 1H NMR (MeOH-$d_4$) δ: 1.23 (d, J=6.53 Hz, 3H) 1.63-1.90 (m, 8H) 2.93 (br. s., 1H) 3.08 (s, 3H) 3.19-3.24 (m, 1H) 3.43-3.50 (m, 1H) 4.06 (br. s., 1H) 6.62 (d, J=3.01 Hz, 1H) 7.16 (br. s., 1H) 7.47 (d, J=3.26 Hz, 1H) 7.60 (br. s., 1H) 7.80 (d, J=1.76 Hz, 1H) 7.90 (d, J=1.76 Hz, 1H) 8.12 (br. s., 1H). LCMS (ELSD) MH+=444.

LCMS Method for NAD++ Compound In Vivo Analysis

DIO (diet induced obese) mice free feed on a 60% high fat diet and CD-1 mice were dosed with example 5 at 0, 0.03, 0.1, 0.3, 1, 3, and 10 mg/kg in a formulation of 0.5% HPMC: 0.1% Tween 80 adjusted to pH ~3.5. Blood and tissues were collected 2 hours post dose with blood diluted 1:1 with 5% EDTA in water, mixed and frozen on dry ice. Liver samples were sliced down to 100-250 mgs with the wet weights recorded and tissue placed in a tube and snap frozen in liquid nitrogen.

Samples were stored at -80° C. with sample preparation performed immediately after removal from the freezer due to instability of NAD+ in matrixes at room temperature. Medal bead Lysing matrix was added to each tube along with a 4 fold dilution of the sample with 80:20 acetonitrile: water containing a CD38 inhibitor and $O^{18}$NAD+. Samples were homogenized on a MP FastPrep-24 at 6 m/sec for 60 seconds. The homogenate was centrifuged at 13,000 rpm for 5 minutes with the supernatant transferred to 96 well plate and diluted 1:10 with water. Analysis of NAD+ was performed by injecting 10 µL on a Zorbax Hillic Plus column on an Agilent 1290 HPLC and a Sciex AP14000 Mass Spectrometer monitoring the 664-428 transition for NAD+ and 668-136 for $O^{18}$NAD+ internal standard. The LC separation was achieved with mobile phase A—water with 0.1% ammonium acetate and mobile phase B—acetonitrile w/ 0.1% formic acid starting with 98% mobile phase A followed by 0.5 min gradient to 5% mobile phase. Data was reported as an area ratio of NAD+ to the $O^{18}$NAD+ internal standard.

Determination of Inhibitor IC50 Values

CD38 inhibitors were tested for their capacity to inhibit human CD38 enzyme activity in a colorimetric based assay (Preugschat et. al. (2008) Archives of Biochem and Biophys 479:114). The extracellular domain of human CD38 was expressed in pichia pastoris and purified to homogeneity. The enzyme activity assay was performed in a low-volume 384-well plate in a total volume of 20 µL. A range of concentrations of test compound in 200 nL DMSO was delivered into the assay plate wells. Columns 6 and 18 of the plate contained DMSO with no compound and served as the high signal and low signal controls (no CD38 added), respectively. All additions of assay reagents to the plate were done using a Multidrop Combi, and the plate was shaken 3-5 seconds after each addition. CD38 (0.8 nM) was incubated with test compound in 10 µL containing 100 mM HEPES, pH 7.4, 4 mM EDTA, and 1 mM CHAPS for 30 minutes prior to initiation of the reaction. The reaction was initiated by a 10 µL addition containing 5 mM sodium acetate, pH 4.5, 1 mM CHAPS, 200 µM NAD+ and 500 uM GW323424X. The solutions for each of the two additions were prepared fresh each day from concentrated stocks of the individual components. The final concentrations in the assay were 50 mM HEPES, 2 mM EDTA, 1 mM CHAPS, and 2.5 mM sodium acetate, 100 uM NAD+, 250 µM GW323434X, and 0.4 nM CD38. GW323434X is a 4-pyridynal compound that acts as a nucleophile that participates in the base exchange reaction with the nicotinamide on NAD+ to form a novel dinucleotide that absorbs at 405 nm. Catalytic formation of this novel chromophore was followed in an Envision microplate reader by reading absorbance at two time points, typically 30 minutes apart within the first 45 minutes of the reaction. These time points were established empirically to ensure the rates determined were in a linear range of product formation. Data analysis was performed in the following way using ActivityBase XE (Abase XE). The data from the 15 and 45 minute reads was processed by performing a subtraction function of 45 minute read value minus 15 minute read value for each plate well. The resulting values for non-control wells were converted to % inhibition using the formula $100*((U-C1)/(C2-C1))$ where U is the value of the test well, C1 is the average of the values of the high signal (column 6) control wells, and C2 is the average of the values of the low signal (column 18) control wells. Percent inhibition (y) was plotted versus inhibitor concentration (x), and curve fitting was performed with the following four parameter equation: y=A+((B−A)/(1+(10^x/10^C)^D)), where A is the minimum response, B is the maximum response, C is the $\log_{10}IC50$, and D is the Hill slope. The results for each compound were recorded as pIC50 values (−C in the above equation).

The recombinant extracellular domain of mouse CD38 was expressed in CHO CGE cells and purified to homogeneity. The $pIC_{50}$ values for the inhibitors against mouse CD38 were generated using the enzyme in a fluorescence based assay in which the enzyme reaction occurred in a 10 μL volume in a low-volume 384-well assay plate. The assay quantitated CD38 catalyzed NAD+ hydrolysis over 45 minutes of reaction time in which the rate was linear. A range of concentrations of test compound in 100 nL DMSO was delivered into the assay plate wells. Columns 6 and 18 of the plate contained DMSO and served as the low signal and high signal controls, respectively. Column 18 contained a potent mouse CD38 inhibitor to define the high signal (no enzyme activity) control. Additions to the plate other than compound were done using a Multidrop Combi, and the plate was shaken 3-5 seconds after each addition. CD38 (0.45 nM) was incubated with test compound in 5 uL containing 20 mM HEPES, pH 7.2, 1 mM EDTA, 1 mM CHAPS for 30 minutes prior to initiation of the reaction. The reaction was initiated by a 5 μL addition containing 20 mM HEPES, pH 7.2, 1 mM EDTA, 1 mM CHAPS, and 60 μM NAD+. The final concentrations in the assay were 20 mM HEPES, pH 7.2, 1 mM EDTA, 1 mM CHAPS, 30 μM NAD+, and 0.225 nM mouse CD38. After the reaction time, the amount of NAD+ remaining was quatitated by converting it to NADH using alcohol dehydrogenase (ADH). The ADH was added in 5 μL containing 9U/mL ADH, 90 mM sodium pyrophosphate, pH 8.8, 90 mM ethanol, 1 mM EDTA, and 1 mM CHAPS. The alcohol dehydrogenase reaction was stopped by the addition of 5 μL of 1 M HEPES, pH 7.0, 1.0 mM EDTA, and 1 mM CHAPS containing 0.8 M dithiothreitol (DTT), and the NADH fluorescence was measured in an Envision plate reader (340 nm excitation, 460 nm emission). The solutions for each of the four additions were prepared fresh each day from concentrated stocks of the individual components, except the DTT which was prepared fresh daily from solid. In this assay an increase in enzyme activity results in a decreased measured fluorescent signal. Each compound plate was run in duplicate with (plate A) and without (plate B) ADH. Data were acquired by reading plates in pairs and subtracting the values for plate B from plate A to obtain "corrected" data (accounts for intrinsic fluorescence from test compound). Using Abase XE, "corrected" fluorescence signals for non-control wells are converted to percent inhibition values using the formula 100−100*((U−C2)/(C1−C2)) where U is the "corrected" fluorescence signal value of the test well, Cl is the average of the "corrected" fluorescence values of the low signal (column 6; full CD38 enzyme activity) control wells, and C2 is the average of the "corrected" fluorescence values of the high signal (column 18; 100% inhibited CD38 enzyme activity) control wells. Percent inhibition data were fit using the four parameter curve fit equation described above. For the data presented, the pIC50 values were converted to molar IC50 values according to the equation IC50=10^−pIC50. Statistics were performed on the IC50 values.

| compound | human IC50 (nM) |
|---|---|
| example 1 | ++ |
| example 2 | ++ |
| example 3 | + |
| example 4 | +++ |
| example 5 | +++ |
| example 6 | +++ |
| example 7 | +++ |
| example 8 | ++ |
| example 9 | +++ |
| example 10 | + |
| example 11 | +++ |
| example 12 | +++ |
| example 13 | + |
| example 14 | +++ |
| example 15 | +++ |
| example 16 | + |

IC50 ≤500 nM = +++;
IC50 >500 nM but ≤1000 nM = ++;
IC50 >1000 nM = +

What is claimed is:
1. A compound of Formula I

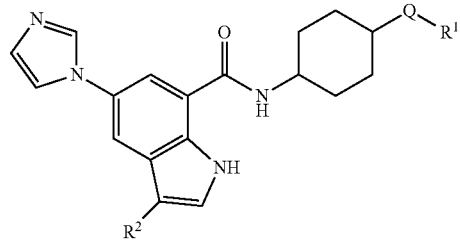

Formula I wherein Q is O, NH, N(H)C(O), or C(O)N(H);
$R^1$ is $C_{1-5}$alkylS(O)$_2$CH$_3$, or $C_{1-6}$alkyl wherein said alkyl can comprise straight-chain portions, branched chain portions, cycloalkyl portions, and wherein said $C_{1-6}$alkyl is optionally substituted by one OH or OCH$_3$ and wherein said $C_{1-6}$alkyl is optionally further substituted by 1 to 3 Fluorine atoms; and
$R^2$ is H, $C_{1-3}$alkyl, or halogen.

2. A pharmaceutically acceptable salt of a compound of Formula I

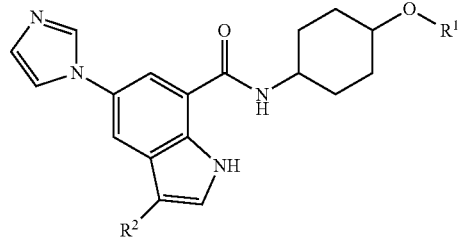

Formula I wherein Q is O, NH, N(H)C(O), or C(O)N(H);
$R^1$ is $C_{1-5}$alkylS(O)$_2$CH$_3$, or $C_{1-6}$alkyl wherein said alkyl can comprise straight-chain portions, branched chain portions, cycloalkyl portions, and wherein said $C_{1-6}$alkyl is optionally substituted by one OH or OCH$_3$ and wherein said $C_{1-6}$alkyl is optionally further substituted by 1 to 3 Fluorine atoms; and
$R^2$ is H, $C_{1-3}$alkyl, or halogen.

3. A compound according to claim 1 wherein $R^2$ is H or Cl.
4. A compound according to claim 1 wherein $R^2$ is H.
5. A compound according to claim 1 wherein the orientation on the cyclohexyl ring is trans as depicted below
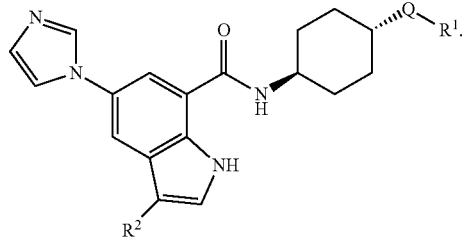
6. The compound
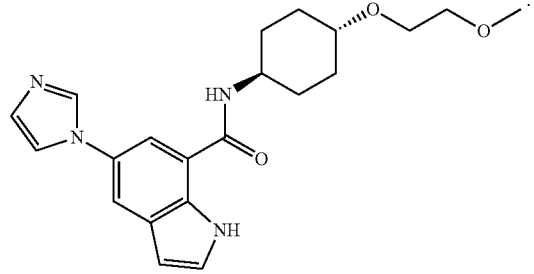 [SMILES: COCCO[C@H]1CC[C@H](NC(=O)c2cc(-n3ccnc3)cc3cc[nH]c23)CC1]
* * * * *